(12) United States Patent
Fuerstner et al.

(10) Patent No.: US 7,977,349 B2
(45) Date of Patent: Jul. 12, 2011

(54) SUBSTITUTED QUINOLONES III

(75) Inventors: Chantal Fuerstner, Muelheim an der Ruhr (DE); Kai Thede, Berlin (DE); Holger Zimmermann, Wuppertal (DE); David Brueckner, Essen (DE); Kerstin Henninger, Wuppertal (DE); Dieter Lang, Velbert (DE); Rudolf Schohe-Loop, Wuppertal (DE)

(73) Assignee: Aicuris GmbH & Co. KG, Wuppertal (DE)

( * ) Notice: Subject to any disclaimer, the term of this patent is extended or adjusted under 35 U.S.C. 154(b) by 258 days.

(21) Appl. No.: 12/188,940

(22) Filed: Aug. 8, 2008

(65) Prior Publication Data

US 2009/0181996 A1 Jul. 16, 2009

Related U.S. Application Data

(63) Continuation of application No. PCT/EP2007/000923, filed on Feb. 2, 2007.

(30) Foreign Application Priority Data

Feb. 9, 2006 (DE) .......................... 10 2006 005 861

(51) Int. Cl.
*A61K 31/4709* (2006.01)
*A61P 31/12* (2006.01)
*C07D 401/10* (2006.01)
*C07D 498/10* (2006.01)
*C07D 401/14* (2006.01)

(52) U.S. Cl. .......... 514/278; 514/312; 546/156; 546/16; 546/19

(58) Field of Classification Search .................. 514/278, 514/312; 546/156, 16, 19
See application file for complete search history.

(56) References Cited

U.S. PATENT DOCUMENTS

| | | | |
|---|---|---|---|
| 4,908,366 A | 3/1990 | Schriewer et al. | |
| 4,959,363 A | 9/1990 | Wentland | |
| 5,051,418 A | 9/1991 | Schriewer et al. | |
| 6,248,739 B1 * | 6/2001 | Turner et al. ................ | 514/235.2 |
| 6,995,262 B1 | 2/2006 | Deroover et al. | |
| 7,141,565 B1 | 11/2006 | Whitten et al. | |
| 7,569,563 B2 | 8/2009 | Schohe-Loop et al. | |
| 2007/0293478 A1 | 12/2007 | Zimmermann et al. | |

FOREIGN PATENT DOCUMENTS

| | | |
|---|---|---|
| CA | 2155021 A1 | 6/1995 |
| DE | 3420743 | 12/1985 |
| DE | 199 37 024 A1 | 2/2001 |
| EP | 0 241 206 | 10/1987 |
| EP | 0 276 700 | 8/1988 |
| EP | 0 352 123 A2 | 1/1990 |
| EP | 0 612 731 | 8/1994 |
| GB | 932487 | 7/1960 |
| WO | WO-96/01262 | 1/1996 |
| WO | WO-97/04775 | 2/1997 |
| WO | WO-97/04779 | 2/1997 |
| WO | WO-00/40561 | 7/2000 |
| WO | WO-02/09758 | 2/2002 |
| WO | WO-02/26713 | 4/2002 |
| WO | WO-02/085886 | 10/2002 |
| WO | WO-02/085886 A2 | 10/2002 |
| WO | WO-03/031397 | 4/2003 |
| WO | WO-03/031397 A1 | 4/2003 |
| WO | WO-03/050107 | 6/2003 |
| WO | WO-2006/008046 A1 | 1/2006 |
| WO | WO-2007/003308 A1 | 1/2007 |

OTHER PUBLICATIONS

English-language translation of International Preliminary Report on Patentability (Chapter II) in PCT/EP2007/000923, dated Nov. 6, 2008.
Accession No. 2003:1549264, CAS No. 384803-97-8 (2004).
Accession No. 2004:147650, CAS No. 371216-54-5 (2001).
Alvernhe et al., *J. Org. Chem.*, 46:4938-4948 (1981).
Cowden et al., *Tetrahedron Letts.*, 41:8661-8664 (2000).
Dorwald, Side Reactions in Organic Synthesis, Wiley, VCH, Weinheim, pp. IX of Preface (2005).
Drug Evaluations by American Medical Association, 6th Ed., pp. 1615-1627 (1986).
Patani et al., *Chem. Rev.*, 96:3147-3176 (1996).
International Preliminary Report on Patentability for Application No. PCT/EP2005/007601, dated Feb. 15, 2007.
International Search Report and Written Opinion for Application No. PCT/EP2005/007601, dated Oct. 21, 2005.
Caroon et al., Journal of Medicinal Chemistry (1981) 24:1320-1328.
Cinatl et al., FEMS Microbiology Reviews (2004) 28:59-77.
Chiu et al., J. Pharmacol. Sci. (2004) 95:311-319.
Chong et al., Abstracts of the 39th Interscience Conference on Antimicrobial Agents and Chemotherapy, Sep. 1999, p. 439.
Da Silva et al., Current Medicinal Chemistry (2003) 10:21-39.
International Search Report and Written Opinion for PCT/EP2007/000923, mailed Sep. 12, 2007, 12 pages.
Kimura et al., Journal of Medicinal Chemistry (1994) 37(20):3344-3352.
McGuirk et al., Journal of Medicinal Chemistry (1992) 35(4):611-620.
Sanchez et al., Journal of Medicinal Chemistry (1995) 338(22):4478-4487.
Smith et al., Journal of Medicinal Chemistry (1995) 38(19):3772-3779.

* cited by examiner

*Primary Examiner* — Sreeni Padmanabhan
*Assistant Examiner* — Sahar Javanmard
(74) *Attorney, Agent, or Firm* — Marshall, Gerstein & Borun LLP

(57) ABSTRACT

The invention relates to substituted quinolones and to methods for their preparation as well as to their use for the production of medicaments for the treatment and/or prophylaxis of diseases, especially for use as antiviral agents, particularly against cytomegaloviruses.

12 Claims, No Drawings

SUBSTITUTED QUINOLONES III

CROSS-REFERENCE TO RELATED APPLICATIONS

This application is a continuation of pending international application PCT/EP2007/000923, filed Feb. 2, 2007, designating US, which claims priority from German patent application DE 10 2006 005 861.5, filed Feb. 9, 2006. The contents of these documents are incorporated herein by reference in their entirety.

BACKGROUND OF THE INVENTION

The invention relates to substituted quinolones and to methods for their preparation as well as to their use for the production of medicaments for the treatment and/or prophylaxis of diseases, especially for use as antiviral agents, particularly against cytomegaloviruses.

WO 00/040561 and U.S. Pat. No. 4,959,363 describe quinolones having activity against viruses of the herpes family. EP-A 612731 describes quinolones as antiviral agents, particularly against HIV. WO 02/009758, WO 02/085886 and WO 03/050107 claim quinolones as broad-spectrum antibiotics. WO 97/004775 and WO 97/004779 describe quinolones as inhibitors of PDE4 and TNFα, among others for the treatment of inflammatory diseases, HIV and HCMV. EP-A 276700 describes 8 cyanoquinolones as antibiotics. WO 02/026713 describes quinolones as antiparasitic compounds.

On the market there are structurally different agents having antiviral activity whose breadth of application is severely restricted owing to a pronounced side-effect profile and a possible development of resistance. New agents for better and more effective therapy are therefore desirable.

SUMMARY OF THE INVENTION

One object of the present invention is therefore to provide new compounds with equal or improved antiviral activity for the treatment of viral infectious diseases in humans and animals.

Surprisingly it has been found that the substituted quinolones described in the present invention have antiviral activity.

The invention relates to compounds of formula

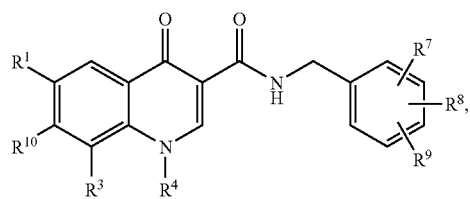

(I)

in which
$R^1$ represents hydrogen, fluorine, chlorine or trifluoromethyl,
$R^3$ represents halogen, hydroxy, $C_1$-$C_4$-alkoxy, cyano, trifluoromethyl, monofluoromethoxy, difluoromethoxy, trifluoromethoxy or ethynyl,
$R^4$ represents $C_1$-$C_6$-alkyl or $C_3$-$C_8$-cycloalkyl,
whereby alkyl can be substituted with 1 to 3 substituents, whereby the substituents are selected independently of one another from the group consisting of halogen, hydroxy, amino, cyano, trifluoromethyl, hydroxycarbonyl, aminocarbonyl, $C_1$-$C_6$-alkoxy, $C_1$-$C_6$-alkylamino, $C_1$-$C_6$-alkylcarbonyl and $C_1$-$C_6$-alkoxycarbonyl,
and
whereby cycloalkyl can be substituted with 1 to 3 substituents, whereby the substituents are selected independently of one another from the group consisting of halogen, hydroxy, amino, cyano, trifluoromethyl, hydroxycarbonyl, aminocarbonyl, $C_1$-$C_6$-alkyl, $C_1$-$C_6$-alkoxy, $C_1$-$C_6$-alkylamino, $C_1$-$C_6$-alkylcarbonyl and $C_1$-$C_6$-alkoxycarbonyl,
or
$R^3$ and $R^4$, together with the atoms to which they are attached, form a ring through a group of formula

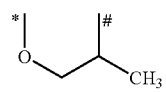

whereby
* is the linkage site to the carbon atom,
and
# is the linkage site to the nitrogen atom,
$R^7$ and $R^8$ independently of one another represent halogen, hydroxy, cyano, trifluoromethyl, monofluoromethoxy, difluoromethoxy, trifluoromethoxy, $C_1$-$C_3$-alkyl or $C_1$-$C_3$-alkoxy,
and
$R^9$ represents hydrogen, halogen, hydroxy, cyano, trifluoromethyl, monofluoromethoxy, difluoromethoxy, trifluoromethoxy, $C_1$-$C_3$-alkyl or $C_1$-$C_3$-alkoxy,
or
$R^8$ represents trifluoromethoxy,
and
$R^7$ and $R^9$ represent hydrogen,
$R^{10}$ represents a group of formula

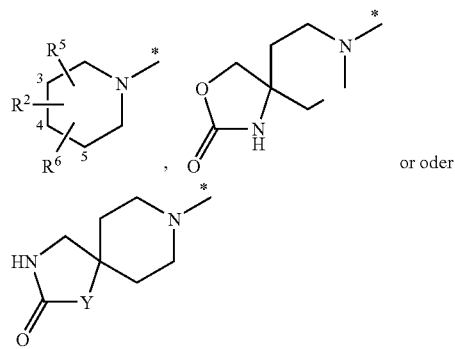

or oder whereby
* is the linkage site to the carbon atom,
$R^2$ is attached at position 3 or 4 and represents hydroxy, hydroxycarbonyl, aminocarbonyl, $C_1$-$C_4$-alkyl, $C_1$-$C_4$-alkoxycarbonyl, $C_3$-$C_6$-cycloalkylaminocarbonyl or optionally hydroxy-substituted $C_1$-$C_6$-alkylaminocarbonyl,
whereby alkyl is substituted with a substituent, whereby the substituent is selected from the group consisting of hydroxy, hydroxycarbonyl, aminocarbonyl, $C_1$-$C_4$-alkoxycarbonyl and 2-oxopyrrolidin-1-yl,
$R^5$ and $R^6$ independently of one another are attached at position 3, 4 or 5 and independently of one another represent hydrogen, hydroxy, methyl, or ethyl, and Y represents a methylene group or an oxygen atom, and their salts, their solvates and the solvates of their salts.

Compounds of the invention are the compounds of formula (I) and (Ia) and their salts, solvates and solvates of the salts; and also the compounds specified below as exemplary embodiment(s) and encompassed by formula (I) and (Ia), and their salts, solvates and solvates of the salts, insofar as the compounds mentioned below and encompassed by formula (I) and (Ia) are not already salts, solvates and solvates of the salts.

The compounds of the invention may, depending on their structure, exist in stereoisomeric forms (enantiomers, diastereomers). The invention accordingly relates to the enantiomers or diastereomers and their respective mixtures. From such mixtures of enantiomers and/or diastereomers it is possible to isolate the stereoisomerically pure constituents, in a known way.

Where the compounds of the invention can occur in tautomeric forms, the present invention includes all of the tautomeric forms.

Salts preferred for the purposes of the present invention are physiologically acceptable salts of the compounds of the invention. Also embraced, however, are salts which, though not themselves suitable for pharmaceutical applications, can nevertheless be used, for example, for isolating or purifying the compounds of the invention.

Physiologically acceptable salts of the compounds of the invention include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds of the invention also include salts of usual bases, such as, by way of example and preferably, alkali metal salts (e.g. sodium and potassium salts), alkaline earth metal salts (e.g. calcium and magnesium salts) and ammonium salts derived from ammonia or organic amines having 1 to 16 carbon atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine and choline.

Solvates, for the purposes of the invention, refer to those forms of the compounds of the invention which in solid or liquid state form a complex through coordination with solvent molecules. Hydrates are a specific form of the solvates, in which the coordination takes place with water.

The present invention further also extends to prodrugs of the compounds of the invention. The term "prodrugs" encompasses compounds which themselves may be biologically active or inactive but during their time of residence in the body are converted into compounds of the invention (by metabolism or hydrolysis, for example).

For the purposes of the present invention the substituents have the following meaning, unless specified otherwise.

Alkyl per se and "alk" and "alkyl" in alkoxy, alkylamino, alkylcarbonyl, alkoxycarbonyl and alkylaminocarbonyl represent a linear or branched alkyl radical usually having 1 to 6, preferably 1 to 4, more preferably 1 to 3 carbon atoms, by way of example and preferably methyl, ethyl, n-propyl, isopropyl, n-butyl, tert-butyl, n-pentyl and n-hexyl.

Alkoxy by way of example and preferably represents methoxy, ethoxy, n-propoxy, isopropoxy, n-butoxy, tert-butoxy, n-pentoxy and n-hexoxy.

Alkylamino represents an alkylamino radical having one or two alkyl substituents (selected independently of one another), by way of example and preferably methylamino, ethylamino, n-propylamino, isopropylamino, n-butylamino, tert-butylamino, n-pentylamino, n-hexylamino, N,N-dimethylamino, N,N-diethylamino, N-ethyl-N-methylamino, N-methyl-N-n-propylamino, N-isopropyl-N-n-propylamino, N-methyl-N-n-butylamino, N-tert-butyl-N-methylamino, N-ethyl-N-n-pentylamino and N-n-hexyl-N-methylamino. $C_1$-$C_3$-Alkylamino represents for example a monoalkylamino radical having 1 to 3 carbon atoms or a dialkylamino radical having 1 to 3 carbon atoms per alkyl substituent.

Alkylcarbonyl by way of example and preferably represents acetyl and propanoyl.

Alkoxycarbonyl by way of example and preferably represents methoxycarbonyl, ethoxycarbonyl, n-propoxycarbonyl, isopropoxycarbonyl, n-butoxycardonyl, tert-butoxycarbonyl, n-pentoxycarbonyl and n-hexoxycarbonyl.

Alkylaminocarbonyl represents an alkylaminocarbonyl radical having one or two alkyl substituents (selected independently of one another), by way of example and preferably methylaminocarbonyl, ethylaminocarbonyl, n-propylaminocarbonyl, isopropylaminocarbonyl, tert-butylaminocarbonyl, n-pentylaminocarbonyl, n-hexylaminocarbonyl, N,N-dimethylaminocarbonyl, N,N-diethylaminocarbonyl, N-ethyl-N-methylaminocarbonyl, N-methyl-N-n-propylaminocarbonyl, N-isopropyl-N-n-propylaminocarbonyl, N-methyl-N-n-butylaminocarbonyl, N-tert-butyl-N-methylaminocarbonyl, N-ethyl-N-n-pentylaminocarbonyl and N-n-hexyl-N-methylaminocarbonyl. $C_1$-$C_3$-Alkylaminocarbonyl represents for example a monoalkylaminocarbonyl radical having 1 to 3 carbon atoms or a dialkylaminocarbonyl radical having 1 to 3 carbon atoms per alkyl substituent.

Cycloalkyl represents a cycloalkyl group usually having 3 to 8, preferably 3 to 5 carbon atoms. Preferred examples of cycloalkyl include cyclopropyl, cyclobutyl, cyclopentyl, cyclohexyl and cycloheptyl.

Cycloalkylaminocarbonyl represents a cycloalkyl group usually having 3 to 6 carbon atoms which is attached via an aminocarbonyl group. Preferred examples of cycloalkylaminocarbonyl include cyclopropylaminocarbonyl, cyclobutylaminocarbonyl, cyclopentylaminocarbonyl and cyclohexylaminocarbonyl.

Halogen represents fluorine, chlorine, bromine and iodine, preferably fluorine and chlorine.

In the formula of the group which can stand for $R^3$ and $R^4$, the end point of the line adjacent to which there is an * or #, does not represent a carbon atom or a $CH_2$ group but is rather a component of the bond to the atom to which $R^3$ and $R^4$ are attached.

In formulae of the group which can stand for $R^{10}$, the end point of the line adjacent to which there is an *, does not represent a carbon atom or a $CH_2$ group but is rather a component of the bond to the atom to which $R^{10}$ is attached.

Preference is given to those compounds of formula (I) which conform to formula

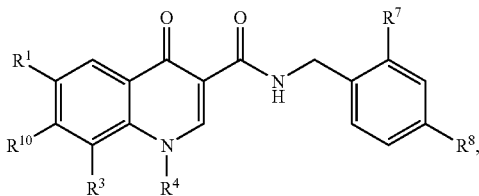

in which
R¹ represents hydrogen, fluorine, chlorine or trifluoromethyl,
R³ represents halogen, hydroxy, $C_1$-$C_4$-alkoxy, cyano, trifluoromethyl, monofluoromethoxy, difluoromethoxy, trifluoromethoxy or ethynyl,
R⁴ represents $C_1$-$C_6$-alkyl or $C_3$-$C_8$-cycloalkyl,
whereby alkyl can be substituted with 1 to 3 substituents, whereby the substituents are selected independently of one another from the group consisting of halogen, hydroxy, amino, cyano, trifluoromethyl, hydroxycarbonyl, aminocarbonyl, $C_1$-$C_6$-alkoxy, $C_1$-$C_6$-alkylamino, $C_1$-$C_6$-alkylcarbonyl and $C_1$-$C_6$-alkoxycarbonyl,
and
whereby cycloalkyl can be substituted with 1 to 3 substituents, whereby the substituents are selected independently of one another from the group consisting of halogen, hydroxy, amino, cyano, trifluoromethyl, hydroxycarbonyl, aminocarbonyl, $C_1$-$C_6$-alkyl, $C_1$-$C_6$-alkoxy, $C_1$-$C_6$-alkylamino, $C_1$-$C_6$-alkylcarbonyl and $C_1$-$C_6$-alkoxycarbonyl,
or
R³ and R⁴, together with the atoms to which they are attached, form a ring through a group of formula

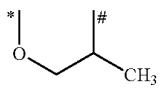

whereby
* is the linkage site to the carbon atom,
and
# is the linkage site to the nitrogen atom,
R⁷ and R⁸ independently of one another represent halogen, hydroxy, cyano, trifluoromethyl, monofluoromethoxy, difluoromethoxy, trifluoromethoxy, $C_1$-$C_3$-alkyl or $C_1$-$C_3$-alkoxy,
R¹⁰ represents a group of formula

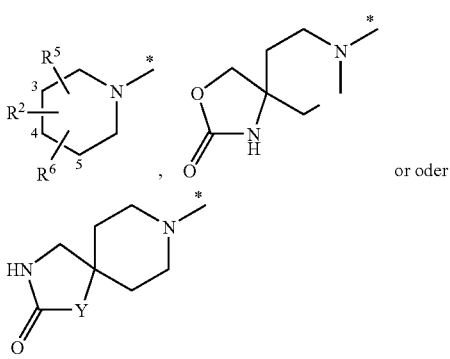

whereby
* is the linkage site to the carbon atom,
R² is attached at position 3 or 4 and represents hydroxy, hydroxycarbonyl, aminocarbonyl, $C_1$-$C_4$-alkyl or $C_1$-$C_4$-alkoxycarbonyl,
whereby alkyl is substituted with a substituent, whereby the substituent is selected from the group consisting of hydroxy, hydroxycarbonyl, aminocarbonyl and $C_1$-$C_4$-alkoxycarbonyl,
R⁵ and R⁶ independently of one another are attached at position 3, 4 or 5 and independently of one another represent hydrogen, hydroxy, methyl, or ethyl,
and
Y represents a methylene group or an oxygen atom,
and their salts, their solvates and the solvates of their salts.

Preference is also given to those compounds of formula (I) and (Ia) in which
R¹ represents hydrogen, fluorine or chlorine,
R³ represents halogen, hydroxy, $C_1$-$C_3$-alkoxy, cyano, trifluoromethyl, monofluoromethoxy, difluoromethoxy or trifluoromethoxy,
R⁴ represents $C_1$-$C_6$-alkyl or $C_3$-$C_6$-cycloalkyl,
whereby alkyl can be substituted with 1 to 3 substituents, whereby the substituents are selected independently of one another from the group consisting of halogen, hydroxy, amino, cyano, trifluoromethyl and $C_1$-$C_4$-alkoxy,
and
whereby cycloalkyl can be substituted with 1 to 3 substituents, whereby the substituents are selected independently of one another from the group consisting of halogen, hydroxy, amino, cyano, trifluoromethyl, $C_1$-$C_4$-alkyl and $C_1$-$C_4$-alkoxy,
or
R³ and R⁴, together with the atoms to which they are attached, form a ring through a group of formula

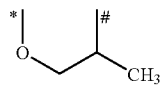

whereby
* is the linkage site to the carbon atom,
and
# is the linkage site to the nitrogen atom,
R⁷ and R⁸ independently of one another represent halogen, cyano, trifluoromethyl, monofluoromethoxy, difluoromethoxy, trifluoromethoxy, $C_1$-$C_3$-alkyl or $C_1$-$C_3$-alkoxy,
R¹⁰ represents a group of formula

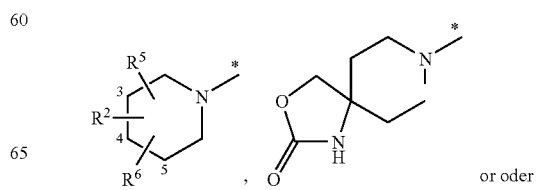

-continued

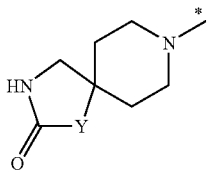

whereby
* is the linkage site to the carbon atom,
$R^2$ is attached at position 3 or 4 and represents hydroxy, hydroxycarbonyl, aminocarbonyl, $C_1$-$C_4$-alkyl or $C_1$-$C_4$-alkoxycarbonyl,
whereby alkyl is substituted with a substituent, whereby the substituent is selected from the group consisting of hydroxycarbonyl and $C_1$-$C_4$-alkoxycarbonyl,
$R^5$ and $R^6$ independently of one another are attached at position 3, 4 or 5 and independently of one another represent hydrogen, hydroxy, methyl or ethyl,
and
Y represents a methylene group or an oxygen atom,
and their salts, their solvates and the solvates of their salts.

Preference is also given to those compounds of formula (I) and (Ia) in which
$R^1$ represents hydrogen or fluorine,
$R^3$ represents chlorine, hydroxy, methoxy, ethoxy, cyano, trifluoromethyl, monofluoromethoxy, difluoromethoxy or trifluoromethoxy,
$R^4$ represents $C_1$-$C_4$-alkyl, cyclopropyl, cyclobutyl or cyclopentyl,
whereby alkyl can be substituted with 1 to 3 substituents, whereby the substituents are selected independently of one another from the group consisting of halogen, trifluoromethyl and $C_1$-$C_4$-alkoxy,
and
whereby cyclopropyl, cyclobutyl and cyclopentyl can be substituted with 1 to 3 substituents, whereby the substituents are selected independently of one another from the group consisting of halogen, trifluoromethyl, methyl, ethyl, methoxy and ethoxy,
or
$R^3$ and $R^4$, together with the atoms to which they are attached, form a ring through a group of formula

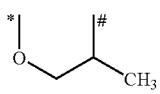

whereby
* is the linkage site to the carbon atom,
and
# is the linkage site to the nitrogen atom,
$R^7$ and $R^8$ independently of one another represent chlorine, bromine, trifluoromethyl, monofluoromethoxy, difluoromethoxy, trifluoromethoxy, methyl or methoxy, $R^{10}$ represents a group of formula

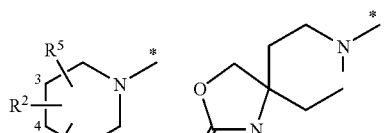

whereby
* is the linkage site of the carbon atom,
$R^2$ is attached at position 3 or 4 and represents hydroxy, hydroxycarbonyl, aminocarbonyl, methyl, ethyl or $C_1$-$C_4$-alkoxycarbonyl,
whereby methyl and ethyl are substituted with a substituent, whereby the substituent is selected from the group consisting of hydroxycarbonyl and $C_1$-$C_4$-alkoxycarbonyl,
$R^5$ is attached at position 3 and represents hydrogen, hydroxy or methyl,
$R^6$ is attached at position 5 and represents hydrogen, hydroxy or methyl,
and
Y represents a methylene group or an oxygen atom,
and their salts, their solvates and the solvates of their salts.

Preference is also given to those compounds of formula (I) and (Ia) in which
$R^1$ represents fluorine,
$R^3$ represents chlorine, hydroxy, methoxy, or ethoxy
$R^4$ represents $C_1$-$C_3$-alkyl, cyclopropyl or cyclobutyl,
whereby alkyl can be substituted with 1 to 2 substituents, whereby the substituents are selected independently of one another from the group consisting of fluorine and trifluoromethyl, and
whereby cyclopropyl and cyclobutyl can be substituted with 1 to 3 fluorine substituents,
$R^7$ and $R^8$ independently of one another represent chlorine, trifluoromethyl, trifluoromethoxy or methyl,
$R^{10}$ represents a group of formula

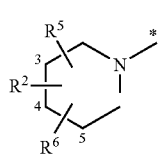 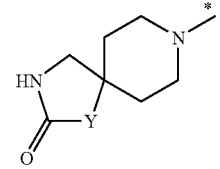

whereby
* is the linkage site to the carbon atom,
$R^2$ is attached at position 3 or 4 and represents hydroxy, hydroxycarbonyl, aminocarbonyl, methyl or ethyl,
whereby methyl and ethyl are substituted with a hydroxycarbonyl substituent,
$R^5$ is attached at position 3 and represents hydrogen or methyl,
$R^6$ is attached at position 5 and represents hydrogen or methyl, and Y represents a methylene group, and their salts, their solvates and the solvates of their salts.

Preference is also given to those compounds of formula (I) and (Ia), in which $R^1$ represents fluorine.

Preference is also given to those compounds of formula (I) and (Ia) in which $R^2$ is attached at position 3 or 4 and represents hydroxy, hydroxycarbonyl, aminocarbonyl or methyl, whereby methyl is substituted with a hydroxycarbonyl substituent.

Preference is also given to those compounds of formula (I) and (Ia) in which $R^2$ represents hydroxycarbonyl or hydroxycarbonylmethyl.

Preference is also given to those compounds of formula (I) und (Ia), in which $R^3$ represents halogen, hydroxy, $C_1$-$C_3$-alkoxy, cyano, trifluoromethyl, monofluoromethoxy, difluoromethoxy, trifluoromethoxy or ethynyl.

Preference is also given to those compounds of formula (I) und (Ia), in which $R^3$ represents halogen, cyano, methoxy, trifluoromethyl, monofluoromethoxy, difluoromethoxy, trifluoromethoxy or ethynyl.

Preference is also given to those compounds of formula (I) und (Ia), in which $R^3$ represents halogen, cyano, methoxy, trifluoromethyl, monofluoromethoxy, difluoromethoxy or trifluoromethoxy.

Preference is also given to those compounds of formula (I) und (Ia), in which $R^3$ represents chlorine, cyano, methoxy, trifluoromethyl, monofluoromethoxy, difluoromethoxy or trifluoromethoxy.

Preference is also given to those compounds of formula (I) and (Ia) in which $R^3$ represents chlorine, methoxy, trifluoromethyl or difluoromethoxy.

Preference is also given to those compounds of formula (I) and (Ia) in which $R^3$ represents chlorine or methoxy.

Preference is also given to those compounds of formula (I) and (Ia) in which $R^3$ represents chlorine, hydroxy, methoxy or ethoxy.

Preference is also given to those compounds of formula (I) and (Ia) in which $R^4$ represents cyclopropyl or 2-fluorocycloprop-1-yl.

Preference is also given to those compounds of formula (I) and (Ia) in which $R^4$ represents 2,2,2-trifluoroethyl, 2,2-difluoroethyl, 2-fluoroethyl, 1-fluoroprop-2-yl or 1,1,1-trifluoroprop-2-yl.

Preference is also given to those compounds of formula (I) and (Ia) in which $R^4$ represents 2,2,2-trifluoroethyl.

Preference is also given to those compounds of formula (I) and (Ia) in which $R^5$ and $R^6$ represent hydrogen or methyl.

Preference is also given to those compounds of formula (I) in which $R^7$ and $R^8$ independently of one another represent halogen, trifluoromethyl, monofluoromethoxy, difluoromethoxy, trifluoromethoxy, methyl or methoxy, and $R^9$ represents hydrogen or methyl.

Preference is also given to those compounds of formula (I) and (Ia) in which $R^7$ represents chlorine or methyl and $R^8$ represents chlorine, trifluoromethyl or trifluoromethoxy.

Preference is also given to those compounds of formula (I) in which $R^9$ represents hydrogen.

Preference is also given to those compounds of formula (I) and (Ia) in which $R^{10}$ represents a group of formula

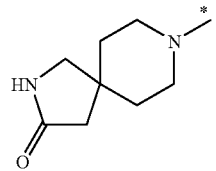

whereby * is the linkage site to the carbon atom.

The radical definitions stated specifically in the respective combinations and preferred combinations of radicals are also replaced as desired by radical definitions of another combination, irrespective of the particular combination of the radicals that are specified.

Very particular preference is given to combinations of two or more of the abovementioned preferred ranges.

The invention further relates to a method for the preparation of the compounds of formula (I), in which

[A] compounds of formula

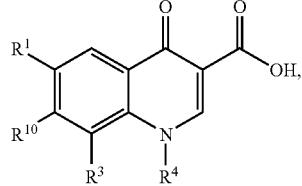

(II)

in which
$R^1$, $R^3$, $R^4$ and $R^{10}$ have the meaning indicated above,
are reacted with compounds of formula

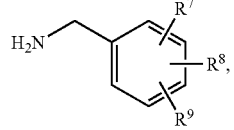

(III)

in which
$R^7$, $R^8$ and $R^9$ have the meaning indicated above
or
[B] compounds of formula

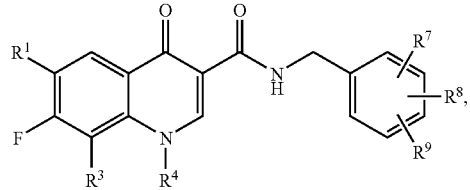

(IV)

in which
$R^1$, $R^3$, $R^4$, $R^7$, $R^8$ and $R^9$ have the meaning indicated above,
are reacted with compounds of formula

(V)

$R^{10}$—H, in which
$R^{10}$ has the meaning indicated above,
or
[C] compounds which are formed by process [A] or [B] and carry any ester group in the radical $R^{10}$ are hydrolysed with a base to form the corresponding acid. (The ester group may but does not have to correspond to the definition of $R^{10}$.)

The reaction of method [A] in general takes place in inert solvents, in the presence of a dehydrating reagent, where appropriate in the presence of a base, preferably in a temperature range from −30° C. to 50° C. under atmospheric pressure.

Examples of inert solvents include halogenated hydrocarbons such as dichloromethane or trichloromethane, hydrocarbon such as benzene, nitromethane, dioxane, dimethylformamide or acetonitrile. It is also possible to use mixtures of the solvents. Of particular preference is dichloromethane or dimethylformamide.

Examples of bases include alkali metal carbonates, such as sodium or potassium carbonate or hydrogen carbonate, or organic bases such as trialkylamines, e.g. triethylamine, N-methylmorpholine, N-methylpiperidine, 4-dimethylaminopyridine or diisopropylethylamine.

Examples of suitable dehydrating reagents here include carbodiimides such as N,N'-diethyl-, N,N,'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N'-propyloxymethyl-polystyrene (PS-carbodiimide) or carbonyl compounds such as carbonyldiimidazole, or 1,2-oxazolium compounds such as 2-ethyl-5-phenyl-1,2-oxazolium-3-sulfate or 2-tert-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or bis(2-oxo-3-oxazolidinyl)phosphoryl chloride, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxybenzotriazole (HOBt) or benzotriazol-1-yloxytris(dimethylamino)phosphonium hexafluorophosphate (BOP), or benzotriazol-1-yloxytris(pyrrolidino)phosphonium hexafluorophosphate (PyBOP), or N-hydroxysuccinimide, or mixtures of these with bases.

Preferably the condensation is carried out with HATU, benzotriazol-1-yloxytris(pyrrolidino)phosphonium hexafluorophosphate (PyBOP) or with EDC in the presence of HOBt.

Alternatively, the reaction according to method [A] can take place via an activation of the acid in Formula (II) as an acid chloride or mixed anhydride The reaction of method [B] can be carried out by the methods described in A. Da Silva, M. De Almeida, V. De Souza, M. Couri, *Current Medicinal Chemistry*, 2003, 10, 21-39.

The hydrolysis of method [C] in general takes place in water or inert solvents or in mixtures of water and inert solvents, in the presence of a base, preferably in a temperature range from −30° C. to 100° C. under atmospheric pressure.

Examples of inert solvents are halogenated hydrocarbons such as dichloromethane or trichloromethane, hydrocarbon such as benzene, or other solvents such as nitromethane, dioxane, methanol, tetrahydrofuran, dimethylformamide or acetonitrile. It is also possible to use mixtures of the solvents. Of particular preference is dioxane, methanol, tetrahydrofuran or dimethylformamide.

Examples of bases include alkali metal hydroxides or alkali metal carbonates, such as sodium, potassium or lithium hydroxide, sodium or potassium carbonate or hydrogen carbonate.

The compounds of formula (III) and (V) are known or can be synthesized by known methods from the corresponding starting materials.

The compounds of formula (II) are known or can be prepared by reacting compounds of formula

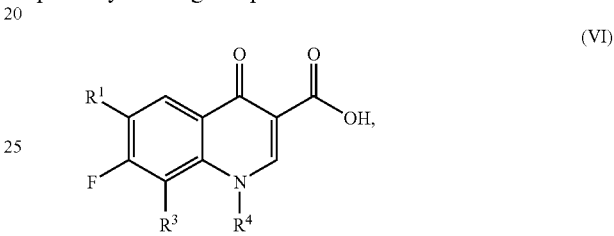

in which
R¹, R³ and R⁴ have the meaning indicated above,
with compounds of formula (V) according to method [B].

In the compounds of formula (VI), where appropriate, prior to the reaction with compounds of formula (V), the carboxylic acid group is activated by formation of a boron ester.

The compounds of formula (VI) are known or can be synthesized by known methods from the corresponding starting materials, as described for example in A. Da Silva, M. De Almeida, V. De Souza, M. Couri, *Current Medicinal Chemistry*, 2003, 10, 21-39.

The compounds of formula (IV) are known or can be prepared by reacting compounds of formula (VI) with compounds of formula (III) according to method [A].

The preparation of the compounds of the invention can be illustrated by the following synthesis scheme.

Synthesis scheme:

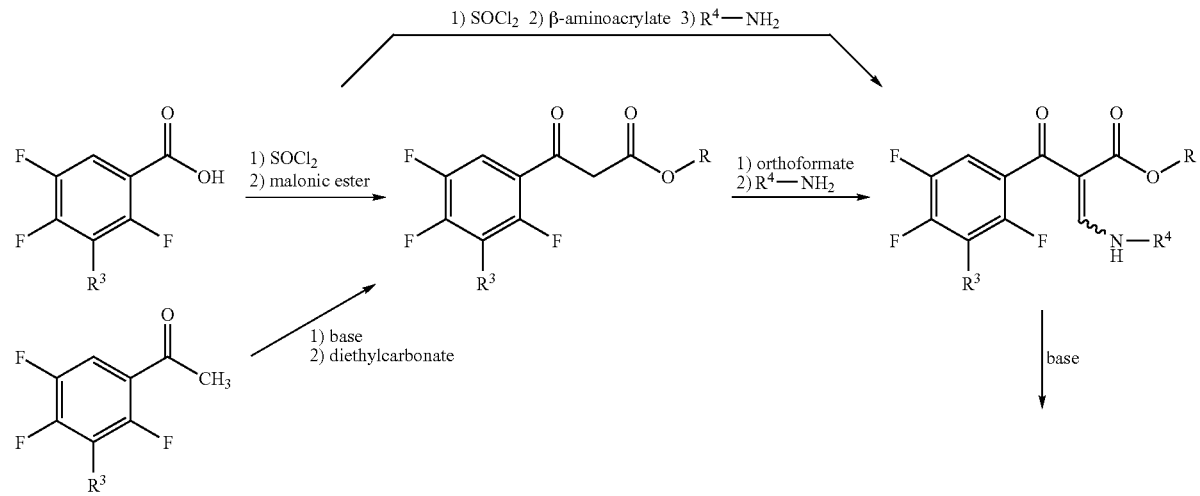

-continued

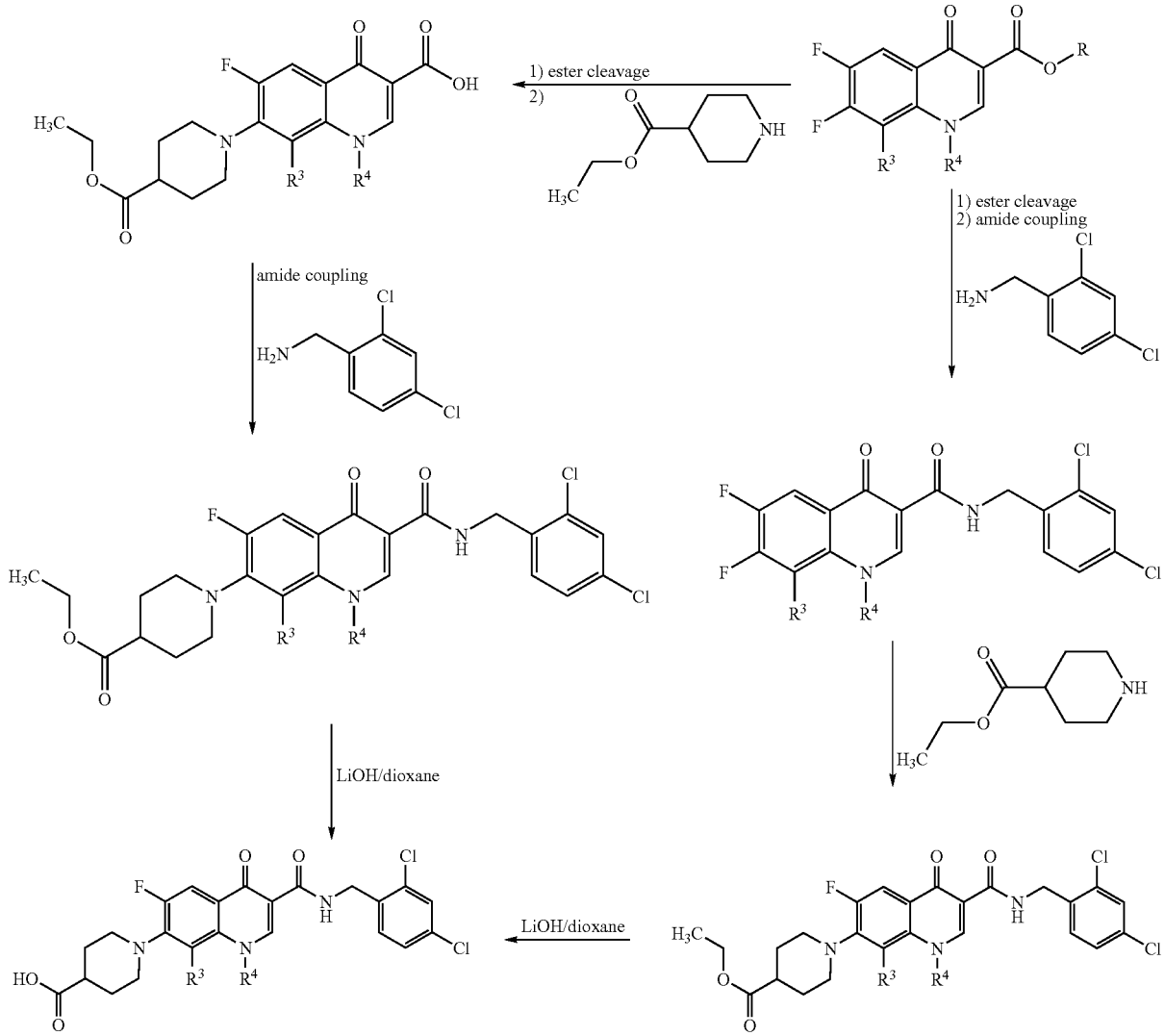

The compounds of the invention show a surprising range of effects which could not have been predicted. They show an antiviral activity against representatives of the group of herpes viridae (herpes viruses), in particular against cytomegaloviruses (CMV) and especially against the human cytomegalovirus (HCMV).

Areas of indication which may be mentioned by way of example are:

1) Treatment and prophylaxis of HCMV infections in AIDS patients (retinitis, pneumonitis, gastrointestinal infections).
2) Treatment and prophylaxis of cytomegalovirus infections in bone-marrow and organ transplant patients who develop often life-threatening HCMV pneumonitis or encephalitis, and gastrointestinal and systemic HCMV infections.
3) Treatment and prophylaxis of HCMV infections in neonates and infants.
4) Treatment of an acute HCMV infection in pregnant women.
5) Treatment of an HCMV infection in immunosuppressed patients associated with cancer and cancer therapy.
6) Treatment of HCMV-positive cancer patients with the aim of reducing HCMV-mediated tumour progression (cf. J. Cinatl, et al., *FEMS Microbiology Reviews* 2004, 28, 59-77).

The present invention further relates to the use of the compounds of the invention for the treatment and/or prophylaxis of diseases, in particular of infections with viruses, especially the aforementioned viruses, and of the infectious diseases caused thereby. A viral infection means hereinafter both an infection with a virus and a disease caused by an infection with a virus.

The present invention further relates to the use of the compounds of the invention for the treatment and/or prophylaxis of diseases, especially of the aforementioned diseases.

The present invention further relates to the use of the compounds of the invention for the production of a medicament for the treatment and/or prophylaxis of diseases, especially of the aforementioned diseases.

The compounds of the invention are preferably used for the production of medicaments which are suitable for the prophylaxis and/or treatment of infections with a representative of the group of herpes viridae, particularly a cytomegalovirus, in particular the human cytomegalovirus.

The present invention further relates to a method for the treatment and/or prophylaxis of diseases, especially the aforementioned diseases, using an antivirally effective amount of the compounds of the invention.

The present invention further relates to medicaments comprising at least one compound of the invention and at least one or more further active ingredients, in particular for the treatment and/or prophylaxis of the aforementioned diseases. Suitable active ingredients in combination which may be mentioned by way of example, and preferably, are: antiviral active ingredients such as valganciclovir, ganciclovir, aciclovir, cidofovir or foscarnet.

The compounds of the invention may act systemically and/or locally. They can for this purpose be administered in a suitable way, such as, for example, orally, parenterally, pulmonarily, nasally, sublingually, lingually, buccally, rectally, dermally, transdermally, conjunctivally, oticaly or topically, or as an implant or stent.

For these administration routes the compounds of the invention can be administered in suitable administration forms.

Suitable for oral administration are administration forms which function according to the prior art and deliver the compounds of the invention rapidly and/or in modified manner and which comprise the compounds of the invention in crystalline and/or amorphicized and/or dissolved form, such as, for example, tablets (uncoated or coated tablets, for example having coatings which are resistant to gastric juice or dissolve with a delay or are insoluble and control the release of the compound of the invention), tablets or films/wafers which disintegrate rapidly in the oral cavity, films/lyophilisates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous, or intraperitoneal). Administration forms suitable for parenteral administration are, inter alia, preparations for injection and infusion in the form of solutions, suspensions, emulsions, lyophilisates or sterile powders.

Examples suitable for the other administration routes are pharmaceutical forms for inhalation (inter alia powder inhalers, nebulizers), nasal drops, solutions, sprays; tablets, films/wafers or capsules, to be administered lingually, sublingually or buccally, suppositories, preparations for the ears and eyes, vaginal capsules, aqueous suspensions (lotions, shaking mixtures), lipophilic suspensions, ointments, creams, transdermal therapeutic systems, milk, pastes, foams, dusting powders, implants or stents.

The compounds of the invention can be converted into the stated administration forms. This can take place in a manner known per se by mixing with inert, non-toxic, pharmaceutically acceptable excipients. These excipients include, inter alia, carriers (for example microcrystalline cellulose, lactose, mannitol), solvents (for example liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (for example antioxidants such as ascorbic acid), colors (for example inorganic pigments such as iron oxides) or flavor- and/or odor-corrigents.

The present invention further relates to medicaments which comprise at least one compound of the invention, usually together with one or more inert, non-toxic, pharmaceutically acceptable excipients, and to the use thereof for the aforementioned purposes.

It has generally proved advantageous to administer on intravenous administration amounts of about 0.001 to 10 mg/kg, preferably about 0.01 to 5 mg/kg, of body weight to achieve effective results, and the dosage on oral administration is about 0.01 to 25 mg/kg, preferably 0.1 to 10 mg/kg, of body weight.

It may nevertheless be necessary where appropriate to deviate from the amounts mentioned, specifically as a function of the body weight, administration route, individual response to the active ingredient, type of preparation and time or interval over which administration takes place. Thus it may be sufficient in some cases to make do with less than the aforementioned minimum amount, whereas in other cases the upper limit mentioned must be exceeded. It may in the event of an administration of larger amounts be advisable to divide these into a plurality of individual doses over the day.

The percentage data in the following tests and examples are percentages by weight unless otherwise indicated; parts are parts by weight. Solvent ratios, dilution ratios and concentration data of liquid/liquid solutions are in each case based on volume. The percentage data of the yields of the example compounds are on a molar basis.

DETAILED DESCRIPTION OF PREFERRED EMBODIMENTS

A. Examples

| Abbreviations: | |
|---|---|
| BOC | tert-butoxycarbonyl |
| CDCl$_3$ | Deuterochloroform |
| DCI | direct chemical ionization (in MS) |
| DIEA | N,N-diisopropylethylamine |
| DMSO | Dimethylsulfoxide |
| DMF | N,N-dimethylformamide |
| EDC | N-(3-dimethylaminoisopropyl)-N'-ethylcarbodiimide hydrochloride |
| EI | electron impact ionization (in MS) |
| ESI | electrospray ionization (in MS) |
| h | Hour |
| HPLC | high pressure, high performance liquid chromatography |
| HV | high vacuum |
| LC-MS | coupled liquid chromatography-mass spectroscopy |
| LDA | lithium diisopropylamide |
| min | Minutes |
| MS | mass spectroscopy |
| MTBE | methyl tert-butyl ether |
| NMR | nuclear magnetic resonance spectroscopy |
| Pd—C | palladium on carbon |
| PyBOP | 1-benzotriazolyloxytripyrrolidinophosphonium hexafluorophosphate |
| RP-HPLC | reverse phase HPLC |
| RT | room temperature |
| R$_t$ | retention time (in HPLC) |
| TFA | trifluoroacetic acid |
| THF | Tetrahydrofuran |

General LC-MS and HPLC Methods:

Method 1 (LC-MS): Instrument: Micromass Quattro LCZ with HPLC Agilent series 1100; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 208-400 nm.

Method 2 (LC-MS): MS instrument type: Micromass ZQ; HPLC instrument type: Waters Alliance 2795; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 m/min, 2.5 min/3.0 min/4.5 min 2 ml/min; oven: 50° C.; UV detection: 210 nm.

Method 3 (LC-MS): MS instrument type: Micromass ZQ; HPLC instrument type: HP 1100 series; UV DAD; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 4 (LC-MS): Instrument: Micromass Platform LCZ with HPLC Agilent series 1100; column: Thermo Hypersil GOLD 3μ 20 mm×4 mm; eluent A: 1 l of water+0.5 ml of 50% formic acid, eluent B: 1 l of acetonitrile+0.5 ml of 50% formic acid; gradient: 0.0 min 100% A→0.2 min 100% A→2.9 min 30% A→3.1 min 10% A→5.5 min 10% A; oven: 50° C.; flow rate: 0.8 ml/min; UV detection: 210 nm.

Method 5 (preparative HPLC, formic acid): column: Grom-Sil 120 ODS-4HE, 10 μm, SNr. 3331, 250 mm×30 mm. Eluent A: formic acid 0.1% in water, eluent B: acetonitrile; flow rate: 50 ml/min. program: 0-3 min: 10% B; 3-27 min: gradient to 95% B; 27-34 min: 95% B; 34.01-38 min: 10% B.

Method 6 (preparative HPLC, hydrochloric acid): column: Grom-Sil 120 ODS-4HE, 10 μm, SNr. 3331, 250 mm×30 mm. Eluent A: hydrochloric acid 0.1% in water, eluent B: acetonitrile; flow rate: 50 ml/min. program: 0-2 min 10% B, 3-43 min: gradient to 100% B, 43.01-45 min: 100% B.

Method 7 (analytical HPLC): Instrument: HP 1100 with DAD detection; column: Kromasil 100 RP-18, 60 mm×2.1 mm, 3.5 μm; eluent A: 5 ml of perchloric acid (70%)/1 of water, eluent B: acetonitrile; gradient: 0 min 2% B, 0.5 min 2% B, 4.5 min 90% B, 9 min 90% B, 9.2 min 2% B, 10 min 2% B; flow rate: 0.75 ml/min; column temperature: 30° C.; UV detection: 210 nm.

Method 8 (analytical HPLC): Instrument: HP 1100 with DAD detection; column: Kromasil 100 RP-18, 60 mm×2.1 mm, 3.5 μm; eluent A: 5 ml of perchloric acid (70%)/1 of water, eluent B: acetonitrile; gradient: 0 min 2% B, 0.5 min 2% B, 4.5 min 90% B, 6.5 min 90% B, 6.7 min 2% B, 7.5 min 2% B; flow rate: 0.75 ml/min; column temperature: 30° C.; UV detection: 210 nm.

Starting Compounds

Example 1A

2-Bromo-4-chlorobenzonitrile

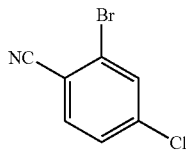

588 mg (2.5 mmol) of 2-bromo-4-chlorobenzoic acid and 300 mg of urea are dissolved in dichloromethane/methanol and concentrated onto 364 mg of alumina (neutral) on a rotary evaporator. The residue is microwaved at 150° C. for a total of 60 min. After cooling, the residue is stirred with ethyl acetate and water, filtered, and the aqueous phase is separated. The organic phase is washed with a sodium hydrogen carbonate solution, dried over sodium sulfate, concentrated on a rotary evaporator and then dried under high vacuum. The product (383 mg, 80% pure, 57% of theory.) is reacted further without additional purification.

1H NMR (300 MHz, CDCl$_3$): δ=7.72 (d, 1H), 7.60 (d, 1H), 7.42 (dd, 1H).

Example 2A

2-Chloro-4-(trifluoromethoxy)phenyl trifluoromethylsulfonate

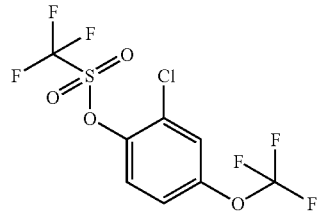

4.00 g of 2-chloro-4-trifluoromethoxyphenol in 50 ml of toluene and 50 ml of a 30% aqueous potassium phosphate solution in water are provided at 0° C., 3.82 ml of trifluoromethanesulfonic anhydride are added slowly and the mixture is stirred at RT for 1.5 h. The aqueous phase is separated and the organic phase is washed with water, dried over sodium sulfate and concentrated. The crude product (6.2 g) is reacted further to Example 3A without purification.

Example 3A

2-Chloro-4-trifluoromethoxybenzonitrile

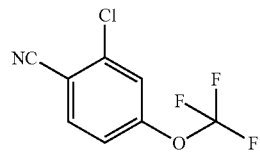

3.00 g of the compound of Example 2A are dissolved in 12 ml of degassed DMF with 2.04 g of zinc cyanide and 1.00 g of tetrakis(triphenylphosphine)palladium and the solution is heated under argon at 120° C. for 2 h. After cooling, the reaction mixture is diluted with ethyl acetate and extracted by shaking twice with a saturated sodium hydrogen carbonate solution and then with a saturated sodium chloride solution. The organic phase is dried over sodium sulfate and concentrated. The residue is purified by silica gel chromatography (cyclohexane/ethyl acetate 10:1). 880 mg (44% of theory) of the title compound are obtained.

1H NMR (300 MHz, DMSO-d$_6$): δ=7.62 (dd, 1H), 7.95 (d, 1H), 8.18 (d, 1H).

Example 4A

2-Methyl-4-(trifluoromethoxy)benzamide

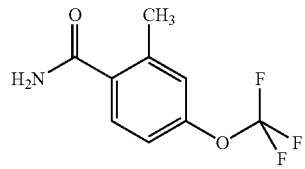

795 mg (3.61 mmol) of 2-methyl-4-(trifluoromethoxy) benzoic acid are heated under reflux with 4 ml (54.8 mmol) of thionyl chloride and one drop of DMF for 30 minutes. After cooling, the reaction solution is introduced slowly dropwise into an ice-cooled concentrated aqueous ammonia solution. The resulting precipitate is collected by suction filtration, taken up in 30 ml of water and stirred at 60° C. for 1 h. The mixture is allowed to cool and the solid is collected by filtration and dried under vacuum. Yield 562 mg (71% of theory).

LC-MS (method 2): $R_t$=1.61 min.

MS (ESI⁺): m/z=220 (M+H)⁺

1H NMR (400 MHz, DMSO-$d_6$): δ=7.79 (bs, 1H), 7.42-7.50 (m, 2H), 7.19-7.28 (m, 2H), 2.39 (s, 3H).

Example 5A

2-Methyl-4-(trifluoromethoxy)benzylamine

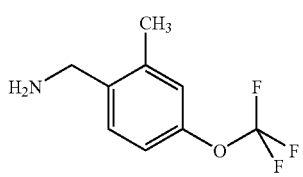

18.8 ml (18.8 mmol) of borane-THF complex (1M) are provided under argon with ice cooling. A solution of 823 mg (3.76 mmol) of 2-methyl-4-(trifluoromethoxy)benzamide (Example 4A) in 80 ml of THF is added dropwise and then the mixture is stirred under reflux for 8 h. With ice cooling, 80 ml of 1N hydrochloric acid are added dropwise (until the evolution of gas comes to an end) and the mixture is heated under reflux for 1 h. The reaction mixture is then rendered alkaline with a 1N sodium hydroxide solution and extracted three times with dichloromethane, the combined organic phases are dried over sodium sulfate and the solvent is removed under vacuum. This gives an oil which is reacted further without further purification. Yield: 732 mg (95% of theory).

LC-MS (method 3): $R_t$=1.41 min.

MS (ESI⁺): m/z=206 (M+H)⁺

$^1$H NMR (400 MHz, CDCl$_3$): δ=7.32-7.40 (m, 1H), 6.99-7.11 (m, 2H), 3.95-4.01 (m, 2H), 2.40 (s, 3H).

Adding excess HCl in dioxane (4N) and removing the volatile components on a rotary evaporator gives the corresponding hydrochloride.

Example 6A

2-Bromo-4-chlorobenzylamine

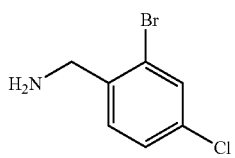

13.9 ml (13.9 mmol) of borane-THF complex (1 M) are provided with ice cooling. Slowly a solution of 604 mg (2.8 mmol) of 2-bromo-4-chlorobenzonitrile (Example 1A) in 60 ml of THF is added. Thereafter the reaction mixture is heated under reflux for 1 h, cooled, and 20 ml of 1N hydrochloric acid are added dropwise with ice cooling. For the work up, the solution is rendered alkaline with a 1N sodium hydroxide solution and extracted with dichloromethane. The organic phase is dried over sodium sulfate and concentrated on a rotary evaporator. The crude product (450 mg, about 73% pure) is reacted further without purification.

$^1$H NMR (300 MHz, CDCl$_3$): δ=3.89 (s, 2H), 7.35-7.45 (m [ABM], 2H), 7.55 (d, 1H).

Example 7A

2-Chloro-4-trifluoromethoxybenzylamine hydrochloride

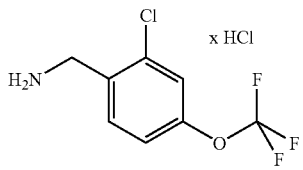

The preparation takes place in analogy to Example 6A from the compound of Example 3A with a subsequent treatment with 4N hydrochloric acid in dioxane and removal of the volatile components on a rotary evaporator.

$^1$H NMR (300 MHz, DMSO-$d_6$): δ=4.15 (s, 2H), 7.52 (d, 1H), 7.70 (s, 1H), 7.78 (d, 1H), 8.56 (bs, 3H).

Example 8A 2,4-Dichloro-6-methylbenzylamine hydrochloride

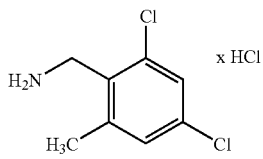

The preparation takes place in analogy to Example 6A from 2,4-dichloro-6-methylbenzonitrile with a subsequent treatment with 4N hydrochloric acid in dioxane and removal of the volatile components on a rotary evaporator.

$^1$H NMR (300 MHz, DMSO-$d_6$): δ=2.5 (s, 3H), 4.10 (s, 2H), 7.40 (s, 1H), 7.60 (s, 1H), 8.40 (bs, 3H).

LC-MS (method 4): $R_t$=2.44 min, MS (ES+)=190 (M+H)⁺.

Example 9A

2-Methyl-4-trifluoromethyl-benzylamine-hydrochloride

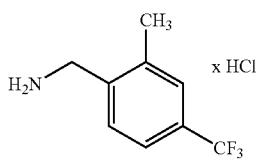

The preparation takes place in analogy to Example 6A from 2-methyl-4-trifluoromethylbenzonitrile with a subsequent treatment with 4N hydrochloric acid in dioxane and removal of the volatile components on a rotary evaporator.

$^1$H NMR (300 MHz, DMSO-d$_6$): δ=2.43 (s, 3H), 4.09 (s, 2H), 7.63 (s, 3H), 8.56 (br. s, 3H).

Example 10A (all-cis)-N-Benzyl-3,5-dimethyl-4-hydroxypiperidine

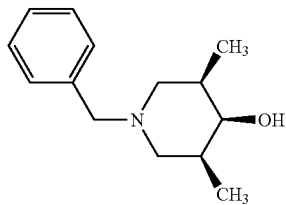

200 mg (0.60 mmol) of the TFA salt of N-benzyl-3,5-dimethylpiperidin-4-one (for preparation see: Journal of Medicinal Chemistry (1964), 7 (6), 726-728) are provided in 2 ml of ethanol at RT, 46 mg (1.21 mmol) of sodium borohydride are added and the mixture is stirred overnight. 2 ml of water are added and the mixture is extracted by shaking between ethyl acetate and a saturated sodium chloride solution. The aqueous phase is again extracted with ethyl acetate, and the combined organic phases are dried over sodium sulfate. The removal of the solvent on a rotary evaporator gives 130 mg (98% of theory) of the title compound, which is reacted further directly.

Example 11A (all-cis)-3,5-Dimethyl-4-hydroxypiperidine hydrochloride

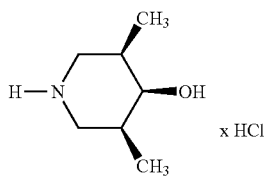

130 mg of the compound of Example 10A are hydrogenated using 10% Pd on carbon as a catalyst in 10 ml of methanol and 0.5 ml of a 4M solution of hydrogen chloride in dioxane under atmospheric pressure for 24 h. The catalyst is filtered off and the filtrate is freed from the solvents under vacuum. The residue is dried under high vacuum. This gives 98 mg (quantitative) of the title compound, which is used without further purification.

MS (DCI (NH$_3$)): m/z=147 (27) [M+NH$_4$]$^+$, 130 (100) [M+H]$^+$.

Example 12A

Ethyl (4-hydroxypiperidin-4-yl)acetate hydrochloride

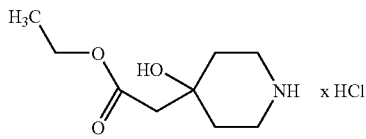

3.01 ml (6.02 mmol) of a 2M solution of LDA in THF are diluted in 7 ml of THF and cooled to −78° C. 540 μl (5.52 mmol) of ethyl acetate are added and the solution is stirred at −78° C. for 30 min. A solution of 1.00 g (5.01 mmol) of N-tert-butoxycarbonylpiperidin-4-one in 10 ml of THF is added dropwise. The mixture is stirred at −78° C. for a further 1 h and then warmed slowly to RT overnight. A saturated ammonium chloride solution is added and the product is extracted with dichloromethane. The removal of the solvent gives the ethyl (N-tert-butoxycarbonyl-4-hydroxypiperidin-4-yl)acetate. This crude product is chromatographed by HPLC (method 6), whereby the tert-butoxycarbonyl protecting group is cleaved by the hydrochloric acid in the eluent. 478 mg (42% of theory) of the title compound are obtained.

$^1$H NMR (400 MHz, DMSO-d$_6$): δ=1.20 (t, J=7.1 Hz, 3H), 1.69-1.86 (m, 4H), 2.48 (s, 2H), 2.96-3.18 (m, 4H), 4.07 (q, J=7.1 Hz, 2H), 5.05 (br. s, 1H).

Example 13A

3-Oxo-2,8-diazaspiro[4,5]decane hydrochloride

The title compound is obtained with quantitative yield by treating 310 mg (1.22 mmol) of 8-tert-butoxycarbonyl-3-oxo-2,8-diazaspiro[4,5]decane (for preparation see: Journal of Medicinal Chemistry (1995), 38(19), 3772-3780) with 8 ml of a 4M solution of hydrogen chloride in dioxane at RT for 2 h and then removing the volatile components on a rotary evaporator and under high vacuum.

MS (ES+): m/z=155 [M+H]$^+$.

$^1$H NMR (400 MHz, DMSO-d$_6$): δ=1.71 (t, J=7.1 Hz, 3H), 2.13 (s, 2H), 2.95-3.11 (m, 4H), 3.09 (s, 2H), 7.60 (br. s, 1H), 8.78 (br. s, 2H).

Example 14A

8-Benzyl-2-oxa-4,8-diazaspiro[4,5]decan-3-one

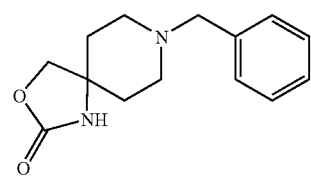

1.04 g (4.72 mmol) of 4-amino-1-benzyl-4-hydroxymethylpiperidine (for preparation see: Eur. J. Med. Chim. Ther. (1974) 9, 424-433) are suspended in 16 ml of dichloromethane and 842 mg (5.2 mmol) of carbonyldiimidazole are added. As the reaction progresses, a solution forms, which following complete reaction is diluted with dichloromethane and washed first with water, then with a 5 percent sodium bicarbonate solution and once again with water. The organic phase is dried over sodium sulfate and freed from the solvent on a rotary evaporator. 1.04 g of the title compound are obtained as a crude product, which is reacted further as it is.

LC-MS (method 4): R$_t$=1.80 min, MS (ES+): m/z=247 (M+H)$^+$ $^1$H NMR (400 MHz, CDCl$_3$): δ=1.74-1.84 (m, 4H), 2.40 (br.s, 4H), 3.50 (s, 2H), 4.12 (s, 2H), 5.90 (br.s, 1H), 7.22-7.35 (m, 5H).

Example 15A

2-Oxa-4,8-diazaspiro[4,5]decan-3-one

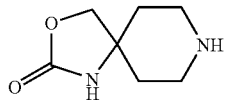

500 mg (1.61 mmol) of the compound of Example 14A are hydrogenated using 10 mg of Pd (10% on carbon) in methanol and 100 μl of 4N hydrogen chloride in dioxane under atmospheric pressure at RT overnight. The catalyst is filtered off and the filtrate is freed from the solvent on a rotary evaporator. The free base cannot be purified by extraction between ethyl acetate and a sodium bicarbonate solution. Therefore the aqueous phase is concentrated on a rotary evaporator and dried and the residue is stirred with methanol. The salts are largely removed by filtration. Removal of the solvent from the filtrate gives 360 mg of crude product, which is used without further purification.

MS (DCI (NH$_3$)): M/Z=174 (M+NH$_4$)$^+$, 157 (M+H)$^+$.

$^1$H NMR (400 MHz, MeOD): δ=1.68-1.80 (m, 4H), 2.73 (m, 2H), 2.90 (m, 2H), 4.19 (s, 2H).

Example 16A

Ethyl (S)-(1-tert-butoxycarbonylpiperidin-3-yl)acetate

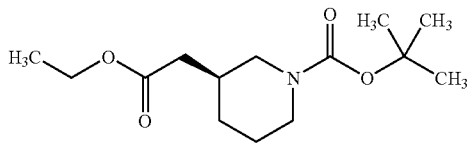

1 g (5.84 mmol) of racemic ethyl piperidin-3-ylacetate are provided in dichloromethane and 1.4 g (6.42 mmol) of di-tert-butyl dicarbonate are added. The solution is stirred at RT until the evolution of gas comes to an end, and freed from the solvent on a rotary evaporator. The two enantiomers are separated by means of chiral HPLC (Daicel Chirapak AD-H, 5 μm, 250 mm×20 mm, eluent isohexane/2-propanol 95:5). The product eluted first (R$_t$=5.10 min) is the (S)-enantiomer (Example 16A) (311 mg, 20% of theory). The product eluted later (R$_t$=5.34 min) is the (R)-enantiomer (Example 17A) (290 mg, 18% of theory). The absolute stereochemistry was assigned subsequently through the X-ray structure of Example 73.

Example 17A

Ethyl (R)-(1-tert-butoxycarbonylpiperidin-3-yl)acetate

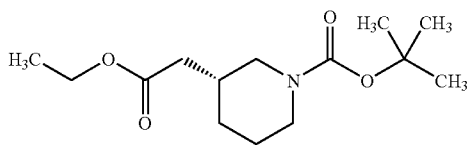

Preparation: see under Example 16A.

Example 18A

Ethyl (S)-piperidin-3-ylacetate hydrotrifluoroacetate

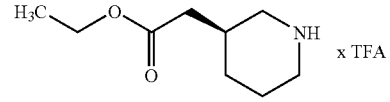

280 mg (1.03 mmol) of ethyl (S)-(1-tert-butoxycarbonylpiperidin-3-yl)acetate (Example 16A) are stirred with 2 ml of dichloromethane and 2 ml of trifluoroacetic acid at RT for 1 h. The volatile components are removed on a rotary evaporator and the residue is dried under high vacuum. The resulting oil (290 mg, 99% of theory) is reacted further as it is.

MS (ES+): m/z=172 [M+H]$^+$.

$^1$H NMR (400 MHz, CDCl$_3$): δ=1.28 (t, 3H), 1.30 (m, 1H), 1.80-2.00 (m, 3H), 2.28-2.35 (m, 3H), 2.70 (br.q, 1H), 2.87 (br.q, 1H), 3.42 (d, 1H), 3.51 (d, 1H), 4.13 (q, 2H), 8.50 (br s, 1H), 9.10 (br s, 1H).

Example 19A

Ethyl (R)-piperidin-3-ylacetate hydrotrifluoroacetate

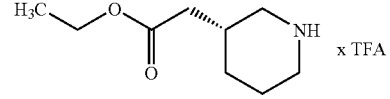

290 mg (1.07 mmol) of ethyl (R)-(1-tert-butoxycarbonylpiperidin-3-yl)acetate (Example 17A) are stirred with 2 ml of dichloromethane and 2 ml of trifluoroacetic acid at RT for 1 h. The volatile components are removed on a rotary evaporator and the residue is dried under high vacuum. The resulting oil (301 mg, 99% of theory) is reacted further as it is.

MS (ES+): m/z=172 [M+H]$^+$.

$^1$H NMR (400 MHz, CDCl$_3$): δ=1.28 (t, 3H), 1.30 (m, 1H), 1.80-2.00 (m, 3H), 2.32 (br s, 3H), 2.70 (m, 1H), 2.87 (m, 1H), 3.42 (d, 1H), 3.50 (d, 1H), 4.13 (q, 2H), 8.72 (br s, 1H), 9.30 (br s, 1H).

Example 20A

Ethyl 3-[(2,2,2-trifluoroethyl)amino]-2-(2,4,5-trifluoro-3-methoxybenzoyl)acrylate (E+Z)

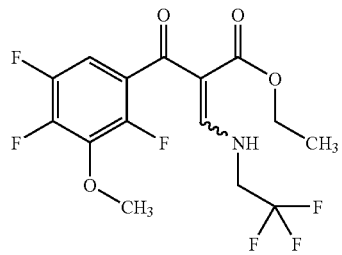

2.00 g (5.79 mmol) of ethyl 3-oxo-3-(2,4,5-trifluoro-3-methoxyphenyl)propanoate (for preparation see Journal of Medicinal Chemistry (1995), 38 (22), 4478-87) are stirred under reflux in 3.8 ml (4.14 g, 40.55 mmol) of acetic anhydride and 4.82 ml (4.29 g, 28.96 mmol) of triethyl orthoformate for 2 h. The solvent is then removed completely on a rotary evaporator and the residue is dissolved in 10 ml of ethanol. 1.03 g (10.43 mmol) of 2,2,2-trifluoro-1-aminoethane are added dropwise to the ice-cooled solution. The mixture is brought to room temperature and stirred at that temperature overnight. For the work up, the solvent is removed and the residue is reacted further as a crude product without purification steps (yield assumed to be quantitive).

LC-MS (method 2): $R_t$=2.37 min, MS (ES+)=386 (M+H)$^+$.

The following Examples 21A to 25A are prepared in analogy to Example 20A from the corresponding amines.

| Example No. | Structure | Analytical data LC-MS (method)/measurement values |
|---|---|---|
| 21A (R)-enantiomer | 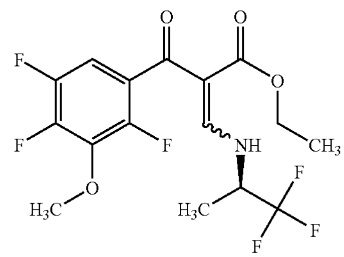 | LC-MS (method 1): $R_t$ = 2.46 min MS (ES+): m/z = 400 (M + H)$^+$ |
| 22A racemic | 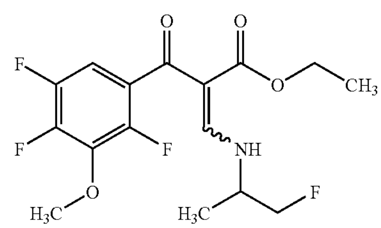 | LC-MS (method 2): $R_t$ = 2.28 min MS (ES+): m/z = 364 (M + H)$^+$ |
| 23A | 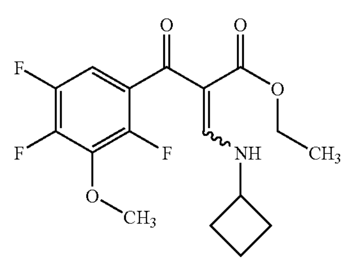 | LC-MS (method 3): $R_t$ = 2.72 min MS (ES+): m/z = 358 (M + H)$^+$ |
| 24A | 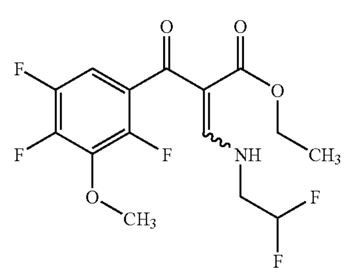 | LC-MS (method 2): $R_t$ = 2.22 min MS (ES+): m/z = 368 (M + H)$^+$ |
| 25A (1S, 2R)-enantiomer | 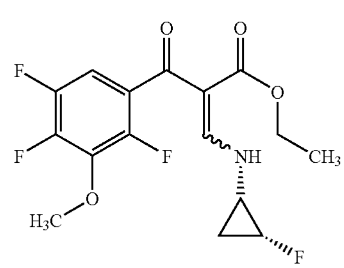 | LC-MS (method 1): $R_t$ = 2.40 min MS (ES+): m/z = 382 (M + H)$^+$ |

Example 26A

Ethyl 6,7-difluoro-8-methoxy-4-oxo-1-(2,2,2-trifluoroethyl)-1,4-dihydroquinoline-3-carboxylate

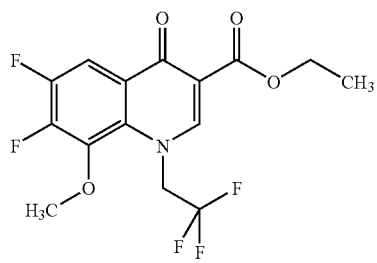

Under an argon atmosphere and with ice cooling 0.32 g (8.11 mmol) of 60% sodium hydride are provided in 5 ml of tetrahydrofuran, and a solution of 2.23 g (5.79 mmol) of the compound of Example 20A in 15 ml of tetrahydrofuran is slowly added dropwise. The mixture is subsequently warmed to room temperature, stirred at that temperature for 2 h and left to stand overnight. For the work up, 2 ml of acetic acid are added dropwise, the mixture is stirred for 5 min, diluted with ethyl acetate, washed several times with water and once with a saturated sodium hydrogen carbonate solution, the organic phase is dried over magnesium sulfate and filtered, and the solvent is removed completely on a rotary evaporator. The crude product is prepurified by column chromatography on silica gel 60 (eluent: dichloromethane/methanol 100/1→100/2). For fine purification one half of the crude product is purified by preparative HPLC (method 5) (0.83 g of pure product). The other half is recrystallised from acetonitrile (1.02 g). The overall yield is therefore 1.85 g (87% of theory).

HPLC (method 8): $R_t$=4.34 min

MS (DCI (NH$_3$))=366 (M+H)$^+$.

$^1$H NMR (300 MHz, CDCl$_3$): δ=1.41 (t, 3H), 4.15 (s, 3H), 4.41 (q, 2H), 5.23 (q, 2H), 8.11 (dd, 1H), 8.33 (s, 1H).

Examples 27A to 31A listed in the table below are prepared in analogy to Example 26A.

| Example No. | Structure | Starting Material Example No. | Analytical data LC-MS (method)/measurement values HPLC (method)/measurement values MS (method)/measurement values |
|---|---|---|---|
| 27A (R)-enantiomer | 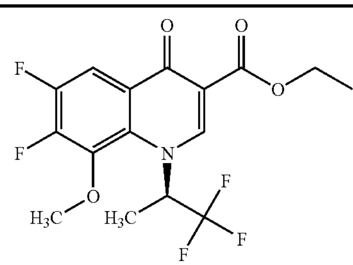 | 21A | LC-MS (method 1): $R_t$ = 2.22 min MS (ES+): m/z = 380 (M + H)$^+$ |
| 28A racemic | 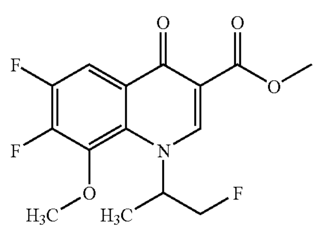 | 22A | HPLC (method 8): $R_t$ = 4.11 min MS (DCI (NH$_3$)): m/z = 344 (M + H)$^+$ |
| 29A | 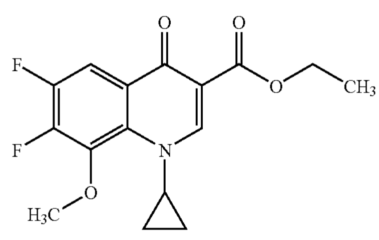 | 23A | LC-MS (method 3): $R_t$ = 2.33 min MS (ES+): m/z = 338 (M + H)$^+$ |
| 30A | 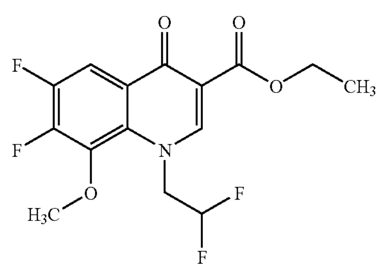 | 24A | LC-MS (method 2): $R_t$ = 1.83 min MS (ES+): m/z = 348 (M + H)$^+$ |

| Example No. | Structure | Starting Material Example No. | Analytical data LC-MS (method)/measurement values HPLC (method)/measurement values MS (method)/measurement values |
|---|---|---|---|
| 31A (1S,2R)-enantiomer | 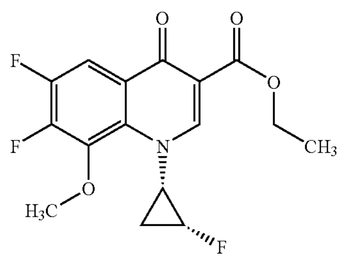 | 25A | LC-MS (method 2): $R_t$ = 1.76 min MS (ES+): m/z = 342 (M + H)$^+$ |

Example 32A

6,7-Difluoro-8-methoxy-4-oxo-1-(2,2,2-trifluoroethyl)-1,4-dihydroquinoline-3-carboxylic acid

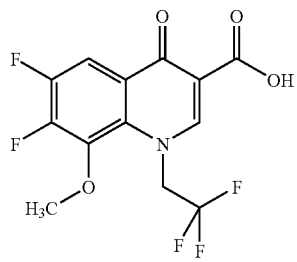

800 mg (2.19 mmol) of the compound of Example 26A are provided in a mixture of 25 ml of acetic acid-water-sulfuric acid 12:8:1 and stirred under reflux overnight. For the work up, the solvent is largely removed on a rotary evaporator, the residue is adjusted to a pH of 3, cautiously, with a saturated sodium hydrogen carbonate solution, with ice cooling, the suspension is diluted with water and the precipitate is collected by suction filtration. After drying of the filter residue under high vacuum, 575 mg of the title compound are obtained.

LC-MS (method 3): $R_t$=2.41 min, MS (ES+)=338 (M+H)$^+$.

$^1$H NMR (300 MHz, CDCl$_3$): δ=4.21 (s, 3H), 5.37 (q, 2H), 8.11 (dd, 1H), 8.62 (s, 1H), 14.05 (bs, 1H).

The following Examples 33A to 37A are prepared in analogy to Example 32A.

| Example No. | Structure | Starting Material | Analytical data LC-MS (method)/measurement values HPLC (method)/measurement values MS (method)/measurement values |
|---|---|---|---|
| 33A (R)-enantiomer | 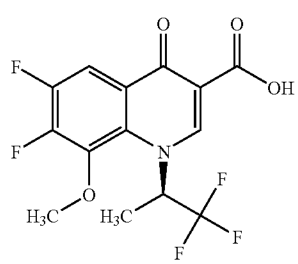 | 27A | LC-MS (method 3): $R_t$ = 2.47 min MS (ES+): m/z 352 (M + H)$^+$ |
| 34A racemic | 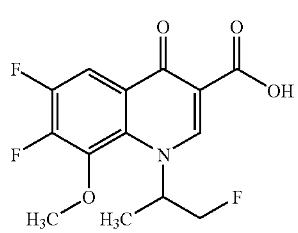 | 28A | HPLC (method 8): $R_t$ = 4.17 min MS (ESI+): m/z 316 (M + H)$^+$ |

| Example No. | Structure | Starting Material | Analytical data LC-MS (method)/measurement values HPLC (method)/measurement values MS (method)/measurement values |
|---|---|---|---|
| 35A | 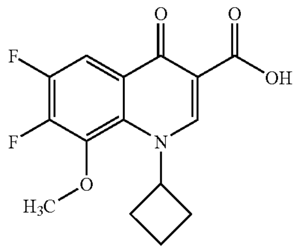 | 29A | LC-MS (method 3): $R_t$ = 2.35 min MS (ES+): m/z 310 (M + H)+ |
| 36A | 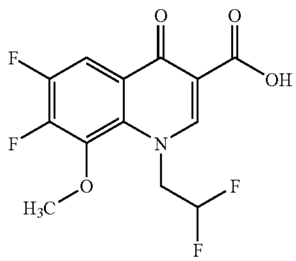 | 30A | HPLC (method 7): $R_t$ = 4.15 min MS (DCI (NH$_3$)): m/z 337 (M + NH$_4$)+ |
| 37A (1S,2R)-enantiomer | 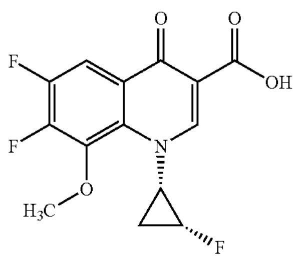 | 31A | LC-MS (method 2): $R_t$ = 1.84 min MS (ES+): m/z 314 (M + H)+ |

Example 38A

[6,7-Difluoro-8-methoxy-4-oxo-1-(2,2,2-trifluoroethyl)-1,4-dihydroquinolin-3-yl]carbonyl difluoroborate

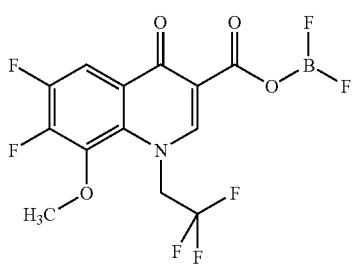

1.45 g (4.30 mmol) of the compound of Example 32A are provided in 10 ml of tetrahydrofuran, subsequently 6.81 ml (7.63 g, 53.75 mmol) of boron trifluoride-diethyl ether complex are added and the mixture is stirred overnight at 70° C. For the work up, the reaction mixture is cooled to room temperature and 50 ml of diethyl ether are added, the mixture is stirred for 20 min and the resulting precipitate is collected by suction filtration. Drying of the solid under high vacuum gives 1150 mg of the title compound, which is reacted further without purification.

HPLC (method 7): $R_t$=4.25 min,

MS (DCI (NH$_3$))=402 (M+NH$_4$)+.

$^1$H NMR (300 MHz, DMSO-d$_6$): δ=4.21 (s, 3H), 6.12 (q, 2H), 8.38 (dd, 1H), 9.66 (s, 1H).

The following Examples 39A to 43A are prepared in analogy to Example 38A.

| Example No. | Structure | Starting Material | Analytical data LC-MS (method)/measurement values |
|---|---|---|---|
| 39A (R)-enantiomer | 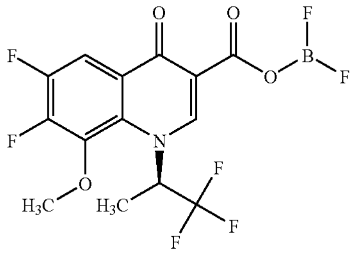 | 33A | LC-MS (method 2): $R_t$ = 1.98 min MS (ES+): m/z = 400 (M + H)$^+$ |
| 40A | 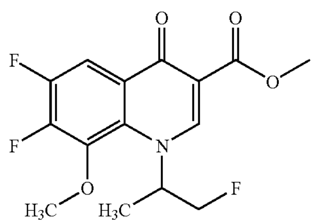 | 34A | LC-MS (method 1): $R_t$ = 1.96 min MS (ES+): m/z = 364 (M + H)$^+$ |
| 41A | 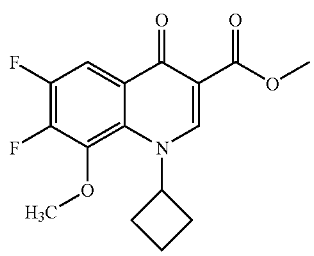 | 35A | LC-MS (method 1): $R_t$ = 1.92 min MS (ES+): m/z = 358 (M + H)$^+$ |
| 42A | 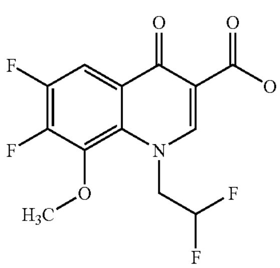 | 36A | LC-MS (method 3): $R_t$ = 2.09 min MS (ES+): m/z = 368 (M + H)$^+$ |
| 43A (1S,2R)-enantiomer | 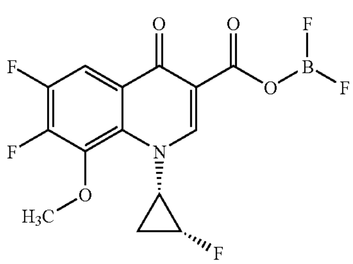 | 37A | LC-MS (method 2): $R_t$ = 1.74 min MS (ES+): m/z = 362 (M + H)$^+$ |

Example 44A

[6,7-Difluoro-1-{(1R,2S)-2-fluorocyclopropy-lamino}-8-methoxy-4-oxo-1,4-dihydroquinolin-3-yl]carbonyl difluoroborate

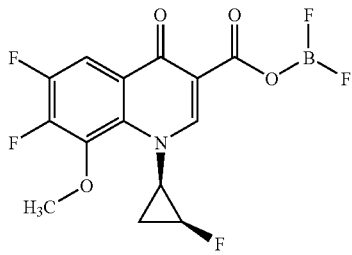

From 750 mg (2.39 mmol) of 6,7-difluoro-1-{(1R,2S)-2-fluorocyclopropylamino}-8-methoxy-4-oxo-1,4-dihydroquinoline-3-carboxylic acid (for preparation see WO 96/01262) and 4.08 g (29 mmol) of $BF_3$ etherate, in analogy to Example 38A, 582 mg of the title compound are obtained.

LC-MS (method 2): $R_t$=1.74 min

MS (ES+): m/z=362 (M+H)$^+$, $^1$H NMR (400 MHz, CDCl$_3$): δ=9.17 (s, 1H), 8.15 (t, J=8.5 Hz, 1H), 5.01 (dm, J=63 Hz, 1H), 4.43 (m, 1H), 4.29 (s, 3H), 2.00-1.75 (m, 3H).

Example 45A 8,9-Difluoro-3-methyl-7-oxo-2,3-dihydro-7H-[1,4]oxazino[2,3,4-ij]quinoline-6-carbonyl difluoroborate

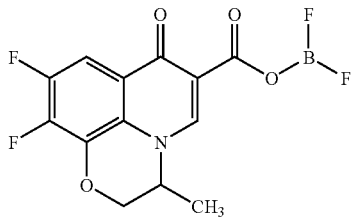

From 1.0 g of 8,9-difluoro-3-methyl-7-oxo-2,3-dihydro-7H-[1,4]oxazino[2,3,4-ij]quinoline-6-carboxylic acid (for preparation see Journal of Medicinal Chemistry 1992, 35 (4), 611) and 1.51 g (3 eq.) of $BF_3$ etherate, by the same method as described for Example 38A, 1.0 g (85% of theory) of the title compound is isolated.

MS (ESI pos): m/z=330 (M+H)$^+$.

1H NMR (400 MHz, DMSO-d$_6$): δ=9.64 (s, 1H), 8.15 (dd, J=7.5, 10.0 Hz, 1H), 5.32 (m, 1H), 4.82 (d, J=11.6 Hz, 1H), 4.57 (dd, J=11.5 Hz, 1.8 Hz, 1H), 1.56 (d, J=7.0 Hz, 3H).

Example 46A 7-(4-Ethoxycarbonylpiperidin-1-yl)-6-fluoro-1-(2-fluoroethyl)-8-methoxy-4-oxo-1,4-dihydroquinoline-3-carboxylic acid

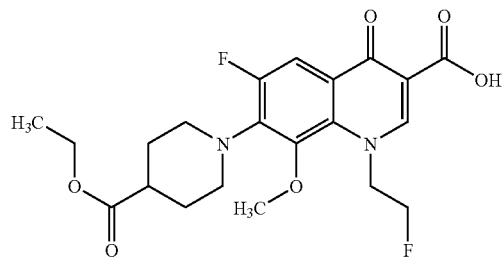

155 mg (0.38 mmol) of 6,7-difluoro-1-(2-fluoroethyl)-8-methoxy-4-oxo-1,4-dihydroquinolin-3-yl]-carbonyl difluoroborate (for preparation see EP0241206) and 120 mg (0.76 mmol, 2 eq.) of ethyl piperidine-4-carboxylate are stirred in 3 ml of acetonitrile at 50° C. for 3 h. The solvent is removed on a rotary evaporator and 0.56 ml of ethanol and 0.53 ml of triethylamine are added to the residue. This solution is heated at reflux for 2 h. The solvents are removed on a rotary evaporator and the residue is taken up in a little DMSO and separated by preparative HPLC (method 5). Concentration of the corresponding fractions on a rotary evaporator and drying under high vacuum give 100 mg (59% of theory) of the title compound.

LC-MS (method 2): $R_t$=2.30 min, MS (ES+): m/z=439 (M+H)$^+$.

$^1$H NMR (500 MHz, CDCl$_3$): δ=14.67 (s, 1H), 8.59 (s, 1H), 7.98 (d, J=12.1 Hz, 1H), 4.83 (dt, J=25.6, 4 Hz, 2H), 4.71 (dt, J=47 Hz, 4 Hz, 2H), 4.19 (q, J=7.1 Hz, 2H), 3.83 (s, 3H), 3.51 (br. d, J=12 Hz, 2H), 3.23 (br. t, J=12 Hz, 2H), 2.54 (m, 1H), 2.05 (br. d, J=10 Hz, 2H), 1.90 (m, 2H), 1.28 (t, J=7.1 Hz, 3H).

Example 47A 7-(4-Ethoxycarbonylpiperidin-1-yl)-6-fluoro-8-methoxy-4-oxo-1-(2,2,2-trifluoroethyl)-1,4-dihydroquinoline-3-carboxylic acid

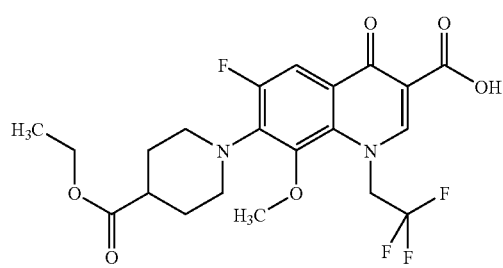

According to the same method as for Example 46A, from 800 mg (2.08 mmol) of [6,7-difluoro-8-methoxy-4-oxo-1-(2,2,2-trifluoroethyl)-1,4-dihydroquinolin-3-yl]carbonyl difluoroborate (Example 38A) and 653 mg (4.15 mmol) of ethyl piperidine-4-carboxylate, 625 mg (63% of theory) of the title compound are obtained.

HPLC (method 8): $R_t$=4.97 min.

MS (ES+): m/z=475 [M+H]$^+$.

$^1$H NMR (400 MHz, CDCl$_3$): δ=14.40 (s, 1H), 8.54 (s, 1H), 7.93 (d, J=12.1 Hz, 1H), 5.31 (q, J=7.9 Hz, 2H), 4.19 (q, J=7.1 Hz, 2H), 3.86 (s, 3H), 3.53 (br. d, J=12.5 Hz, 2H), 3.23 (br. t, J=12 Hz, 2H), 2.54 (m, 1H), 2.09-2.01 (m, 2H), 1.97-1.85 (m, 2H), 1.29 (t, J=7.1 Hz, 3H).

Alternative process for larger quantities: 15.5 g (40.3 mmol) of the compound of Example 38A and 12.66 g (80.52 mmol) of ethyl piperidine-4-carboxylate are stirred in 290 ml of acetonitrile at 50° C. overnight. The solvent is removed completely on a rotary evaporator and the residue is stirred under reflux with a mixture of 250 ml of ethanol and 125 ml of triethylamine for 1 h. The solvent is removed on a rotary evaporator and the residue is dissolved in methanol. This solution is stirred into 1000 ml of 1N hydrochloric acid. The precipitated product is collected by suction filtration and dried under high vacuum. This gives 19.1 g (74% of theory) of the title compound.

The following Examples 48A to 54A are prepared in analogy to the instructions of Example 46A. If no starting material is entered for the piperidine moiety, the substituted piperidine employed is commercially available.

| Example No. | Structure | Starting Materials | Analytical data LC-MS (method)/measurement values |
|---|---|---|---|
| 48A (R)-enantiomer | 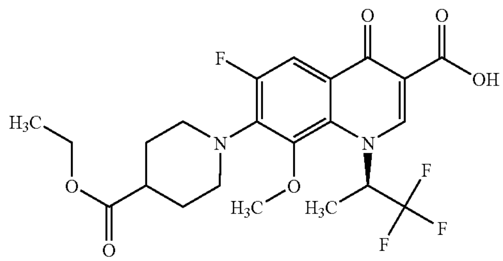 | 39A | LC-MS (method 3): R$_t$ = 2.92 min. MS (ES+): m/z = 489 (M + H)$^+$ |
| 49A racemic | 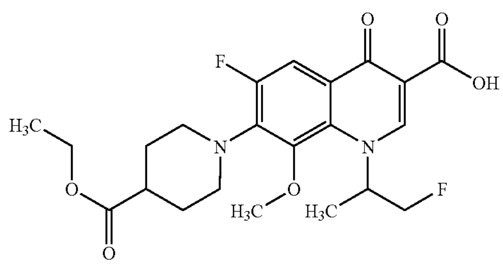 | 40A | LC-MS (method 1): R$_t$ = 2.57 min MS (ES+): m/z = 453 (M + H)$^+$ |
| 50A | 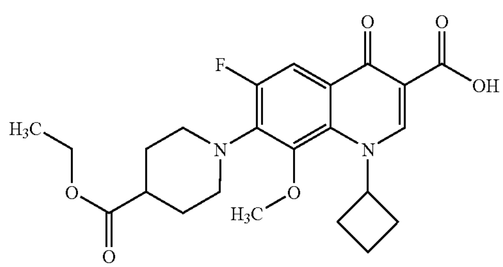 | 41A | LC-MS (method 1): R$_t$ = 2.71 min MS (ES+): m/z = 447 (M + H)$^+$ |
| 51A | 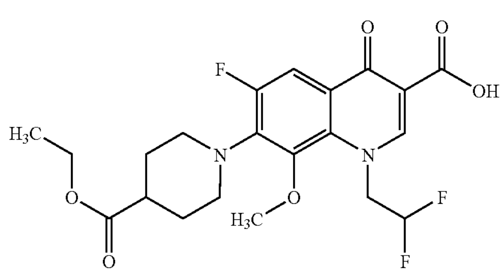 | 42A | LC-MS (method 3): R$_t$ = 2.69 MS (ES+): m/z = 457 (M + H)$^+$ |

| Example No. | Structure | Starting Materials | Analytical data LC-MS (method)/measurement values |
|---|---|---|---|
| 52A (1R,2S)-enantiomer | 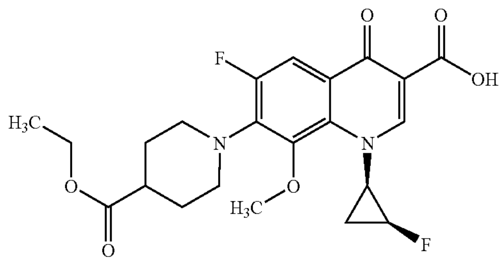 | 44A | LC-MS (method 3):<br>$R_t$ = 2.74 min<br>MS (ES+): m/z = 451 (M + H)$^+$ |
| 53A racemic | 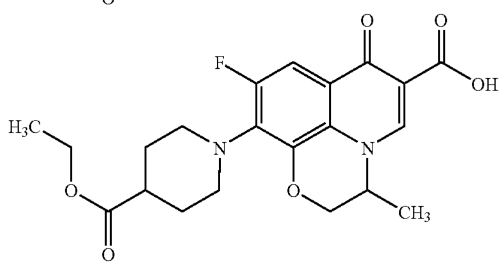 | 45A | LC-MS (method 1):<br>$R_t$ = 2.44 min<br>MS (ES+): m/z = 419 (M + H)$^+$ |
| 54A | 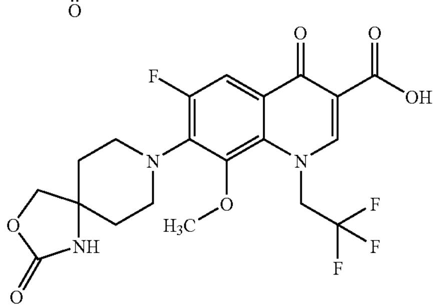 | 38A + 15A | LC-MS (method 1):<br>$R_t$ = 2.03 min<br>MS (ES+): m/z = 474 (M + H)$^+$ |

Example 55A

7-[(3S)-3-(2-Ethoxy-2-oxoethyl)piperidin-1-yl]-6-fluoro-8-methoxy-4-oxo-1-(2,2,2-trifluoroethyl)-1,4-dihydroquinoline-3-carboxylic acid

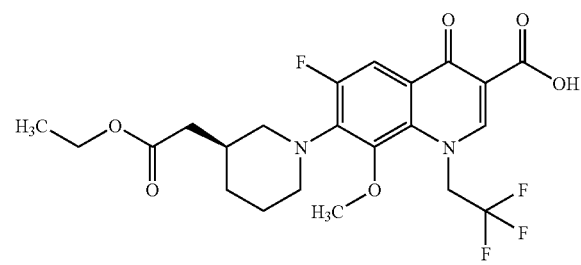

290 mg (1.05 mmol) of the compound of Example 18A (S-enantiomer) are provided in 8 ml of acetonitrile at RT, and 177 µl of N,N-diisopropylethylamine (1.1 eq.) and subsequently 356 mg (0.92 mmol) of the compound of Example 38A are added. The mixture is stirred at 50° C. After one hour, 80 µl of N,N-diisopropylethylamine (0.5 eq.) and after 2 hours a further 80 µl of N,N-diisopropylethylamine (0.5 eq.) are added. The mixture is left stirring at 50° C. overnight, then freed from the volatile components on a rotary evaporator. The residue is boiled with 1.4 ml of ethanol and 1.4 ml of triethylamine for 2 h and the solution is cooled to RT. Following the removal of the volatile components on a rotary evaporator, the residue is taken up in DMSO and separated by preparative HPLC (method 5). 243 mg (52% of theory) of the title compound are obtained.

LC-MS (method 2): $R_t$=2.65 min
MS (ES+): m/z=489 (M+H)$^+$
$^1$H NMR (400 MHz, CDCl$_3$): δ=14.41 (s, 1H), 8.52 (s, 1H), 7.92 (d, J=12 Hz, 1H), 5.31 (dq, J=2.5, 7.9 Hz, 2H), 4.14 (q, J=7.1 Hz, 2H), 3.84 (s, 3H), 3.50 (br. d, J=12.1 Hz, 2H), 3.23 (br. d, J=12.7 Hz, 2H), 3.14 (br. t, J=11 Hz, 1H), 2.90 (br. t, J~11 Hz, 1H), 2.30-2.20 (m, 3H), 1.96 (br. d, J~8 Hz, 1H), 1.85-1.70 (m, 2H), 1.26 (t, J=7.1 Hz, 3H).

Example 56A

7-[(3R)-3-(2-Ethoxy-2-oxoethyl)piperidin-1-yl]-6-fluoro-8-methoxy-4-oxo-1-(2,2,2-trifluoroethyl)-1,4-dihydroquinoline-3-carboxylic acid

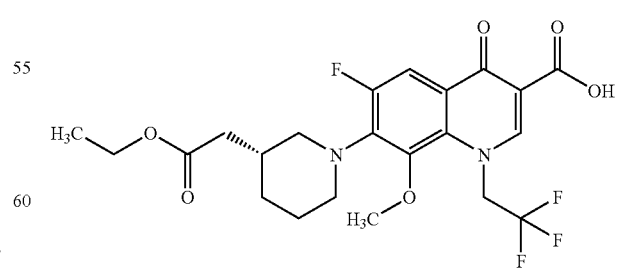

300 mg (1.05 mmol) of the compound of Example 19A (R-enantiomer) are provided in 8 ml of acetonitrile at RT, and 183 µl of N,N-diisopropylethylamine (1.1 eq.) and subsequently 368 mg (0.96 mmol) of the compound of Example 38A are added. The mixture is stirred at 50° C. After one hour, 83 µl of N,N-diisopropylethylamine (0.5 eq.) and after 2 hours a further 83 µl of N,N-diisopropylethylamine (0.5 eq.) are added. The mixture is left stirring at 50° C. overnight, then freed from the volatile components on a rotary evaporator. The residue is boiled with 1.4 ml of ethanol and 1.4 ml of triethylamine for 2 h and the solution is cooled to RT. Following the removal of the volatile components on a rotary evaporator, the residue is taken up in DMSO and separated by preparative HPLC (method 5). 243 mg (52% of theory) of the title compound are obtained.

LC-MS (method 2): $R_t$=2.65 min

MS (ES+): m/z=489 (M+H)$^+$ $^1$H NMR (400 MHz, CDCl$_3$): δ=14.44 (s, 1H), 8.53 (s, 1H), 7.92 (d, J=12 Hz, 1H), 5.31 (dq, J=2.5, 7.9 Hz, 2H), 4.14 (q, J=7.1 Hz, 2H), 3.84 (s, 3H), 3.50 (br. d, J=12.1 Hz, 2H), 3.23 (br. d, J=12.7 Hz, 2H), 3.14 (br. t, J=11 Hz, 1H), 2.90 (br. t, J~11 Hz, 1H), 2.30-2.20 (m, 3H), 1.96 (br. d, J~8 Hz, 1H), 1.85-1.70 (m, 2H), 1.26 (t, J=7.1 Hz, 3H).

Example 57A

7-[4-(2-Ethoxy-2-oxoethyl)piperidin-1-yl]-6-fluoro-8-methoxy-4-oxo-1-(2,2,2-trifluoroethyl)-1,4-dihydroquinoline-3-carboxylic acid

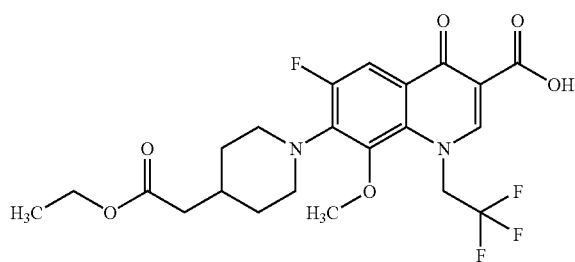

1100 mg (2.86 mmol) of 6,7-difluoro-8-methoxy-1-(2,2,2-trifluoroethyl)-4-oxo-1,4-dihydroquinolin-3-yl]carbonyl difluoroborate (Example 38A) and 979 mg (5.71 mmol, 2 eq.) of ethyl piperidin-4-ylacetate are stirred in 20.6 ml of acetonitrile at 50° C. for 3 h. The solvent is removed on a rotary evaporator and 14 ml of ethanol and 28 ml of triethylamine are added to the residue. This solution is heated at reflux for 1 h. The solvents are removed on a rotary evaporator and the residue is taken up in DMSO/acetonitrile and separated by preparative HPLC (method 5). Concentration of the corresponding fractions on a rotary evaporator and drying under high vacuum give 358 mg (26% of theory) of the title compound.

LC-MS (method 2): $R_t$=2.64 min

MS (ES+): m/z=489 (M+H)$^+$ $^1$H NMR (400 MHz, CDCl$_3$): δ=14.48 (s, 1H), 8.54 (s, 1H), 7.90 (d, 1H), 5.32 (q, 2H), 4.17 (q, 2H), 3.83 (s, 3H), 3.50 (br. d, 2H), 3.22 (br. d, J=12.7 Hz, 2H), 2.32 (d, 2H), 2.04 (m, 1H), 1.84 (br. d, 2H), 1.49 (dq, 2H), 1.28 (t, 3H).

Example 58A 7-(4-Aminocarbonylpiperidin-1-yl)-6-fluoro-8-methoxy-4-oxo-1-(2,2,2-trifluoroethyl)-1,4-dihydroquinoline-3-carboxylic acid

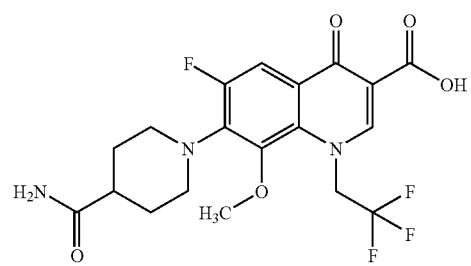

800 mg (2.08 mmol) of the compound of Example 38A and 533 mg of 4-aminocarbonylpiperidine (4.16 mmol) are stirred in 15 ml of acetonitrile at 50° C. overnight. The solvent is removed on a rotary evaporator and the residue is boiled with 20 ml of ethanol and 10 ml of triethylamine for 1 h. After cooling, the volatile components are removed on a rotary evaporator. The residue is stirred with acetonitrile and the solid is collected by filtration, washed with acetonitrile and dried under HV. 655 mg of the title compound (71% of theory) are obtained.

LC-MS (method 1): $R_t$=1.90 min

MS (ES+): m/z=446 (M+H)$^+$ $^1$H NMR (400 MHz, DMSO-d$_6$): δ=9.01 (s, 1H), 7.81 (d, J=12.2 Hz, 1H), 7.31 (s, 1H), 6.82 (s, 1H), 5.78 (q, J=8.7 Hz, 2H), 3.81 (s, 3H), 3.45 (br. d, J=12.4 Hz, 2H), 3.16 (br. t, J=12.2 Hz, 2H), 2.38-2.27 (m, 1H), 1.83-1.67 (m, 4H).

Example 59A

1-Cyclopropyl-7-(4-ethoxycarbonylpiperidin-1-yl)-6-fluoro-8-methoxy-4-oxo-1,4-dihydroquinoline-3-carboxylic acid

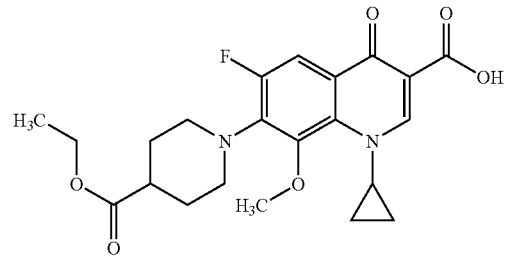

A solution of 275 mg (1.75 mmol) of ethyl piperidine-4-carboxylate and 250 mg (0.73 mmol) of (T-4)-(1-cyclopropyl-6,7-difluoro-1,4-dihydro-8-methoxy-4-oxo-3-quinolinecarboxylato-O3,O4)boron difluoride (for preparation see: Journal of Medicinal Chemistry (1995), 38(22), 4478-87) in 5 ml of acetonitrile is stirred at 50° C. overnight. The solvent is removed on a rotary evaporator and the residue is taken up in 5 ml of triethylamine and 50 ml of ethanol and heated at reflux for 4 h. After cooling, the solution is concentrated on a rotary evaporator and the product is purified by RP-HPLC (method 6). 214 mg (68% of theory) of the title compound are obtained.

$^1$H NMR (300 MHz, DMSO-$d_6$): δ=1.00-1.06 (m, 2H), 1.09-1.16 (m, 2H), 1.21 (t, J=7.1 Hz, 3H), 1.68-1.80 (m, 2H), 1.96 (br d, J=11 Hz, 2H), 2.59 (m, 1H), 3.22 (br. t, J=12 Hz, 2H), 3.48 (br. d, J=12.5 Hz, 2H), 3.75 (s, 3H), 4.10 (q, J=7.1 Hz, 2H), 4.16 (m, 1H), 7.74 (d, J=12.0 Hz, 1H), 8.69 (s, 1H), 14.95 (s, 1H).

By the same method as for Example 59A, from the same starting material and the correspondingly substituted piperidines, the following Examples 60A to 62A are prepared. If no example number is specified for the piperidine moiety, the substituted piperidine employed is commercially available.

Example 63A

6-Fluoro-7-(4-hydroxypiperidin-1-yl)-8-methoxy-4-oxo-1-(2,2,2-trifluoroethyl)-1,4-dihydroquinoline-3-carboxylic acid

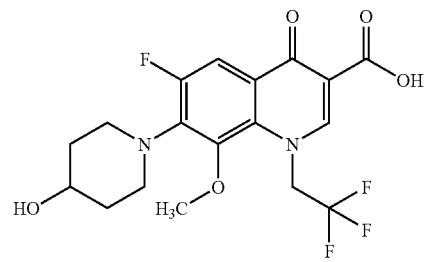

500 mg (1.30 mmol) of the compound of Example 38A and 394 mg (3.90 mmol) of 4-hydroxypiperidine are stirred in 5

| Example No. | Structure | Piperidine | Analytical data LC-MS (method)/measurement values |
|---|---|---|---|
| 60A | 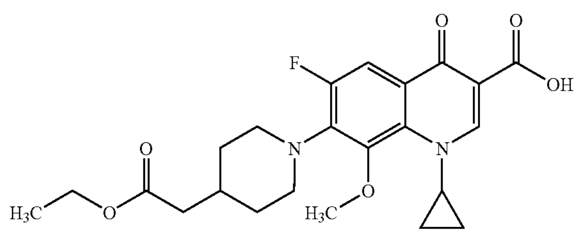 | | LC-MS (method 1): $R_t$ = 2.67 min MS (ES+): m/z = 447 (M + H)$^+$ |
| 61A | 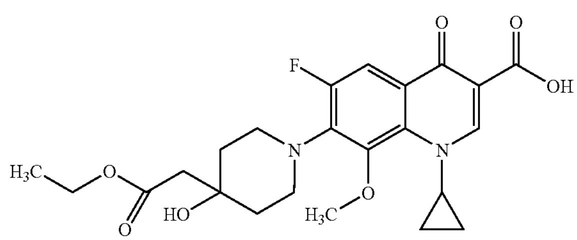 | 12A | LC-MS (method 3): $R_t$ = 2.29 min MS (ES+): m/z = 463 (M + H)$^+$ |
| 62A | | | LC-MS (method 2): $R_t$ = 2.06 min MS (ES+): m/z = 472 (M + H)$^+$ | ml of acetonitrile overnight at 50° C. The solvent is removed on a rotary evaporator and the residue is heated at reflux in 5 ml of ethanol for 2 h. The suspension is cooled to 0° C. and filtered. The solid is washed with ethanol/water 10:1 and dried under high vacuum. 253 mg (47% of theory) of the title compound are obtained.

LC-MS (method 3): $R_t$=2.21 min, MS (ES+)=419 (M+H)$^+$.

$^1$H NMR (400 MHz, DMSO-d$_6$): δ=1.50-1.61 (m, 2H), 1.86-1.93 (m, 2H), 3.16 (br t, J=11.5 Hz, 2H), 3.44 (br d, J=12 Hz, 2H), 3.70 (m, 1H), 3.80 (s, 3H), 4.79 (d, J=4.1 Hz, H), 5.78 (q, J=8.6 Hz, 2H), 7.80 (d, J=12.2 Hz, 1H), 9.01 (s, 1H), 14.66 (s, 1H).

By the same method as for Example 63A, with the correspondingly substituted piperidine, the following Example 64A is prepared.

Example 66A

6-Fluoro-7-[(all-cis)-4-hydroxy-3,5-dimethylpiperidin-1-yl]-8-methoxy-4-oxo-1-(2,2,2-trifluoroethyl)-1,4-dihydroquinoline-3-carboxylic acid

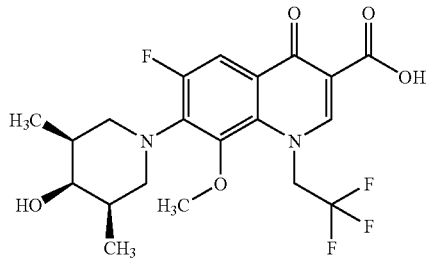

| Example No. | Structure | Starting Material | Analytical data LC-MS (method)/measurement values |
|---|---|---|---|
| 64A (1S,2R)-enantiomer | 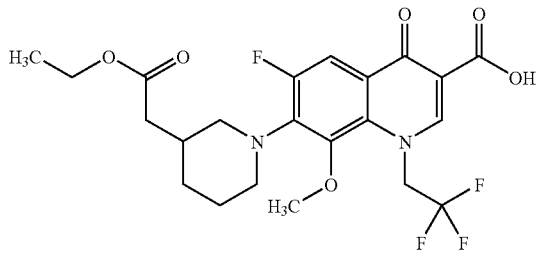 | 43A | LC-MS (method 2): $R_t$ = 2.32 min MS (ES+): m/z = 451 (M + H)$^+$ |

Example 65A

7-[3-(2-Ethoxy-2-oxoethyl)-piperidin-1-yl]-6-fluoro-8-methoxy-4-oxo-1-(2,2,2-trifluoroethyl)-1,4-dihydroquinoline-3-carboxylic acid (racemic)

100 mg (0.26 mmol) of the compound of Example 38A and 80 mg (0.47 mmol) of ethyl piperidin-3-ylacetate are stirred in 1.5 ml of acetonitrile at 50° C. overnight. The solvent is removed on a rotary evaporator and the residue is heated at reflux in 3 ml of ethanol for 1 h. Ethanol is removed on a rotary evaporator. The residue is stirred with ethanol several times and the solvent is removed on a rotary evaporator. The solid is then dissolved with 4 ml of ethanol/water 8:2, and the major part of the ethanol is removed by distillation, whereby the product precipitates. The mixture is cooled at 0° C. for 20 min and the product is collected by filtration. The solid is dried under high vacuum. 85 mg (67% of theory) of the title compound are obtained.

LC-MS (method 2): $R_t$=2.62 min
MS (ES+): m/z=489 (M+H)$^+$ $^1$H NMR (400 MHz, DMSO-d$_6$): δ=1.18 (t, 3H), 1.22 (m, 1H), 1.59-1.80 (m, 2H), 1.84 (br d, 1H), 2.09 (m, 1H), 2.30 (d, 2H), 3.11 (t, 1H), 3.39 (m, 2H), 3.79 (s, 3H), 4.05 (q, 2H), 5.78 (q, 2H), 7.80 (d, 1H), 9.01 (s, 1H), 14.6 (br s, 1H).

201 mg (0.52 mmol) of the compound of Example 38A and 95 mg (0.57 mmol) of (all-cis)-3,5-dimethyl-4-hydroxypiperidine hydrochloride (Example 11A) are stirred with 109 μl (0.63 mmol) of N,N-diisopropylethylamine in 1.5 ml of acetonitrile at 50° C. overnight. The solvent is removed on a rotary evaporator and the residue is taken up in 2 ml of triethylamine and 4 ml of ethanol and heated at reflux for 1 h. After cooling, the solution is freed from the solvents on a rotary evaporator and the product is purified by RP-HPLC (method 5). 36 mg (15% of theory) of the title compound are obtained.

LC-MS (method 2): $R_t$=2.28 min, MS (ES+)=447 (M+H)$^+$.

$^1$H NMR (400 MHz, CDCl$_3$): δ=1.01 (d, J=6.9 Hz, 6H), 1.43 (br.s, 1H), 2.02 (m, 2H), 3.09 (dd, J=4.2, 12.4 Hz, 2H), 3.22 (br t, J=11.5 Hz, 2H), 3.76 (br s, 1H), 3.78 (s, 3H), 5.31 (q, J=7.9 Hz, 2H), 7.91 (d, J=12.1 Hz, 1H), 8.52 (s, 1H), 14.50 (s, 1H).

Example 67A

6-Fluoro-8-methoxy-4-oxo-7-{3-oxo-1-oxa-3,8-diazaspiro[4,5]dec-8-yl}-1-(2,2,2-trifluoroethyl)-1,4-dihydroquinoline-3-carboxylic acid

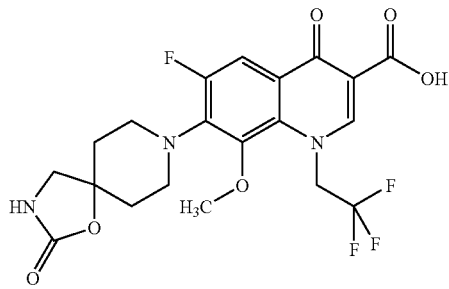

From 760 mg (4.87 mmol) of 1-oxa-3,8-diazaspiro[4,5]decan-2-one (for preparation see Journal of Medicinal Chemistry (1981), 24, 1320-28) and 937 mg (2.43 mmol) of Example 38A, in analogy to the preparation of Example 66A, 160 mg (6% of theory) of the title compound are isolated.

LC-MS (method 3): Rt=2.30 min, MS (ES+)=474 (M+H)+.

Example 68A

1-Cyclopropyl-6-fluoro-8-methoxy-4-oxo-7-{3-oxo-2,8-diazaspiro[4,5]decan-8-yl}-1,4-dihydroquinoline-3-carboxylic acid

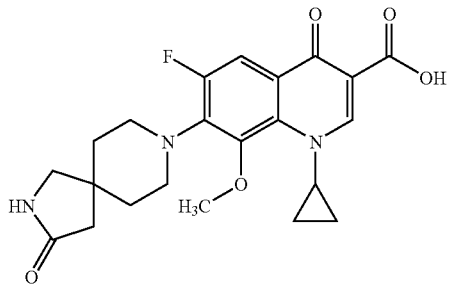

From 99 mg (0.52 mmol) of 3-oxo-2,8-diazaspiro[4,5]decane hydrochloride (Example 13A) the free base is liberated by stirring with 1 g of tris(aminoethyl)polystyrene in dichloromethane/methanol 10:1 for 20 minutes and subsequent filtration and removal of the solvents on a rotary evaporator. The residue is taken up in 3 ml of acetonitrile and stirred with 89 mg (0.26 mmol) of (T-4)-(1-cyclopropyl-6,7-difluoro-1,4-dihydro-8-methoxy-4-oxo-3-quinolincarboxylato-O3,O4)boron difluoride (for preparation see: Journal of Medicinal Chemistry (1995), 38(22), 4478-4487) at 50° C. overnight. The solvent is removed on a rotary evaporator and the residue is taken up in 3 ml of triethylamine and 30 ml of ethanol and heated at reflux for 1.5 h. After cooling, the solvents are removed on a rotary evaporator and the residue is taken up in a little DMSO and purified by RP-HPLC (method 5). 56 mg (50% of theory) of the title compound are obtained.

LC-MS (method 3): R$_t$=1.92 min, MS (ES+)=430 (M+H)+.

$^1$H NMR (400 MHz, CDCl$_3$): δ=0.97-1.03 (m, 2H), 1.18-1.27 (m, 2H), 1.86 (t, J=5.3 Hz, 4H), 2.35 (s, 2H), 3.32 (s, 2H), 3.33-3.43 (m, 4H), 3.79 (s, 3H), 4.03 (m, 1H), 5.50 (s, 1H), 7.89 (d, J=12.2 Hz, 1H), 8.82 (s, 1H), 14.73 (s, 1H)

Example 69A

6-Fluoro-8-methoxy-4-oxo-7-(3-oxo-2,8-diazaspiro[4.5]dec-8-yl)-1-(2,2,2-trifluoroethyl)-1,4-dihydroquinoline-3-carboxylic acid

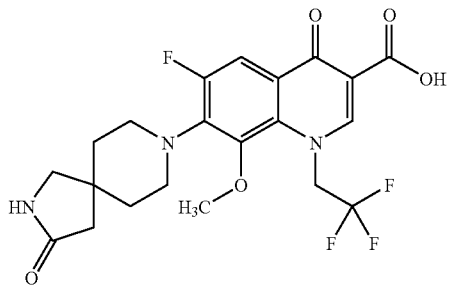

In analogy to the preparation of Example 68A, from 146 mg of Example 38A (0.38 mmol) and 145 mg (0.76 mmol) of 3-oxo-2,8-diazaspiro[4,5]decane hydrochloride (Example 13A), 73 mg (21% of theory) of the title compound are obtained.

LC-MS (method 3): R$_f$=2.13 min, MS (ES+)=472 (M+H)+.

Example 70A

8-Chloro-1-cyclopropyl-N-(2,4-dichlorobenzyl)-6,7-difluoro-4-oxo-1,4-dihydroquinoline-3-carboxamide

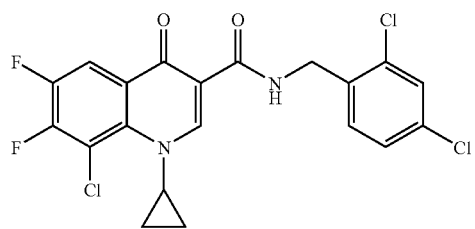

15.0 g of 8-chloro-1-cyclopropyl-6,7-difluoro-4-oxo-1,4-dihydroquinoline-3-carboxylic acid (for preparation see DE 3420743 or Y. Kimura et al. J. Med. Chem. 1994, 37 (20), 3344) are dissolved in 500 ml of DMF, and 31.3 g of PyBOP and 10.6 g of 2,4-dichlorobenzylamine are added. After one day the solvent is removed on a rotary evaporator and the residue is purified by flash chromatography on silica gel (toluene/ethyl acetate 95:5). 21.2 g (93% of theory) of the title compound are obtained.

LC-MS (method 1): R$_f$=3.10 min, MS (ES+)=457 (M+H)+.

$^1$H NMR (300 MHz, DMSO-d$_6$): δ=1.05-1.16 (m, 2H), 1.18-1.29 (m, 2H), 4.32 (m, 1H), 4.99 (d, J=6.0 Hz, 1H), 7.35-7.45 (m, 2H), 7.64 (d, J=2.0 Hz, 1H), 8.22 (dd, J=8.9, 10.0 Hz, 1H), 8.79 (s, 1H), 10.01 (t, J=6.0 Hz, 1H).

Exemplary Embodiments

Example 1

Ethyl 1-[3-{[(2,4-dichlorobenzyl)amino]carbonyl}-6-fluoro-8-methoxy-4-oxo-1-(2,2,2-trifluoroethyl)-1,4-dihydroquinolin-7-yl]piperidine-4-carboxylate

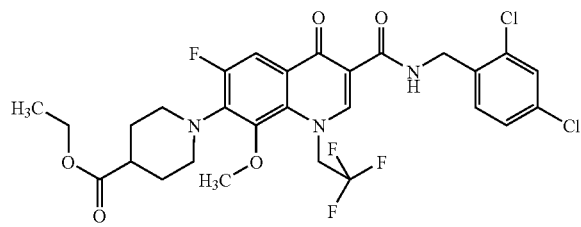

200.0 mg (0.42 mmol) of the compound of Example 47A and 111.3 mg (0.63 mmol) of 2,4-dichlorobenzylamine are provided in 2.6 ml of N,N-dimethylformamide, and 257 μl (1.48 mmol) of N,N-diisopropylethylamine and finally 438.8 mg (0.84 mmol) of PyBOP are added. The reaction is stirred at room temperature for 3 h. For the work up, the mixture is diluted with ethyl acetate and washed twice with water, the combined aqueous phases are extracted once with ethyl acetate and the combined organic phases are dried over sodium sulfate and freed completely from the solvent on a rotary evaporator. Fine purification of the residue by preparative RP-HPLC (method 5) gives the title compound with 250.0 mg (94% of theory).

$^1$H NMR (400 MHz, CDCl$_3$): δ=1.29 (t, J=7 Hz, 3H), 1.83-1.96 (m, 2H), 2.03 (dd, J=3, 13 Hz, 2H), 2.52 (tt, J=3.8, 11.1 Hz, 1H), 3.21 (br t, J=12 Hz, 2H), 3.49 (br d, J=12 Hz, 2H), 3.84 (s, 3H), 4.19 (q, J=7.1 Hz, 2H), 4.70 (d, J=6.2 Hz, 2H), 5.24 (q, J=8.1 Hz, 2H), 7.21 (dd, J=2.0, 8.3 Hz, 1H), 7.390 (d, J=8.1 Hz, 1H), 7.392 (d, J=2 Hz, 1H), 7.91 (d, J=12.5 Hz, 1H), 8.54 (s, 1H), 10.22 (t, J=5.9 Hz, 1H).

HPLC (method 7): $R_t$=5.65 min.

MS (ES+): m/z=632 (M+H)$^+$

Example 2

Ethyl 1-[6-fluoro-8-methoxy-3-({[2-methyl-4-(trifluoromethoxy)benzyl]amino}carbonyl)-4-oxo-1-(2,2,2-trifluoroethyl)-1,4-dihydroquinolin-7-yl]piperidine-4-carboxylate

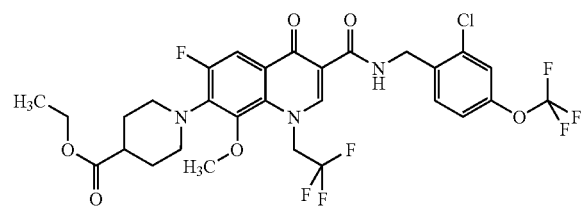

100.0 mg (0.21 mmol) of the compound of Example 47A and 157.2 mg (0.42 mmol) of 2-methyl-4-(trifluoromethoxy) benzylamine (Example 5A) are provided in 3 ml of N,N-dimethylformamide, and 202 µl (1.16 mmol) of N,N-diisopropylethylamine and finally 274.2 mg (0.84 mmol) of PyBOP are added. After 3 h at RT the entire reaction mixture is separated by preparative HPLC (method 5). 96.0 mg (69% of theory) of the title compound are obtained.

$^1$H NMR (400 MHz, CDCl$_3$): δ=1.29 (t, J=7.1 Hz, 3H), 1.83-1.96 (m, 2H), 2.03 (br dd, J=3, 13 Hz, 2H), 2.40 (s, 3H), 2.51 (m, 1H), 3.21 (br. t, J=12 Hz, 2H), 3.49 (br. d, J=12 Hz, 2H), 3.84 (s, 3H), 4.19 (q, J=7.1 Hz, 2H), 4.62 (d, J=5.6 Hz, 2H), 5.24 (q, J=8.0 Hz, 2H), 6.98-7.03 (m, 2H), 7.36 (d, J=8.1 Hz, 1H), 7.88 (d, J=12.5 Hz, 1H), 8.56 (s, 1H), 10.07 (t, J=5.6 Hz, 1H).

HPLC (method 8): $R_t$=5.43 min.

MS (ES+): m/z=662 (M+H)$^+$

Example 3

Ethyl 1-[3-({[2-chloro-4-(trifluoromethoxy)benzyl]amino}carbonyl)-6-fluoro-8-methoxy-4-oxo-1-(2,2,2-trifluoroethyl)-1,4-dihydroquinolin-7-yl]piperidine-4-carboxylate

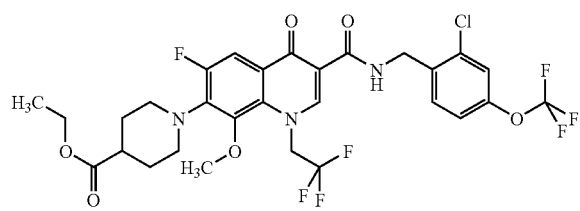

50.0 mg (0.105 mmol) of the compound of Example 47A and 55.2 mg (0.21 mmol) of 2-chloro-4-(trifluoromethoxy) benzylamine (Example 7A) are provided in 1.5 ml of N,N-dimethylformamide, and 101 µl (0.58 mmol) of N,N-diisopropylethylamine and finally 137 mg (0.26 mmol) of PyBOP are added. After 30 min the entire reaction mixture is separated by preparative HPLC (method 5). 63 mg (87% of theory) of the title compound are obtained.

LC-MS (method 3): $R_t$=3.43 min.

MS (ESI pos): m/z=682 (M+H)$^+$ $^1$H NMR (400 MHz, CDCl$_3$): δ=1.29 (t, J=7.1 Hz, 3H), 1.83-1.96 (m, 2H), 1.99-2.03 (m, 2H), 2.52 (m, 1H), 3.21 (br. t, J=12 Hz, 2H), 3.49 (br. d, J=12 Hz, 2H), 3.84 (s, 3H), 4.19 (q, J=7.1 Hz, 2H), 4.72 (d, J=6.0 Hz, 2H), 5.24 (q, J=8.0 Hz, 2H), 7.10 (d, J=8.7 Hz, 2H), 7.27 (under CHCl$_3$ signal, 1H), 7.49 (d, J=8.7 Hz, 1H), 7.86 (d, J=12.6 Hz, 1H), 8.55 (s, 1H), 10.77 (t, J=6.0 Hz, 1H).

Example 4

Ethyl 1-[6-fluoro-1-(2-fluoroethyl)-8-methoxy-3-({[2-methyl-4-(trifluoromethoxy)benzyl]amino}carbonyl)-4-oxo-1,4-dihydroquinolin-7-yl]piperidine-4-carboxylate

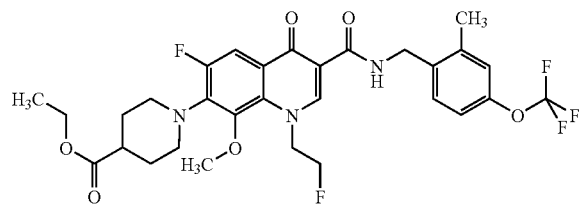

72.0 mg (0.164 mmol) of the compound of Example 46A and 47.6 mg (0.197 mmol) of 2-methyl-4-(trifluoromethoxy) benzylamine hydrochloride (Example 5A) are provided in 2.15 ml of N,N-dimethylformamide, and 157 µl (0.90 mmol) of N,N-diisopropylethylamine and finally 170.9 mg (0.33 mmol) of PyBOP are added. After overnight stirring at RT the entire reaction mixture is separated by preparative HPLC (method 5). 85 mg (83% of theory) of the title compound are obtained.

LC-MS (method 3): $R_t$=3.22 min.

MS (ESI pos): m/z=626 (M+H)$^+$ $^1$H NMR (400 MHz, CDCl$_3$): δ=1.29 (t, J=7.1 Hz, 3H), 1.83-1.96 (m, 2H), 2.03 (m, 2H), 2.41 (s, 3H), 2.51 (m, 1H), 3.21 (br. t, J=12 Hz, 2H), 3.47 (br. d, J=13 Hz, 2H), 3.82 (s, 3H), 4.18 (q, J=7.1 Hz, 2H), 4.62 (d, J=5.7 Hz, 2H), 4.69 (dt, J=46, 4 Hz, 2H), 4.78 (dt, J=31, 4 Hz, 2H), 7.01 (d, J=8.0 Hz, 1H), 7.02 (s, 1H), 7.36 (d, J=8.0 Hz, 1H), 7.93 (d, J=12.6 Hz, 1H), 8.64 (s, 1H), 10.19 (t, J=5.7 Hz, 1H).

Example 5

Ethyl [6-fluoro-8-methoxy-3-({[2-methyl-4-(trifluoromethoxy)benzyl]amino}carbonyl)-4-oxo-1-(2,2,2-trifluoroethyl)-1,4-dihydroquinolin-7-yl]piperidin-4-ylacetate

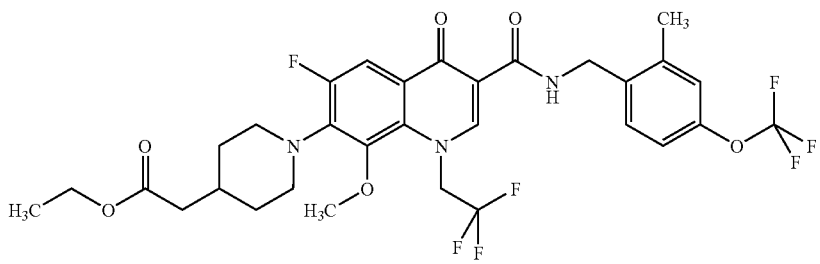

100.0 mg (0.18 mmol) of the compound of Example 57A and 46.7 mg (0.19 mmol) of 2-methyl-4-(trifluoromethoxy)benzylamine hydrochloride (Example 5A) are provided in 1 ml of N,N-dimethylformamide, and 177 μl (1.01 mmol) of N,N-diisopropylethylamine and finally 234.7 mg (0.46 mmol) of PyBOP are added. After 1.5 h at RT the entire reaction mixture is separated by preparative HPLC (method 5). 82.0 mg (66% of theory) of the title compound are obtained.

LC-MS (method 2): $R_f$=3.22 min.
MS (ESI pos): m/z=676 (M+H)$^+$
$^1$H NMR (400 MHz, CDCl$_3$): δ=1.28 (t, J=7.1 Hz, 3H), 1.46 (m, 2H), 1.82 (br. d, J=11 Hz, 2H), 2.20 (m, 1H), 2.32 (d, J=7.1 Hz, 2H), 2.41 (s, 3H), 3.20 (br. t, J=12 Hz, 2H), 3.45 (br. d, J=12 Hz, 2H), 3.81 (s, 3H), 4.16 (q, J=7.1 Hz, 2H), 4.62 (d, J=5.6 Hz, 2H), 5.25 (q, J=8.0 Hz, 2H), 7.00-7.04 (m, 2H), 7.36 (d, J=8.1 Hz, 1H), 7.87 (d, J=12.5 Hz, 1H), 8.56 (s, 1H), 10.08 (t, J=5.6 Hz, 1H).

Example 6

Ethyl [3-{[(2,4-dichlorobenzyl)amino]carbonyl}-6-fluoro-8-methoxy-4-oxo-1-(2,2,2-trifluoroethyl)-1,4-dihydroquinolin-7-yl]piperidin-3-ylacetate

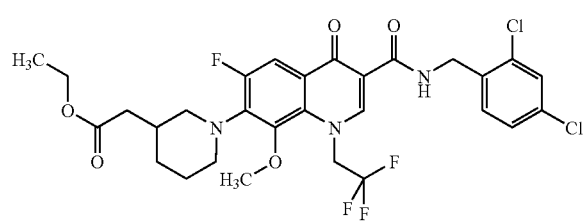

78 mg (0.16 mmol) of the compound of Example 65A, 116.3 mg (0.22 mmol) of PyBOP and 9.7 mg of DMAP (0.08 mmol) are provided in 2 ml of N,N-dimethylformamide and 56.2 mg (0.32 mmol) of 2,4-dichlorobenzylamine are added. The mixture is stirred at RT overnight and then separated by preparative HPLC (method 5). 49.0 mg (47% of theory) of the title compound are obtained.

LC-MS (method 2): $R_f$=3.21 min.

MS (ESI pos): m/z=646 (M+H)$^+$ $^1$H NMR (400 MHz, DMSO-d$_6$): δ=1.16 (t, J=7.1 Hz, 3H), 1.18-1.28 (m, 1H), 1.60-1.78 (m, 2H), 1.84 (m, 1H), 2.09 (m, 1H), 2.27-2.31 (m, 2H), 2.87 (br. t, J=10.5 Hz, 1H), 3.08 (br. t, J=11.5 Hz, 1H), 3.36 (m, partly under water signal, 1H ?), 3.78 (s, 3H), 4.04 (q, J=7.1 Hz, 2H), 4.60 (d, J=6.0 Hz, 2H), 5.69 (q, J=8.7 Hz, 2H), 7.38-7.45 (m, 2H), 7.64 (d, J=1.7 Hz, 1H), 7.77 (d, J=12.1 Hz, 1H), 8.83 (s, 1H), 10.14 (t, J=6.0 Hz, 1H).

In analogy to Example 1 the following Examples 7 to 19 are prepared. If no example number is given for the starting amine it is commercially available.

| Example No. | Structure | Starting Materials Example No. | Analytical data LC-MS (method)/ measurement values HPLC (method)/ measurement values MS (method)/measurement values |
|---|---|---|---|
| 7 | 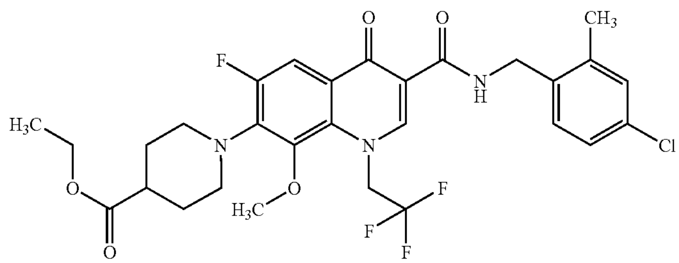 | 47A | HPLC (method 7):<br>R$_t$ = 5.55 min<br>MS (ES+): m/z = 612 (M + H)$^+$ |
| 8 | 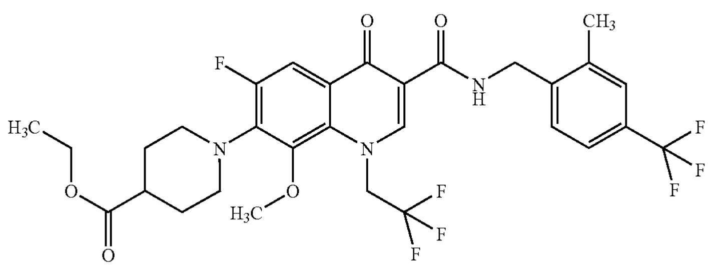 | 47A + 9A | LC-MS (method 3):<br>R$_t$ = 3.36 min<br>MS (ES+): m/z = 646 (M + H)$^+$ |
| 9 | 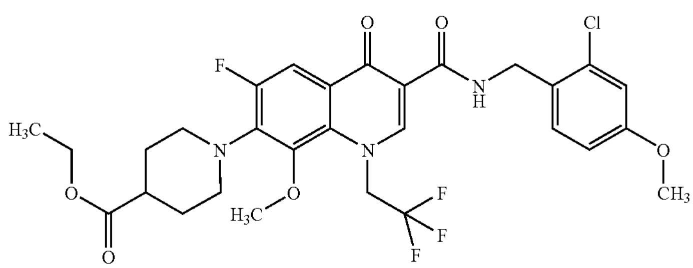 | 47A | LC-MS (method 3):<br>R$_t$ = 3.28 min<br>MS (ES+): m/z = 628 (M + H)$^+$ |
| 10 | 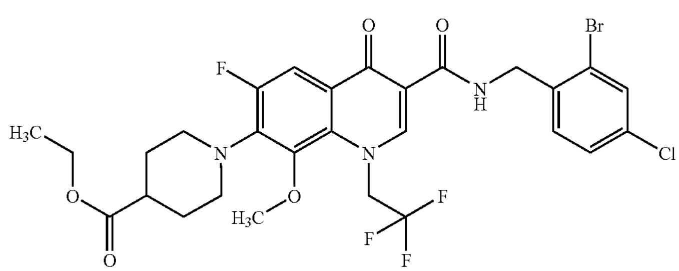 | 47A + 6A | LC-MS (method 3):<br>R$_t$ = 3.44 min<br>MS (ES+):<br>m/z = 676/678 (M + H)$^+$ |
| 11 | 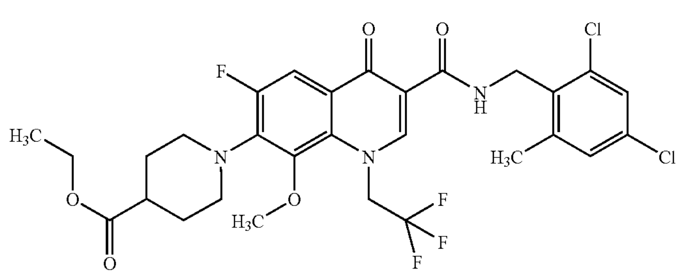 | 47A + 8A | LC-MS (method 1):<br>R$_t$ = 3.40 min<br>MS (ES+): m/z = 646 (M + H)$^+$ |

-continued

| Example No. | Structure | Starting Materials Example No. | Analytical data LC-MS (method)/ measurement values HPLC (method)/ measurement values MS (method)/measurement values |
|---|---|---|---|
| 12 | 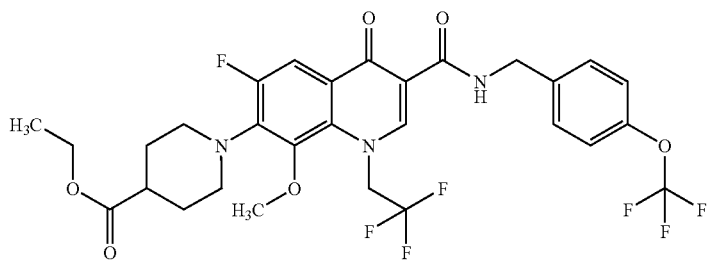 | 47A | LC-MS (method 3):<br>$R_t$ = 3.31 min<br>MS (ES+): m/z = 648 (M + H)$^+$ |
| 13 | 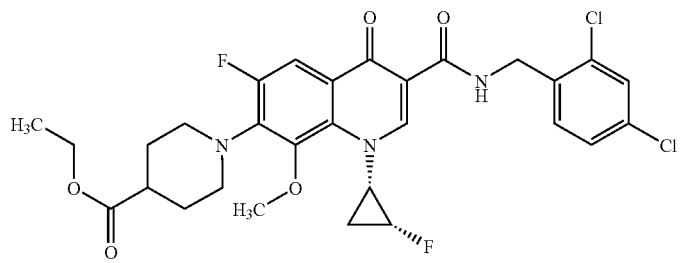 | 64A | LC-MS (method 2):<br>$R_t$ = 3.04 min<br>MS (ES+): m/z = 608 (M + H)$^+$ |
| 14 | 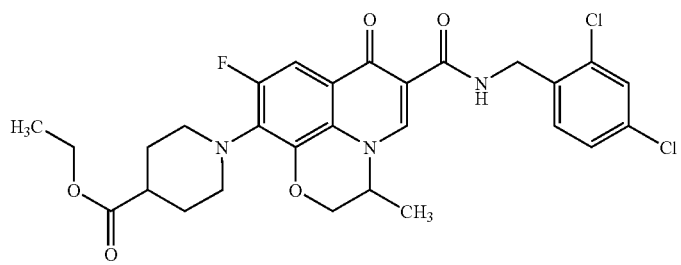 | 53A | LC-MS (method 1):<br>$R_t$ = 3.14 min<br>MS (ES+): m/z = 576 (M + H)$^+$ |
| 15 | 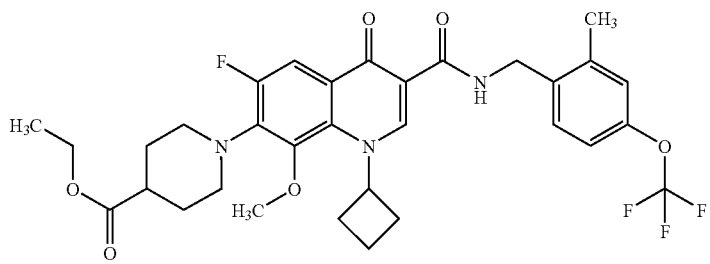 | 50A + 5A | LC-MS (method 2):<br>$R_t$ = 3.21 min<br>MS (ES+): m/z = 634 (M + H)$^+$ |
| 16 | 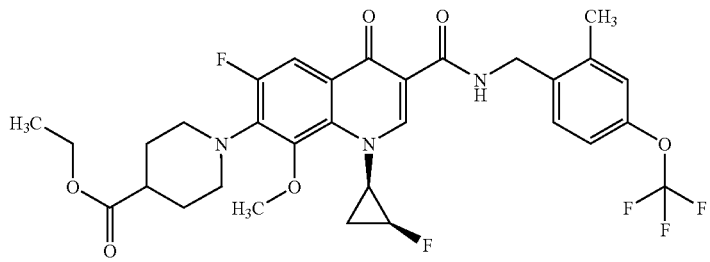 | 52A + 5A | LC-MS (method 1):<br>$R_t$ = 3.21 min<br>MS (ES+): m/z = 638 (M + H)$^+$ |

| Example No. | Structure | Starting Materials Example No. | Analytical data LC-MS (method)/measurement values HPLC (method)/measurement values MS (method)/measurement values |
|---|---|---|---|
| 17 | 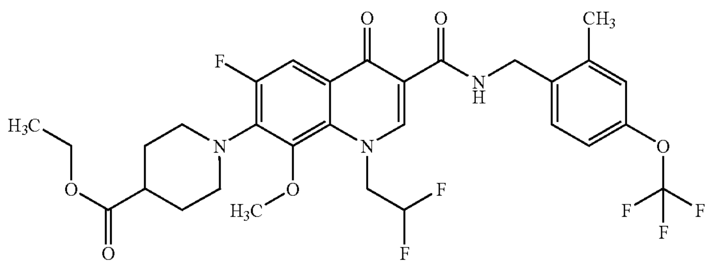 | 51A + 5A | LC-MS (method 2): $R_t$ = 3.07 min MS (ES+): m/z = 644 (M + H)$^+$ |
| 18 | 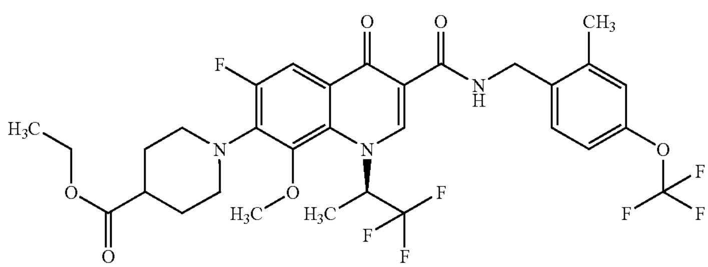 | 48A + 5A | LC-MS (method 2): $R_t$ = 3.22 min MS (ES+): m/z = 676 (M + H)$^+$ |
| 19 | 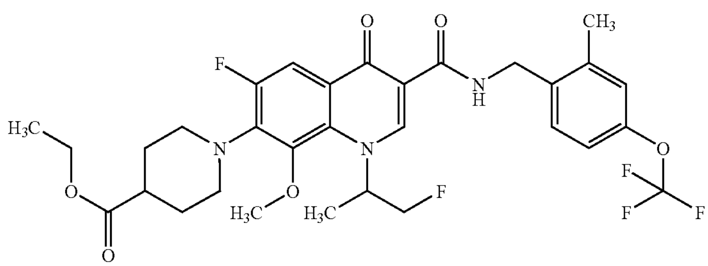 | 49A + 5A | LC-MS (method 2): $R_t$ = 3.10 min MS (ES+): m/z = 640 (M + H)$^+$ |

Example 20

7-[(3S)-3-(2-Ethoxy-2-oxoethyl)piperidin-1-yl]-6-fluoro-8-methoxy-N-[2-methyl-4-(trifluoromethoxy)benzyl]-4-oxo-1-(2,2,2-trifluoroethyl)-1,4-dihydro-quinoline-3-carboxamide

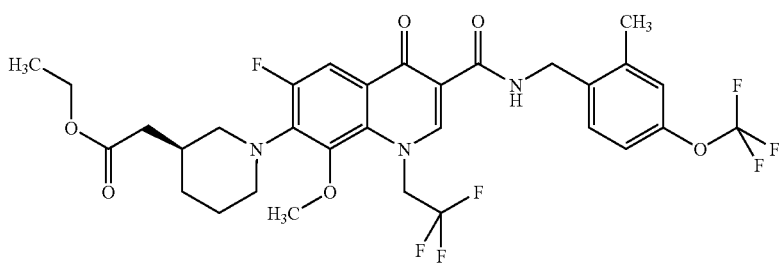

100.0 mg (0.21 mmol) of the compound of Example 55A and 59.4 mg (0.25 mmol) of 2-methyl-4-(trifluoromethoxy)benzylamine hydrochloride (Example 5A) are provided in 2.7 ml of N,N-dimethylformamide and 196 µl (1.13 mmol) of N,N-diisopropylethylamine and finally 213.1 mg (0.41 mmol) of PyBOP are added. The reaction mixture is left stirring overnight at RT and then separated as a whole by preparative HPLC (method 5). 100.0 mg (72% of theory) of the title compound are obtained.

LC-MS (method 2): $R_t$=3.24 min
MS (ES+): m/z=676 (M+H)$^+$
$^1$H NMR (400 MHz, CDCl$_3$): δ=10.08 (t, J=5.7 Hz, 1H), 8.55 (s, 1H), 7.87 (d, J=12.4 Hz, 1H), 7.36 (d, J=8.3 Hz, 1H), 6.98-7.03 (m, 2H), 5.25 (q, J=7.9 Hz, 2H), 4.62 (d, J=5.6 Hz, 2H), 4.14 (q, J=7.1 Hz, 2H), 3.83 (s, 3H), 3.45 (br. d, J=11 Hz, 1H), 3.38 (br. d, J=12 Hz, 1H), 3.12 (br.t, J~11 Hz, 1H), 2.88 (br.t, J~11 Hz, 1H), 2.41 (s, 3H), 2.30-2.20 (m, 3H), 1.95 (br. d, J~11 Hz, 1H), 1.85-1.70 (m, 2H), 1.25 (t, J=7.1 Hz, 3H), 1.24 (m, 1H).

Example 21

7-[(3R)-3-(2-Ethoxy-2-oxoethyl)piperidin-1-yl]-6-fluoro-8-methoxy-N-[2-methyl-4-(trifluoromethoxy)benzyl]-4-oxo-1-(2,2,2-trifluoroethyl)-1,4-dihydroquinoline-3-carboxamide

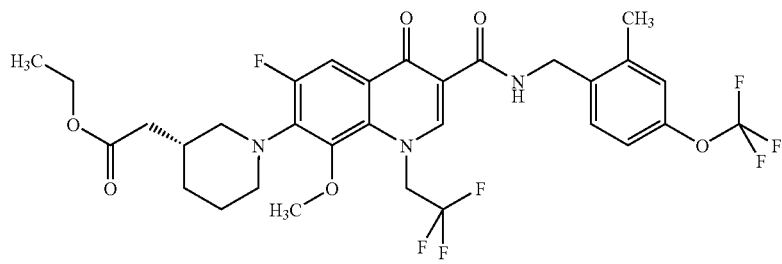

100.0 mg (0.21 mmol) of the compound of Example 56A and 59.4 mg (0.25 mmol) of 2-methyl-4-(trifluoromethoxy)benzylamine hydrochloride (Example 5A) are provided in 2.7 ml of N,N-dimethylformamide and 196 µl (1.13 mmol) of N,N-diisopropylethylamine and finally 213.1 mg (0.41 mmol) of PyBOP are added. The reaction mixture is left stirring overnight at RT and then separated as a whole by preparative HPLC (method 5). 108 mg (78% of theory) of the title compound are obtained.

LC-MS (method 2): $R_t$=3.23 min
MS (ES+): m/z=676 (M+H)$^+$ $^1$H NMR (400 MHz, CDCl$_3$): δ=10.08 (t, J=5.7 Hz, 1H), 8.55 (s, 1H), 7.87 (d, J=12.4 Hz, 1H), 7.36 (d, J=8.3 Hz, 1H), 6.98-7.03 (m, 2H), 5.25 (q, J=7.9 Hz, 2H), 4.62 (d, J=5.6 Hz, 2H), 4.14 (q, J=7.1 Hz, 2H), 3.83 (s, 3H), 3.45 (br. d, J~11 Hz, 1H), 3.38 (br. d, J~12 Hz, 1H), 3.12 (br. t, J~11 Hz, 1H), 2.88 (br. t, J~11 Hz, 1H), 2.41 (s, 3H), 2.30-2.20 (m, 3H), 1.95 (br. d, J~11 Hz, 1H), 1.85-1.70 (m, 2H), 1.25 (t, J=7.1 Hz, 3H), 1.24 (m, 1H).

In analogy to Example 1 the following Examples 22 to 30 are also prepared.

| Example No. | Structure | Starting Materials Example No. | Analytical data LC-MS (method)/ measurement values HPLC (method)/ measurement values MS (method)/measurement values |
|---|---|---|---|
| 22 | 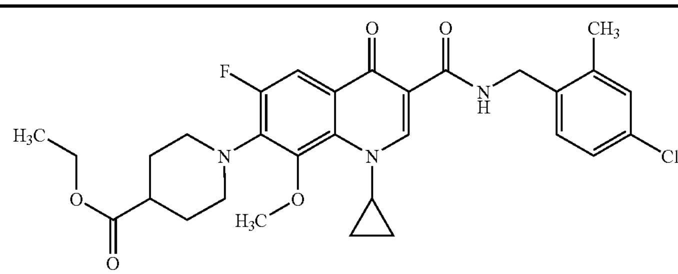 | 59A | LC-MS (method 2): $R_t$ = 3.05 min MS (ES+): m/z = 570 (M + H)$^+$ |
| 23 | 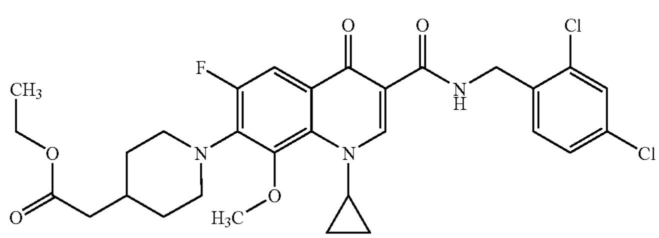 | 60A | LC-MS (method 1): $R_t$ = 3.17 min MS (ES+): m/z = 604 (M + H)$^+$ |
| 24 | 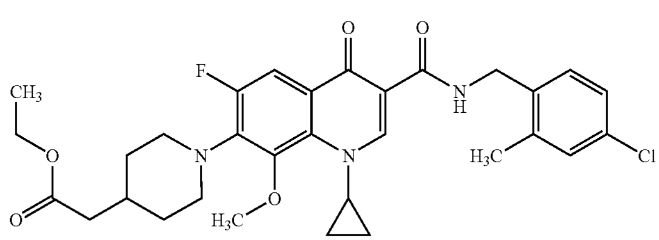 | 60A | LC-MS (method 2): $R_t$ = 3.12 min MS (ES+): m/z = 584 (M + H)$^+$ |

-continued

| Example No. | Structure | Starting Materials Example No. | Analytical data LC-MS (method)/ measurement values HPLC (method)/ measurement values MS (method)/measurement values |
|---|---|---|---|
| 25 | 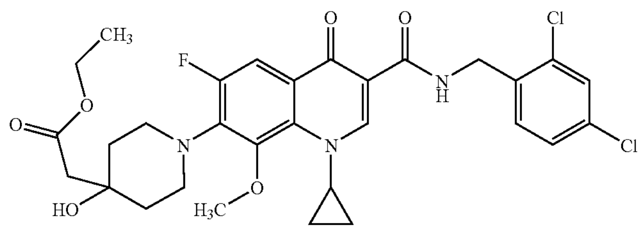 | 61A | LC-MS (method 3): $R_t$ = 3.17 min MS (ES+): m/z = 620 (M + H)$^+$ |
| 26 | 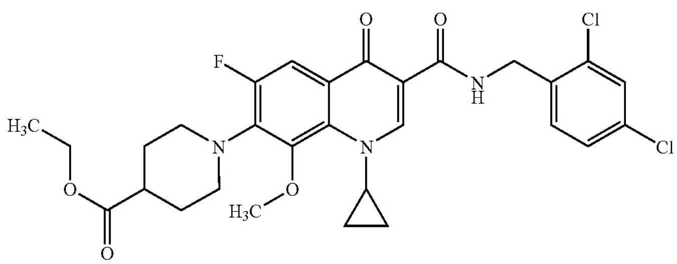 | 59A | LC-MS (method 2): $R_t$ = 3.12 min MS (ES+): m/z = 590 (M + H)$^+$ |
| 27 | 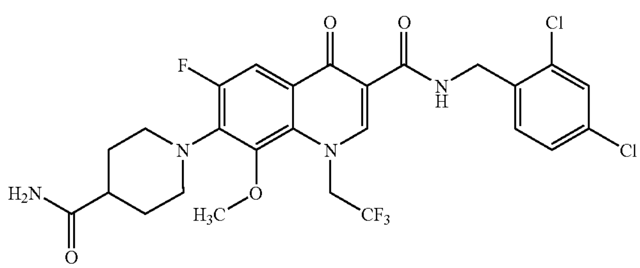 | 58A | HPLC (method 7): $R_t$ = 4.64 min MS (ES+): m/z = 603 (M + H)$^+$ |
| 28 | 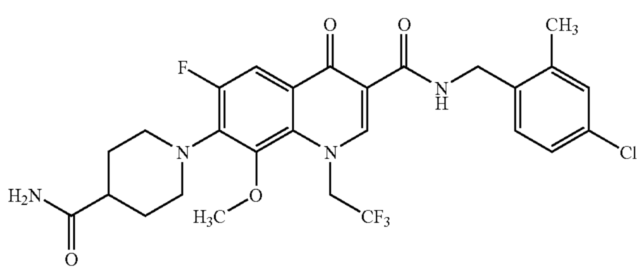 | 58A | HPLC (method 7): $R_t$ = 4.54 min MS (ES+): m/z = 583 (M + H)$^+$ |
| 29 | 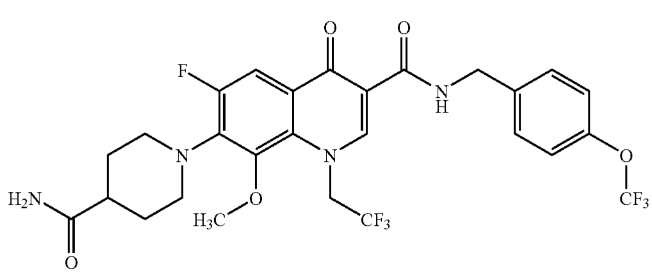 | 58A | MS (ES+): m/z = 619 (M + H)$^+$ |

| Example No. | Structure | Starting Materials Example No. | Analytical data LC-MS (method)/ measurement values HPLC (method)/ measurement values MS (method)/measurement values |
|---|---|---|---|
| 30 | 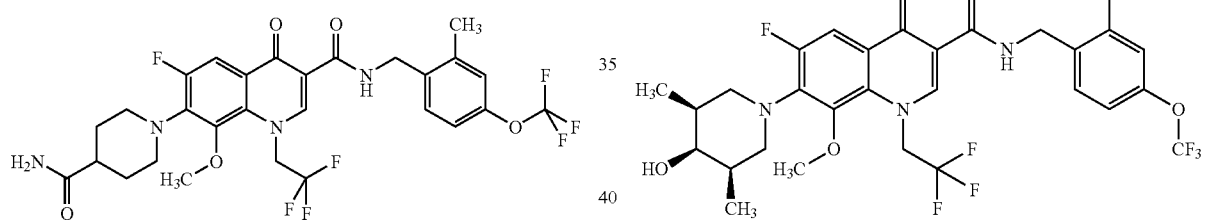 | 58A + 9A | LC-MS (method 1): $R_t$ = 2.59 min MS (ES+): m/z = 617 (M + H)⁺ |

Example 31

1-[6-Fluoro-8-methoxy-3-({[2-methyl-4-(trifluoromethoxy)benzyl]amino}carbonyl)-4-oxo-1-(2,2,2-trifluoroethyl)-1,4-dihydroquinolin-7-yl]piperidine-4-carboxamide 60.0 mg (0.14 mmol) of the compound of Example 58A and 46 mg (0.16 mmol) of 2-methyl-4-(trifluoromethoxy)benzylamine hydrochloride (Example 5A) are provided in 1.7 ml of N,N-dimethylformamide and 129 µl (0.74 mmol) of N,N-diisopropylethylamine and finally 140.2 mg (0.27 mmol) of PyBOP are added. The reaction mixture is left stirring overnight at RT and then separated as a whole by preparative HPLC (method 5). 57 mg (67% of theory) of the title compound are obtained.

LC-MS (method 1): $R_t$=2.63 min

MS (ES+): m/z=633 (M+H)⁺.

¹H NMR (400 MHz, CDCl₃): δ=1.88-2.03 (m, 4H), 2.40 (m, 1H), 2.41 (s, 3H), 3.23 (br. t, J=12 Hz, 2H), 3.53 (br. d, J=12 Hz, 2H), 3.87 (s, 3H), 4.62 (d, J=5.6 Hz, 2H), 5.26 (q, J=8.0 Hz, 2H), 5.34 (br.s, 1H), 5.49 (br s, 1H), 6.98-7.04 (m, 2H), 7.34 (d, J=8.1 Hz, 1H), 7.89 (d, J=12.5 Hz, 1H), 8.56 (s, 1H), 10.06 (t, J=5 Hz, 1H).

Example 32

6-Fluoro-7-[(all-cis)-4-hydroxy-3,5-dimethylpiperidin-1-yl]-8-methoxy-N-[2-methyl-4-(trifluoromethoxy)benzyl]-4-oxo-1-(2,2,2-trifluoroethyl)-1,4-dihydroquinoline-3-carboxamide 36 mg (0.081 mmol) of the compound of Example 66A and 21.4 mg (0.089 mmol) of 2-methyl-4-(trifluoromethoxy)benzylamine hydrochloride (Example 5A) are provided in 0.7 ml of N,N-dimethylformamide and 77 µl (0.44 mmol) of N,N-diisopropylethylamine and finally 105 mg (0.20 mmol) of PyBOP are added. The reaction mixture is left stirring at RT for 1.5 h, 1 ml of 1N hydrochloric acid is added, and then the mixture as a whole is separated by preparative HPLC (method 5). 36 mg (70% of theory) of the title compound are obtained.

LC-MS (method 3): $R_t$=3.24 min

MS (ES+): m/z=634 (M+H)⁺.

¹H NMR (400 MHz, CDCl₃): δ=1.01 (d, J=6.9 Hz, 6H), 2.02 (m, 2H), 2.41 (s, 3H), 3.05 (dd, J=4.1, 12.4 Hz, 2H), 3.20 (t, J=11.7 Hz, 2H), 3.74 (s, 1H), 3.77 (s, 3H), 4.62 (d, J=5.6 Hz, 2H), 5.26 (q, J=8.0 Hz, 2H), 6.99-7.04 (m, 2H), 7.36 (d, J=8.1 Hz, 1H), 7.87 (d, J=12.5 Hz, 1H), 8.55 (s, 1H), 10.10 (t, J=5.4 Hz, 1H).

Example 33

6-Fluoro-8-methoxy-N-[2-methyl-4-(trifluoromethoxy)benzyl]-4-oxo-7-(3-oxo-2,8-diazaspiro[4.5]dec-8-yl)-1-(2,2,2-trifluoroethyl)-1,4-dihydroquinoline-3-carboxamide

Example 34

1-Cyclopropyl-6-fluoro-8-methoxy-N-[2-methyl-4-(trifluoromethoxy)benzyl]-4-oxo-7-(3-oxo-2,8-diazaspiro[4.5]dec-8-yl)-1,4-dihydroquinoline-3-carboxamide

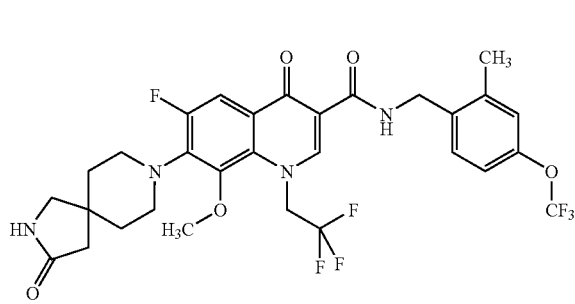

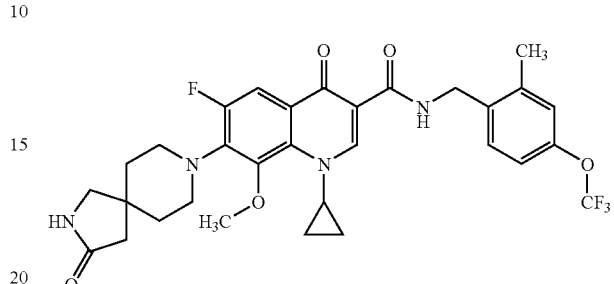

36 mg (0.076 mmol) of the compound of Example 69A and 22.1 mg (0.092 mmol) of 2-methyl-4-(trifluoromethoxy)benzylamine hydrochloride (Example 5A) are provided in 1.0 ml of N,N-dimethylformamide and 73 µl (0.42 mmol) of N,N-diisopropylethylamine and finally 79.4 mg (0.15 mmol) of PyBOP are added. The reaction mixture is left stirring overnight at RT and then separated as a whole by preparative HPLC (method 5). 27 mg (54% of theory) of the title compound are obtained.

LC-MS (method 1): $R_t$=2.73 min

MS (ES+): m/z=659 (M+H)$^+$.

$^1$H NMR (400 MHz, CDCl$_3$): δ=1.84-1.88 (m, 4H), 2.34 (s, 2H), 2.41 (s, 3H), 3.31 (s, 2H), 3.32 (br.s, 4H), 3.84 (s, 3H), 4.62 (d, J=5.6 Hz, 2H), 5.24 (q, J=8.0 Hz, 2H), 6.99-7.03 (m, 2H), 7.36 (d, J=7.7 Hz, 1H), 7.90 (d, J=12.5 Hz, 1H), 8.57 (s, 1H), 10.05 (t, J=5.5 Hz, 1H).

28 mg (0.065 mmol) of the compound of Example 68A and 18.9 mg (0.078 mmol) of 2-methyl-4-(trifluoromethoxy)benzylamine hydrochloride (Example 5A) are provided in 0.8 ml of N,N-dimethylformamide and 62 µl (0.36 mmol) of N,N-diisopropylethylamine and finally 67.9 mg (0.13 mmol) of PyBOP are added. The reaction mixture is left stirring for 30 minutes at RT and then separated as a whole by preparative HPLC (method 5). 27 mg (54% of theory) of the title compound are obtained.

LC-MS (method 2): $R_t$=2.45 min

MS (ES+): m/z=617 (M+H)$^+$.

1H NMR (400 MHz, CDCl$_3$): δ=0.97 (m, 2H), 1.17 (m, 2H), 1.85 (m, 4H), 2.34 (s, 2H), 2.41 (s, 3H), 3.31 (s, 2H), 3.30-3.38 (m, 4H), 3.78 (s, 3H), 3.97 (m, 1H), 4.61 (d, J=5.4 Hz, 2H), 5.58 (s, 1H), 7.005 (d, J=8 Hz, 1H), 7.01 (s, 1H), 7.36 (d, J=8.0 Hz, 1H), 7.85 (d, J=12.4 Hz, 1H), 8.86 (s, 1H), 10.21 (br. s, 1H).

In analogy to Example 1 the following Examples 35 to 42 are also prepared.

| Example No. | Structure | Starting Materials Example No. | Analytical data LC-MS (method)/measurement values HPLC (method)/measurement values MS (method)/measurement values |
|---|---|---|---|
| 35 | ![structure] | 68A | LC-MS (method 2): $R_t$ = 2.43 min MS (ES+): m/z = 587 (M + H)$^+$ |

-continued

| Example No. | Structure | Starting Materials Example No. | Analytical data LC-MS (method)/ measurement values HPLC (method)/ measurement values MS (method)/ measurement values |
|---|---|---|---|
| 36 | 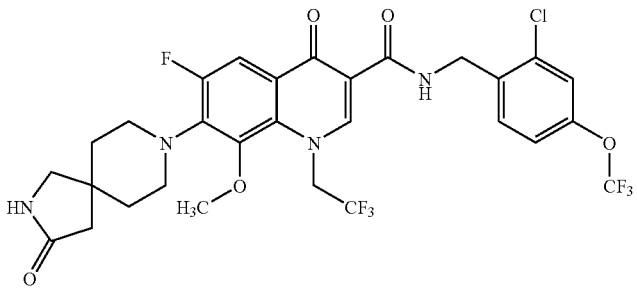 | 69A + 7A | LC-MS (method 3): $R_t$ = 2.86 min MS (ES+): m/z = 679 (M + H)$^+$ |
| 37 | 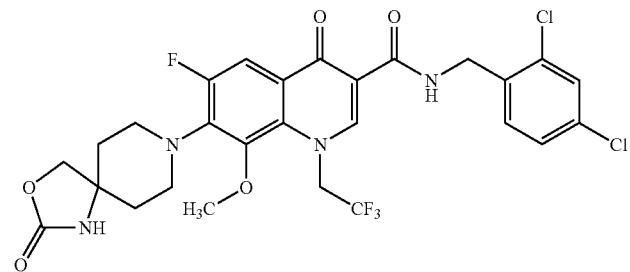 | 54A | LC-MS (method 3): $R_t$ = 2.90 min MS (ES+): m/z = 631 (M + H)$^+$ |
| 38 | 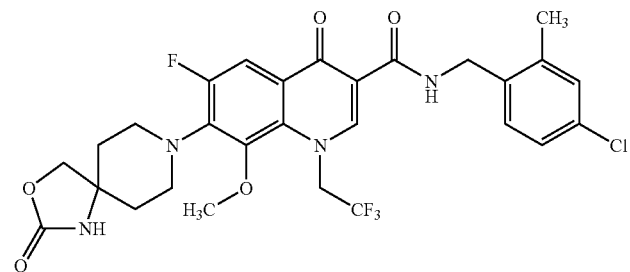 | 54A | LC-MS (method 1): $R_t$ = 2.67 min MS (ES+): m/z = 611 (M + H)$^+$ |
| 39 | 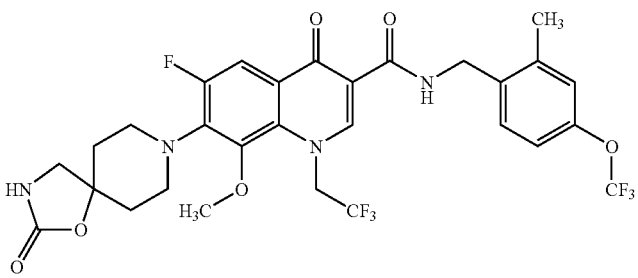 | 67A + 5A | LC-MS (method 2): $R_t$ = 2.57 min MS (ES+): m/z = 661 (M + H)$^+$ |
| 40 | 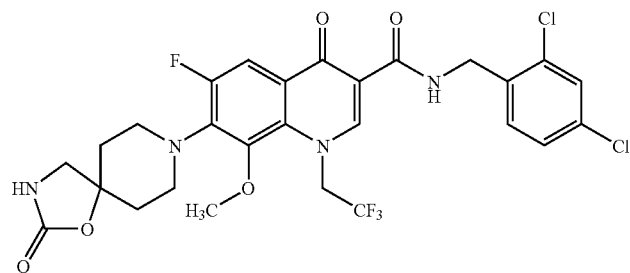 | 67A | LC-MS (method 1): $R_t$ = 2.72 min MS (ES+): m/z = 631 (M + H)$^+$ |

| Example No. | Structure | Starting Materials Example No. | Analytical data LC-MS (method)/ measurement values HPLC (method)/ measurement values MS (method)/ measurement values |
|---|---|---|---|
| 41 | 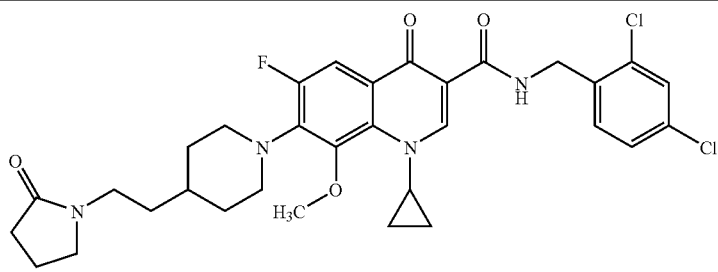 | 62A | LC-MS (method 3): $R_t$ = 3.29 min MS (ES+): m/z = 629 (M + H)$^+$ |
| 42 | 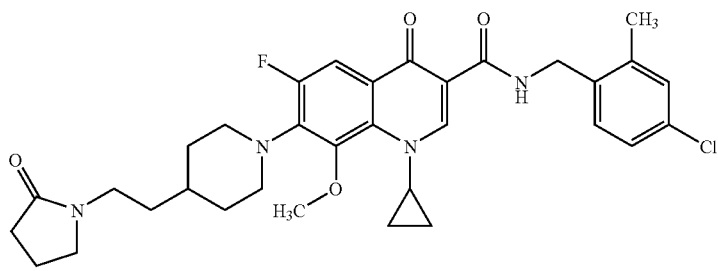 | 62A | LC-MS (method 3): $R_t$ = 3.24 min MS (ES+): m/z = 609 (M + H)$^+$ |

Example 43

8-Chloro-7-{4-[(cyclohexylamino)carbonyl]piperidin-1-yl}-1-cyclopropyl-N-(2,4-dichlorobenzyl)-6-fluoro-4-oxo-1,4-dihydroquinoline-3-carboxamide

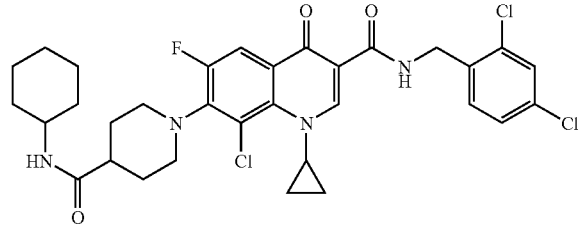

200 mg (0.44 mmol) of the compound of Example 70A and 138 mg (0.66 mmol) of 4-(cyclohexylamino)carbonylpiperidine (for preparation see WO 2003031397) are heated with 91 µl (0.66 mmol) of triethylamine in 4 ml of DMSO at 120° C. for 7 h. After cooling, the entire reaction mixture is separated by preparative HPLC (method 6). 30 mg of the title compound are obtained.

LC-MS (method 3): $R_t$=3.24 min

MS (ES+): m/z=647 (M+H)$^+$

Example 44

8-Chloro-1-cyclopropyl-N-(2,4-dichlorobenzyl)-6-fluoro-7-(4-{[(2-hydroxy-1,1-dimethylethyl)amino]carbonyl}piperidin-1-yl)-4-oxo-1,4-dihydroquinoline-3-carboxamide

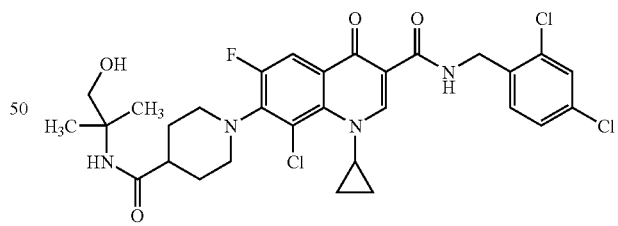

By the same method as for Example 43A, from 200 mg (0.44 mmol) of the compound of Example 70A and 131 mg (0.66 mmol) of 4-{(2-hydroxy-1,1-dimethylethyl)aminocarbonyl}piperidine (for preparation see GB932487 (1960)), 23 mg (8% of theory) of the title compound are obtained.

LC-MS (method 1): $R_t$=2.65 min

MS (ES+): m/z=637 (M+H)$^+$

In analogy to Example 44 Examples 45 and 46 are prepared.

| Example No. | Structure | Starting Material Example No. | Analytical data LC-MS (method)/measurement values HPLC (method)/measurement values MS (method)/measurement values |
|---|---|---|---|
| 45 | 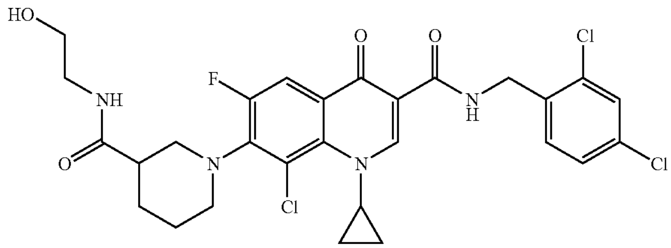 | 70A | LC-MS (method 3): $R_t$ = 2.73 min MS (ES+): m/z = 609 (M + H)+ |
| 46 | 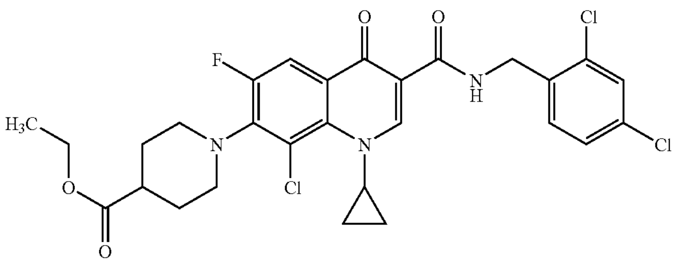 | 70A | LC-MS (method 1): $R_t$ = 3.35 min MS (ES+): m/z = 594 (M + H)+ |

Example 47

1-[6-Fluoro-8-methoxy-3-({[2-methyl-4-(trifluoromethoxy)benzyl]amino}carbonyl)-4-oxo-1-(2,2,2-trifluoroethyl)-1,4-dihydroquinolin-7-yl]piperidine-4-carboxylic acid

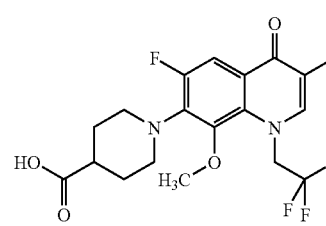

550 mg (0.698 mmol) of the compound of Example 2 are provided in 10 ml of dioxane, 3.5 ml of a 1M solution of lithium hydroxide in water are added and the mixture is stirred overnight. The reaction mixture is acidified with 1N hydrochloric acid and freed from the solvents on a rotary evaporator. The residue is taken up in DMSO and separated by preparative chromatography (method 5). 330 mg (72% of theory) of the title compound are obtained.

HPLC (method 8): $R_t$=4.67 min.

MS (ES+): m/z=634 (M+H)+

$^1$H NMR (400 MHz, CDCl$_3$): δ=1.87-1.99 (m, 2H), 2.08 (br dd, J=3, 13 Hz, 2H), 2.41 (s, 3H), 2.60 (tt, J=4.0, 11.1 Hz, 1H), 3.23 (br. t, J=12 Hz, 2H), 3.50 (br. d, J=12 Hz, 2H), 3.85 (s, 3H), 4.63 (d, J=5.7 Hz, 2H), 5.27 (q, J=8.0 Hz, 2H), 7.00-7.50 (m, 2H), 7.36 (d, J=8.1 Hz, 1H), 7.90 (d, J=12.3 Hz, 1H), 8.62 (s, 1H), 10.10 (t, J=5.7 Hz, 1H).

Example 48

1-[3-({[2-Chloro-4-(trifluoromethoxy)benzyl]amino}carbonyl)-6-fluoro-8-methoxy-4-oxo-1-(2,2,2-trifluoroethyl)-1,4-dihydroquinolin-7-yl]piperidine-4-carboxylic acid

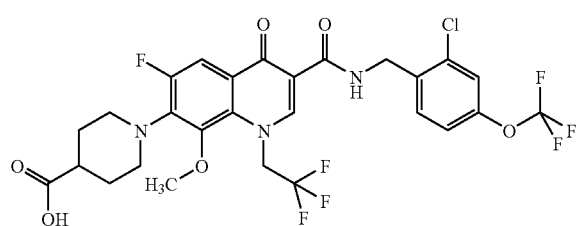

40 mg (0.059 mmol) of the compound of Example 3 are dissolved in 2 ml of dioxane, and 293 μl (5 eq.) of a 1M solution of lithium hydroxide are added, and the mixture is stirred at RT until the reaction is complete (2 days). The reaction mixture is acidified with 1N hydrochloric acid, a little DMSO is added, and the entire crude solution is separated by preparative HPLC (method 5). 25 mg (65% of theory) of the title compound are obtained.

LC-MS (method 1): $R_t$=2.95 min.

MS (ESI pos): m/z=654 (M+H)+

$^1$H NMR (400 MHz, CDCl$_3$): δ=1.87-1.99 (m, 2H), 2.04-2.13 (m, 2H), 2.60 (m, 1H), 3.23 (br. t, J=12 Hz, 2H), 3.51 (br. d, J=12 Hz, 2H), 3.84 (s, 3H), 4.73 (d, J=5.9 Hz, 2H), 5.26 (q, J=8.0 Hz, 2H), 7.10 (d, J=8.5 Hz, 2H), 7.27 (under CHCl$_3$ signal, 1H), 7.49 (d, J=8.6 Hz, 1H), 7.92 (d, J=12.3 Hz, 1H), 8.58 (s, 1H), 10.27 (t, J=5.9 Hz, 1H).

Example 49

1-[6-Fluoro-1-(2-fluoroethyl)-8-methoxy-3-({[2-methyl-4-(trifluoromethoxy)benzyl]amino}carbonyl)-4-oxo-1,4-dihydroquinolin-7-yl]piperidine-4-carboxylic acid

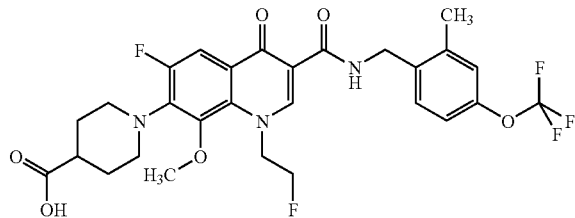

60 mg (0.096 mmol) of the compound of Example 4 are dissolved in 2.35 ml of dioxane, 480 µl (5 eq.) of a 1M solution of lithium hydroxide are added, and the mixture is stirred at RT until the reaction is complete (4 h). The reaction mixture is acidified with 1N hydrochloric acid and diluted with ethyl acetate and water. Following phase separation, the organic phase is washed once again with water and then with a saturated sodium chloride solution, dried over magnesium sulfate and freed from solvents on a rotary evaporator. The residue is dried under high vacuum. 54 mg (94% of theory) of the title compound are obtained.

LC-MS (method 3): $R_t$=2.76 min.
MS (ESI pos): m/z=598 (M+H)$^+$
$^1$H NMR (400 MHz, DMSO-d$_6$): δ=1.70 (br q, J=11 Hz, 2H), 1.91 (br d, J=11 Hz, 2H), 2.36 (s, 3H), 2.48 (m, 1H), 3.15 (br. t, J=11.5 Hz, 2H), 3.42 (br. d, J=12 Hz, 2H), 3.76 (s, 3H), 4.53 (d, J=5.7 Hz, 2H), 4.73 (br d, J=47 Hz, 2H), 4.78 (br d, J=38 Hz, 2H), 7.17 (br d, J=8.5 Hz, 1H), 7.22 (br s, 1H), 7.36 (d, J=8.5 Hz, 1H), 7.78 (d, J=12.5 Hz, 1H), 8.71 (s, 1H), 10.19 (t, J=5.7 Hz, 1H), 12.3 (br.s, 1H).

Example 50

1-[3-{[(2,4-Dichlorobenzyl)amino]carbonyl}-6-fluoro-8-methoxy-4-oxo-1-(2,2,2-trifluoroethyl)-1,4-dihydroquinolin-7-yl]piperidine-4-carboxylic acid

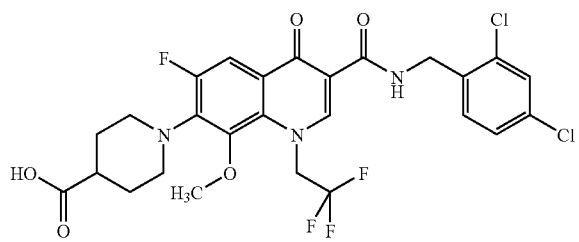

In analogy to Example 49, from 225 mg (0.356 mmol) of the compound of Example 1, by hydrolysis, 200 mg (88% of theory) of the title compound are prepared.

HPLC (method 7): $R_t$=4.86 min.
MS (ES+): m/z=604 (M+H)$^+$
$^1$H NMR (400 MHz, CDCl$_3$): δ=1.86-1.99 (m, 2H), 2.03-2.12 (m, 2H), 2.52 (m, 1H), 3.22 (br t, J=12 Hz, 2H), 3.50 (br d, J=12.3 Hz, 2H), 3.84 (s, 3H), 4.70 (d, J=6.0 Hz, 2H), 5.27 (q, J=8 Hz, 2H), 7.21 (dd, J=2.0, 8.3 Hz, 1H), 7.385 (d, J=8 Hz, 1H), 7.392 (d, J=2 Hz, 1H), 7.92 (d, J=12.4 Hz, 1H), 8.60 (s, 1H), 10.25 (t, J=6.0 Hz, 1H).

Example 51

[3-{[(2,4-Dichlorobenzyl)amino]carbonyl}-6-fluoro-8-methoxy-4-oxo-1-(2,2,2-trifluoroethyl)-1,4-dihydroquinolin-7-yl]piperidin-3-ylacetic acid

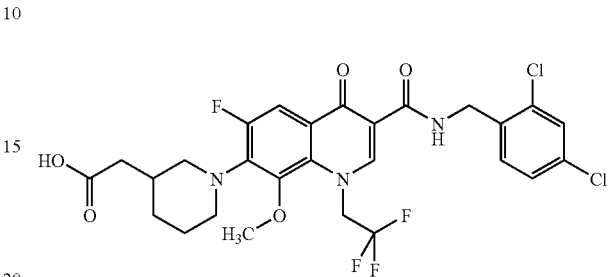

40 mg (0.062 mmol) of the compound of Example 6 are provided in 3 ml of THF/water 5:1, 7.4 mg of LiOH (0.31 mmol, 5 eq.) are added and the reaction mixture is stirred at 50° C. for 10 h. The solvents are removed on a rotary evaporator and the residue is stirred with 1N HCl. The precipitated product is collected by suction filtration and dried under HV. 39 mg of the title compound are obtained (quantitative).

LC-MS (method 1): $R_t$=2.99 min
MS (ES+): m/z=618 (M+H)$^+$
$^1$H NMR (400 MHz, DMSO-d$_6$): δ=1.18-1.26 (m, 1H), 1.60-1.78 (m, 2H), 1.84 (m, 1H), 2.05 (m, 1H), 2.13-2.27 (m, 2H), 2.87 (br.t, J=10.5 Hz, 1H), 3.08 (br.t, J=11.5 Hz, 1H), 3.38 (1H ?, under water signal), 3.78 (s, 3H), 4.60 (d, J=6.0 Hz, 2H), 5.70 (m, 2H), 7.38-7.45 (m, 2H), 7.64 (d, J=1.7 Hz, 1H), 7.77 (d, J=12.1 Hz, 1H), 8.83 (s, 1H), 10.14 (t, J=6.0 Hz, 1H), 12.1 (br s, 1H).

Example 52

1-[3-{[(2,4-Dichlorobenzyl)amino]carbonyl}-6-fluoro-1-[(1S,2R)-2-fluorocyclopropyl]-8-methoxy-4-oxo-1,4-dihydroquinolin-7-yl]piperidine-4-carboxylic acid

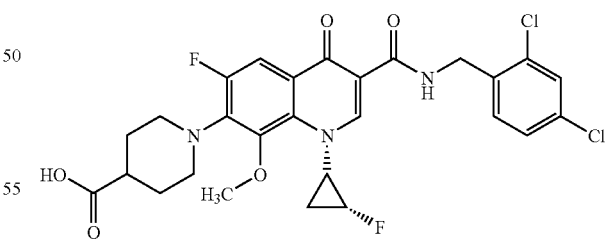

This compound is prepared from Example 13 (32 mg, 0.053 mmol) by the method described for Example 51. 30 mg (98% of theory) of the title compound are obtained.

LC-MS (method 1): $R_t$=2.70 min
MS (ES+): m/z=580 (M+H)$^+$
$^1$H NMR (400 MHz, DMSO-d$_6$): δ=1.45-1.65 (m, 2H), 1.65-1.80 (m, 2H), 1.95 (br. d, J=12.5 Hz, 2H), 2.49 (m, 1H), 3.10-3.24 (m, 2H), 3.35-3.48 (m, 2H), 3.78 (s, 3H), 4.08 (m, 1H), 4.53-4.63 (m, 2H), 5.01 (dq, J=65.2, ~3 Hz, 1H), 7.35-

7.45 (m, 2H), 7.64 (d, J=1.9 Hz, 1H), 7.73 (d, J=12.5 Hz, 1H), 8.67 (s, 1H), 10.31 (t, J=6.0 Hz, 1H), 12.3 (br s, 1H).

Example 53

[6-Fluoro-8-methoxy-3-({[2-methyl-4-(trifluoromethoxy)benzyl]amino}carbonyl)-4-oxo-1-(2,2,2-trifluoroethyl)-1,4-dihydroquinolin-7-yl]piperidin-4-ylacetic acid

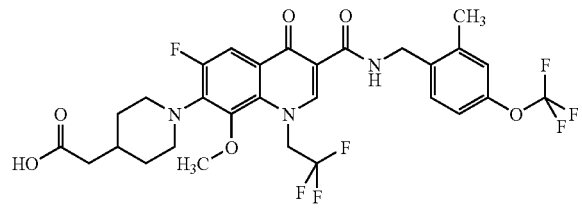

60 mg (0.089 mmol) of the compound of Example 5 are stirred in 2.2 ml of dioxane and 444 µl of LiOH 1M (5 eq.) in water at RT overnight. The mixture is acidified with 1N HCl and diluted with ethyl acetate. It is extracted by shaking twice with water and once with a saturated NaCl solution. The organic phase is dried over magnesium sulfate and freed from the solvent on a rotary evaporator. The residue is dried under HV. 57 mg of the title compound (94% of theory) are obtained.

LC-MS (method 3): $R_t$=3.01 min.

MS (ESI pos): m/z=648 (M+H)$^+$ $^1$H NMR (400 MHz, CDCl$_3$): δ=1.49 (m, 2H), 1.87 (br. d, J=11 Hz, 2H), 2.05 (m, 1H), 2.39 (d, J=7.0 Hz, 2H), 2.40 (s, 3H), 3.21 (br. t, J=12.2 Hz, 2H), 3.46 (br. d, J~12.5 Hz, 2H), 3.81 (s, 3H), 4.62 (d, J=5.6 Hz, 2H), 5.26 (q, J=8.0 Hz, 2H), 7.00-7.04 (m, 2H), 7.36 (d, J=8.0 Hz, 1H), 7.88 (d, J=12.5 Hz, 1H), 8.59 (s, 1H), 10.10 (t, J=5.6 Hz, 1H).

In analogy to Example 47 the following carboxylic acids of Examples 54 to 71 are prepared from the corresponding esters.

| Example No. | Structure | Starting Material Example No. | Analytical data LC-MS (method)/measurement values HPLC (method)/measurement values MS (method)/measurement values |
|---|---|---|---|
| 54 | 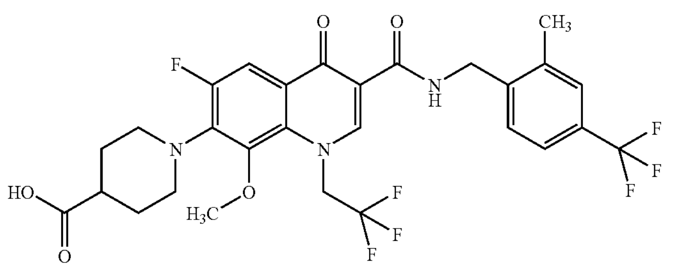 | 8 | LC-MS (method 1): $R_t$ = 2.82 min MS (ES+): m/z = 618 (M + H)$^+$ |
| 55 | 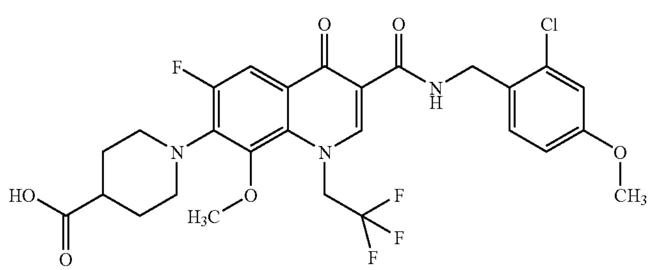 | 9 | LC-MS (method 1): $R_t$ = 2.65 min MS (ES+): m/z = 600 (M + H)$^+$ |
| 56 | 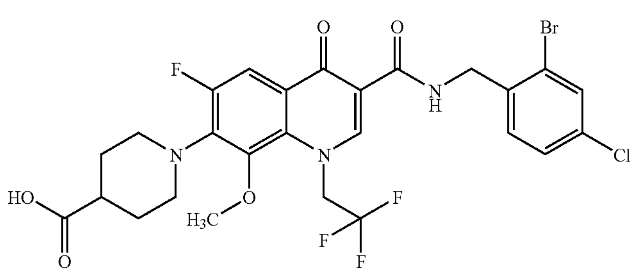 | 10 | LC-MS (method 1): $R_t$ = 2.92 min MS (ES+): m/z = 649/651 (M + H)$^+$ |

-continued

| Example No. | Structure | Starting Material Example No. | Analytical data LC-MS (method)/measurement values HPLC (method)/measurement values MS (method)/measurement values |
|---|---|---|---|
| 57 | 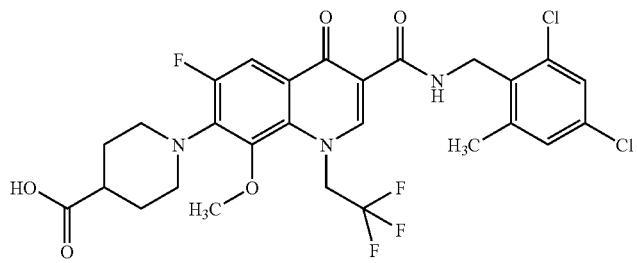 | 11 | LC-MS (method 1):<br>$R_t$ = 2.92 min<br>MS (ES+): m/z = 618 (M + H)$^+$ |
| 58 | 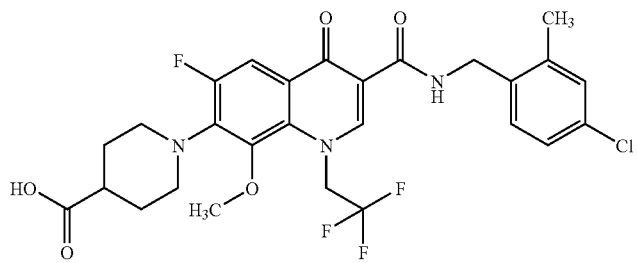 | 7 | HPLC (method 7):<br>$R_t$ = 4.77 min<br>MS (ES+): m/z = 584 (M + H)$^+$ |
| 59 | 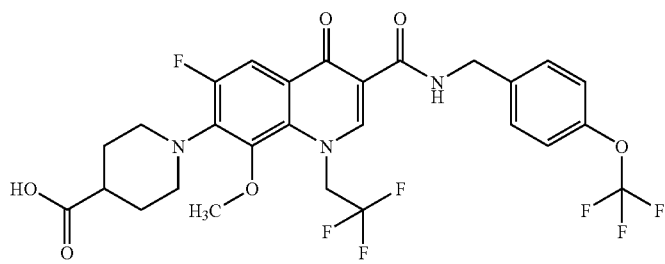 | 12 | LC-MS (method 2):<br>$R_t$ = 2.61 min<br>MS (ES+): m/z = 620 (M + H)$^+$ |
| 60 | 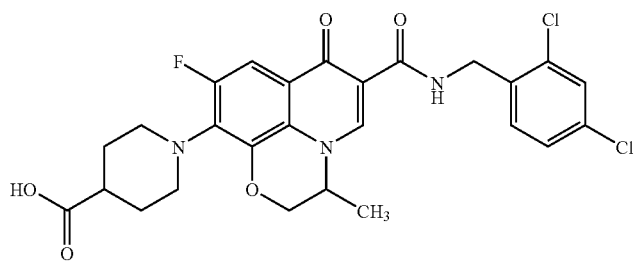 | 14 | LC-MS (method 3):<br>$R_t$ = 2.67 min<br>MS (ES+): m/z = 548 (M + H)$^+$ |
| 61 | 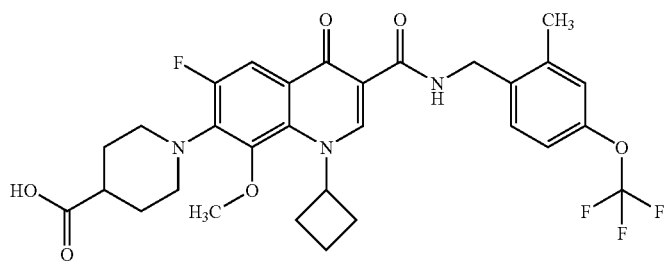 | 15 | LC-MS (method 3):<br>$R_t$ = 2.97 min<br>MS (ES+): m/z = 606 (M + H)$^+$ |

-continued

| Example No. | Structure | Starting Material Example No. | Analytical data LC-MS (method)/measurement values HPLC (method)/measurement values MS (method)/measurement values |
|---|---|---|---|
| 62 | 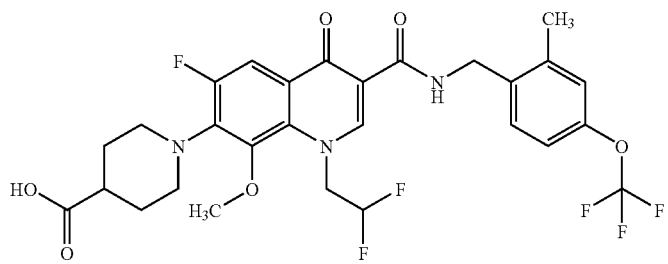 | 17 | LC-MS (method 2):<br>$R_t$ = 2.59 min<br>MS (ES+): m/z = 616 (M + H)$^+$ |
| 63 | 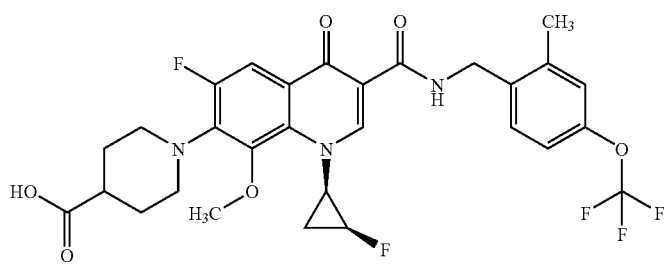 | 16 | LC-MS (method 3):<br>$R_t$ = 2.81 min<br>MS (ES+): m/z = 610 (M + H)$^+$ |
| 64 | 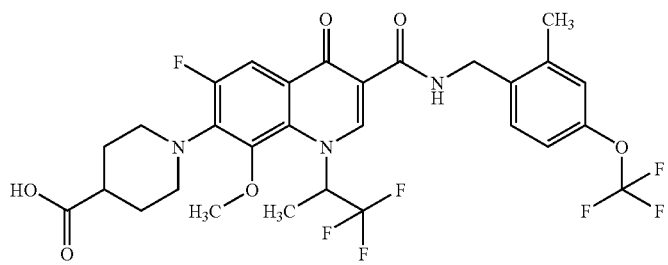 | 18 | LC-MS (method 2):<br>$R_t$ = 2.79 min<br>MS (ES+): m/z = 648 (M + H)$^+$ |
| 65 | 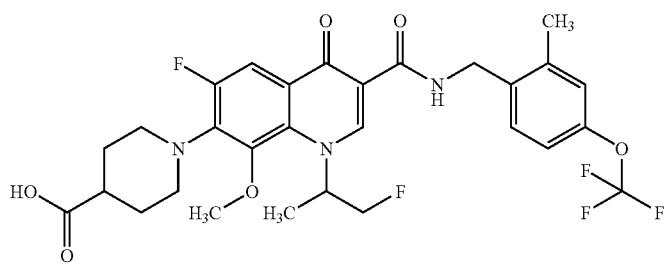 | 19 | LC-MS (methody 2):<br>$R_t$ = 2.60 min<br>MS (ES+): m/z = 612 (M + H)$^+$ |
| 66 | 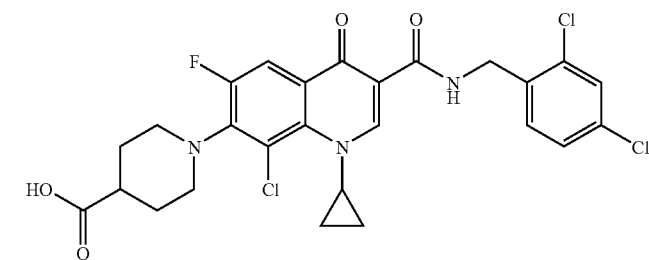 | 45 | LC-MS (method 2):<br>$R_t$ = 2.67 min<br>MS (ES+): m/z = 566 (M + H)$^+$ |

-continued

| Example No. | Structure | Starting Material Example No. | Analytical data LC-MS (method)/measurement values HPLC (method)/measurement values MS (method)/measurement values |
|---|---|---|---|
| 67 | 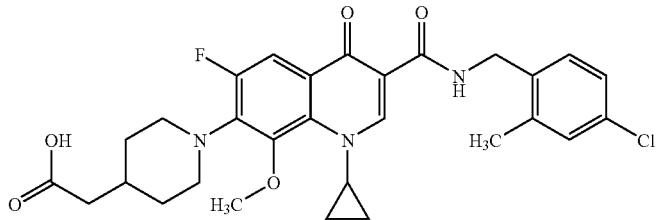 | 24 | LC-MS (method 1): $R_t$ = 2.75 min MS (ES+): m/z = 556 (M + H)$^+$ |
| 68 | 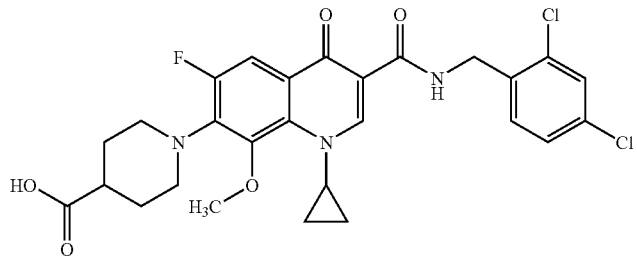 | 26 | LC-MS (method 1): $R_t$ = 2.76 min MS (ES+): m/z = 592 (M + H)$^+$ |
| 69 | 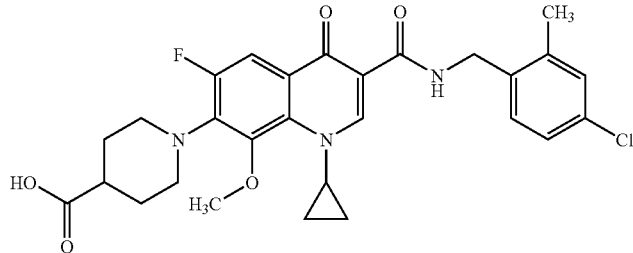 | 22 | LC-MS (method 1): $R_t$ = 2.67 min MS (ES+): m/z = 542 (M + H)$^+$ |
| 70 | 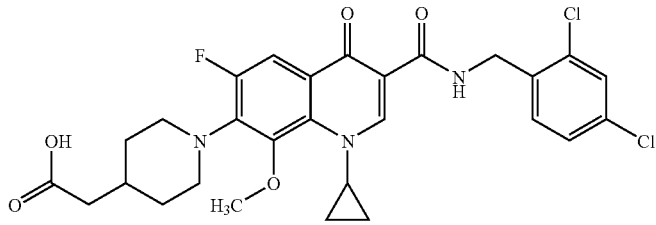 | 23 | LC-MS (method 1): $R_t$ = 2.84 min MS (ES+): m/z = 576 (M + H)$^+$ |
| 71 | 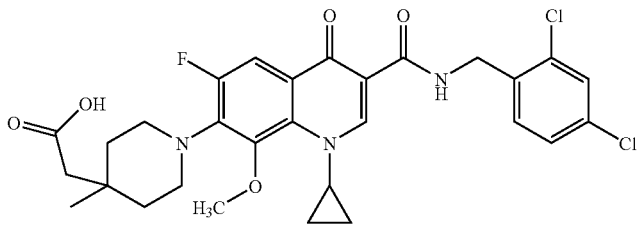 | 25 | LC-MS (method 2): $R_t$ = 2.37 min MS (ES+): m/z = 592 (M + H)$^+$ |

Example 72

{(3S)-1-[6-Fluoro-8-methoxy-3-({[2-methyl-4-(trifluoromethoxy)benzyl]amino}carbonyl)-4-oxo-1-(2,2,2-trifluoroethyl)-1,4-dihydroquinolin-7-yl]piperidin-3-yl}acetic acid

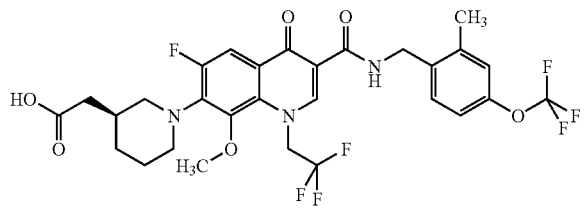

72 mg (0.107 mmol) of the compound of Example 20 are stirred with 2.6 ml of dioxane and 533 μl of LiOH (1M solution in water, 5 eq.) at RT overnight. The mixture is acidified with 1N HCl and diluted with ethyl acetate. It is extracted by shaking twice with water and once with a saturated NaCl solution. The organic phase is dried over magnesium sulfate and freed from the solvent on a rotary evaporator. The residue is dried under HV. 70 mg of the title compound (99% of theory) are obtained.

LC-MS (method 3): $R_t$=3.07 min
MS (ES+): m/z=648 (M+H)$^+$ $^1$H NMR (400 MHz, CDCl$_3$): δ=10.17 (t, J=5.6 Hz, 1H), 8.74 (s, 1H), 7.87 (d, J=12.4 Hz, 1H), 7.35 (d, J=8.1 Hz, 1H), 7.04-7.00 (m, 2H), 5.42-5.24 (m, 2H), 4.62 (d, J=5.6 Hz, 2H), 3.87 (s, 3H), 3.53 (br. d, J~11.5 Hz, 1H), 3.38 (br. d, J~12 Hz, 1H), 3.17 (br.t, J~12 Hz, 1H), 2.84 (br.t, J~11 Hz, 1H), 2.41 (s, 3H), 2.36-2.31 (m, 2H), 2.31-2.22 (m, 1H), 2.00-1.92 (m, 1H), 1.85-1.72 (m, 2H), 1.30-1.20 (m, 1H).

Example 73

{(3R)-1-[6-Fluoro-8-methoxy-3-({[2-methyl-4-(trifluoromethoxy)benzyl]amino}carbonyl)-4-oxo-1-(2,2,2-trifluoroethyl)-1,4-dihydroquinolin-7-yl]piperidin-3-yl}acetic acid

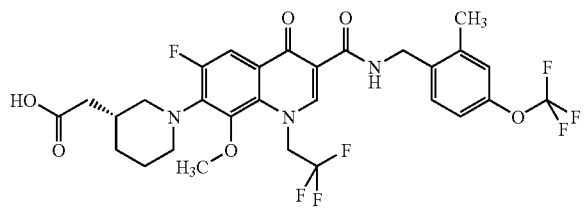

83 mg (0.123 mmol) of the compound of Example 21 are stirred with 3.0 ml of dioxane and 614 μl of LiOH (1M solution in water, 5 eq.) at RT overnight. The mixture is acidified with 1N HCl and diluted with ethyl acetate. It is extracted by shaking twice with water and once with a saturated NaCl solution. The organic phase is dried over magnesium sulfate and freed from the solvent on a rotary evaporator. The residue is dried under HV. 73 mg of the title compound (90% of theory) are obtained.

LC-MS (method 3): $R_t$=3.07 min
MS (ES+): m/z=648 (M+H)$^+$ $^1$H NMR (400 MHz, CDCl$_3$): δ=10.17 (t, J=5.6 Hz, 1H), 8.74 (s, 1H), 7.87 (d, J=12.4 Hz, 1H), 7.35 (d, J=8.1 Hz, 1H), 7.04-7.00 (m, 2H), 5.42-5.24 (m, 2H), 4.62 (d, J=5.6 Hz, 2H), 3.87 (s, 3H), 3.53 (br. d, J~11.5 Hz, 1H), 3.38 (br. d, J~12 Hz, 1H), 3.17 (br.t, J~12 Hz, 1H), 2.84 (br.t, J~11 Hz, 1H), 2.41 (s, 3H), 2.36-2.31 (m, 2H), 2.31-2.22 (m, 1H), 2.00-1.92 (m, 1H), 1.85-1.72 (m, 2H), 1.30-1.20 (m, 1H).

The absolute stereochemistry is confirmed by an X-ray structural analysis.

Example 74

8-Chloro-1-cyclopropyl-N-(2,4-dichlorobenzyl)-6-fluoro-4-oxo-7-(3-oxo-2,8-diazaspiro[4.5]dec-8-yl)-1,4-dihydroquinoline-3-carboxamide

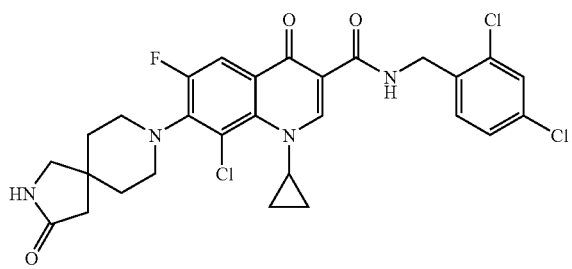

60 mg (0.13 mmol) of the compound of Example 70A and 37 mg (0.20 mmol) of 3-oxo-2,8-diazaspiro[4,5]decane hydrochloride (Example 13A) are stirred with 91 μl (0.52 mmol) of N,N-diisopropylethylamine in 2 ml of DMSO at 120° C. for 2 days. After cooling, the entire reaction mixture is separated by preparative HPLC (method 5). Concentration of the appropriate fractions on a rotary evaporator and drying under high vacuum give 20 mg (26% of theory) of the title compound.

LC-MS (method 3): $R_t$=2.73 min
MS (ES+): m/z=592 (M+H)$^+$.

$^1$H NMR (400 MHz, CDCl$_3$): δ=0.88-0.95 (m, 3H), 1.20-1.26 (m, 2H), 1.85-1.91 (m, 4H), 2.34 (s, 2H), 3.31 (br.s, 6H), 4.27 (m, 1H), 4.69 (d, J=6.2 Hz, 2H), 5.44 (br s, 1H), 7.21 (dd, J=2.0, 8.3 Hz, 1H), 7.37-7.40 (m, 2H), 8.01 (d, J=12.1 Hz, 1H), 8.92 (s, 1H), 10.20 (t, J=6.2 Hz, 1H).

Example 75

1-[6-Fluoro-8-methoxy-3-({[2-methyl-4-(trifluoromethoxy)benzyl]amino}carbonyl)-4-oxo-1-(2,2,2-trifluoroethyl)-1,4-dihydroquinolin-7-yl]piperidine-4-carboxylic acid diethanolamine salt

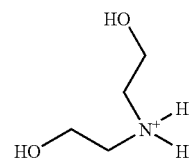

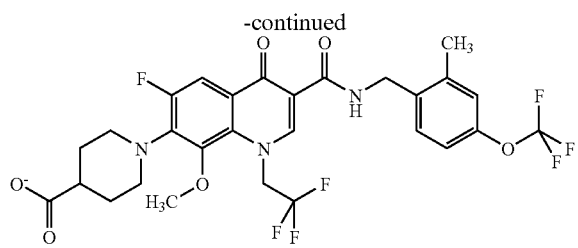

400 mg (0.63 mmol) of 1-[6-fluoro-8-methoxy-3-({[2-methyl-4-(trifluoromethoxy)benzyl]amino}carbonyl)-4-oxo-1-(2,2,2-trifluoroethyl)-1,4-dihydroquinolin-7-yl]piperidine-4-carboxylic acid (Example 47) are suspended in 20 ml of deionized water and 20 ml of acetonitrile at RT. 60.5 μl (66.4 mg, 0.63 mmol) of diethanolamine are added and the mixture is stirred at RT overnight. The resulting solution is freed from the acetonitrile on a rotary evaporator. The aqueous solution which remains was frozen and lyophilized. 475 mg (100% of theory) of residue, which is found by analysis to correspond to the title compound, are obtained $^1$H NMR (400 MHz, CDCl$_3$): δ=1.77-1.90 (m, 2H), 2.01 (br d, J=13 Hz, 2H), 2.38 (m, 1H), 2.40 (s, 3H), 3.03-3.09 (m, 4H), 3.18 (br. t, J=12 Hz, 2H), 3.49 (br. d, J=12 Hz, 2H), 3.83 (s, 3H), 3.86-3.89 (m, 4H), 4.62 (d, J=5.7 Hz, 2H), 5.27 (q, J=8.0 Hz, 2H), 6.99-7.05 (m, 2H), 7.35 (d, J=8.1 Hz, 1H), 7.86 (d, J=12.5 Hz, 1H), 8.57 (s, 1H), 10.10 (t, J=5.7 Hz, 1H).

Example 76

1-[6-Fluoro-8-methoxy-3-({[2-methyl-4-(trifluoromethoxy)benzyl]amino}carbonyl)-4-oxo-1-(2,2,2-trifluoroethyl)-1,4-dihydroquinolin-7-yl]piperidine-4-carboxylic acid choline salt

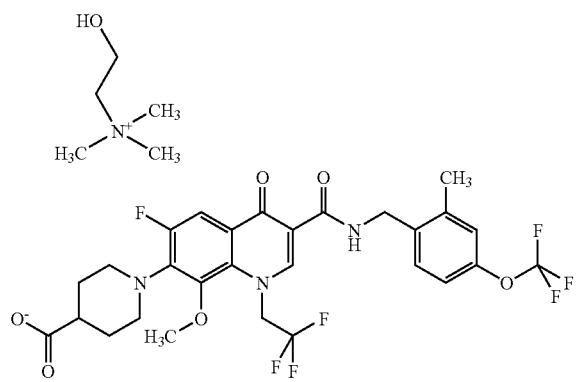

400 mg (0.63 mmol) of 1-[6-fluoro-8-methoxy-3-({[2-methyl-4-(trifluoromethoxy)benzyl]amino}carbonyl)-4-oxo-1-(2,2,2-trifluoroethyl)-1,4-dihydroquinolin-7-yl]piperidine-4-carboxylic acid (Example 47) are suspended in 20 ml of deionized water and 20 ml of acetonitrile at RT. 140 μl (153 mg, 0.63 mmol) of β-hydroxyethyltrimethylammonium hydroxide ("choline hydroxide") are added and the mixture is stirred at RT overnight. The resulting solution is freed from the acetonitrile on a rotary evaporator. The aqueous solution which remains was frozen and lyophilized. 494 mg (100% of theory) of residue, which is found by analysis to correspond to the title compound, are obtained.

$^1$H NMR (400 MHz, CDCl$_3$): δ=1.88 (dq, J~3.8, 12 Hz, 2H), 2.01 (br d, J~12 Hz, 2H), 2.33 (tt, J=3.6, 11.6 Hz, 1H), 2.40 (s, 3H), 3.18 (br. t, J=12 Hz, 2H), 3.49 (br. d, J~12 Hz, 2H), 3.83 (br.s, 2H), 3.835 (s, 3H), 4.22 (br.s, 2H), 4.62 (d, J=5.7 Hz, 2H), 5.27 (q, J=8.0 Hz, 2H), 7.00-7.05 (m, 2H), 7.35 (d, J=8.3 Hz, 1H), 7.845 (d, J=12.5 Hz, 1H), 8.54 (s, 1H), 10.10 (t, J=5.7 Hz, 1H).

Example 77

1-[6-Fluoro-8-hydroxy-3-({[2-methyl-4-(trifluoromethoxy)benzyl]amino}carbonyl)-4-oxo-1-(2,2,2-trifluoroethyl)-1,4-dihydroquinolin-7-yl]piperidine-4-carboxylic acid

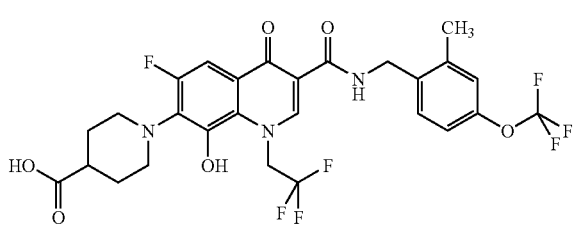

150 mg (0.237 mmol) of the compound of Example 47 are provided in 3 ml of dichloromethane, 943 μl of trimethylsilyliodide (6.63 mmol) are added and the mixture is stirred for 4 days at room temperature. In order to destroy the excess trimethylsilyliodide the reaction mixture is cooled to 0° C., and a mixture of 414 μl of Ethanol (7.1 mmol) and 575 μl of pyridine (7.1 mmol) is added. After 5 min the volatile components are removed on a rotary evaporator. The residue is stirred in 5 ml of a water-acetonitrile mixture (1:1) and the solid is collected by filtration. It is dried under high vacuum. 136 mg of the title compound are obtained (91% of theory).

LC-MS (method 2): R$_t$=2.68 min
MS (ES+): m/z=620 (M+H)$^+$
$^1$H-NMR (400 MHz, CDCl$_3$): δ=10.06 (t, J=5.7 Hz, 1H), 8.69 (br. s, 1H), 8.66 (s, 1H), 7.72 (d, J=11.5 Hz, 1H), 7.36 (d, J=8.1 Hz, 1H), 7.04 (s, 1H), 7.03 (d, J~8 Hz, 1H), 5.38 (q, J=7.8 Hz, 2H), 4.63 (d, J=5.7 Hz, 2H), 3.32 (br. t, J~12 Hz, 2H), 3.02 (br.d, J~12 Hz, 2H), 2.59 (m, 1H), 2.41 (s, 3H), 2.21 (br.d, J~13 Hz, 2H), 1.97-1.83 (m, 2H).

Example 78

Ethyl 1-[8-ethoxy-6-fluoro-3-({[2-methyl-4-(trifluoromethoxy)benzyl]amino}carbonyl)-4-oxo-1-(2,2,2-trifluoroethyl)-1,4-dihydroquinolin-7-yl]piperidine-4-carboxylate

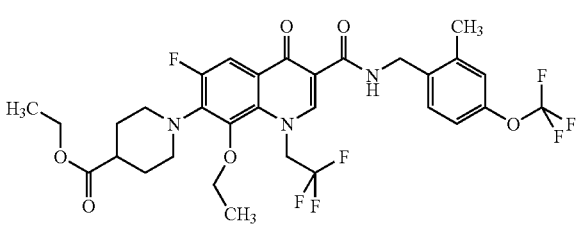

110 mg (0.178 mmol) of the compound of Example 77, 135 mg of potassium carbonate (0.98 mmol) and 142 μl of ethyl iodide (1.78 mmol) are stirred with 2.0 ml of DMF in a closed vessel at 80° C. for 4 h. After cooling to room temperature the mixture is poured onto 30 ml of water. After a short stirring of the suspension the solid is collected by suction filtration, washed with water and dried under high vacuum. 111 mg of the title compound are obtained (93% of theory).

LC-MS (method 1): $R_t$=3.37 min

MS (ES+): m/z=676 (M+H)$^+$ $^1$H-NMR (400 MHz, DMSO-$d_6$): δ=10.02 (t, J=5.8 Hz, 1H), 8.85 (s, 1H), 7.76 (d, J=12.5 Hz, 1H), 7.36 (d, J=8.3 Hz, 1H), 7.22 (s, 1H), 7.17 (d, J~8.7, 1H), 5.75 (q, J=8.6 Hz, 2H), 4.55 (d, J=5.9 Hz, 2H), 4.10 (q, J=7.1 Hz, 2H), 3.99 (q, J=7.1 Hz, 2H), 3.43-3.28 (m, 2H), 3.17 (br.t, J~12 Hz, 2H), ca. 2.55 (m, 1H), 2.37 (s, 3H), 1.93 (br.d, J~12 Hz, 2H), 1.77-1.64 (m, 2H), 1.33 (t, J=7.1 Hz, 3H), 1.20 (t, J=7.1 Hz, 3H).

Example 79

1-[8-Ethoxy-6-fluoro-3-({[2-methyl-4-(trifluoromethoxy)benzyl]amino}carbonyl)-4-oxo-1-(2,2,2-trifluoroethyl)-1,4-dihydroquinolin-7-yl]piperidine-4-carboxylic acid

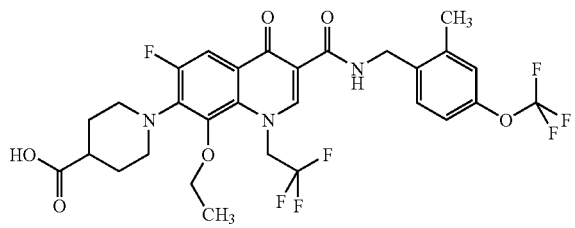

2 ml of methanol, 2.5 ml of DMF and 2 ml of a sodium hydroxide solution (2N) are added to 85 mg (0.126 mmol) of the compound of Example 78. The mixture is stirred for 1 h at room temperature, acidified with 1N-HCl to pH 1, diluted with water and extracted three times with ethyl acetate. The combined organic phases are washed with a saturated sodium chloride solution, dried over sodium sulfate and freed from the solvent on a rotary evaporator. The residue is dried under high vacuum. 81 mg of the title compound are obtained (96% of theory).

LC-MS (method 2): $R_t$=2.78 min

MS (ES+): m/z=648 (M+H)$^+$ $^1$H-NMR (500 MHz, CDCl$_3$): δ=10.11 (t, J=5.4 Hz, 1H), 8.62 (s, 1H), 7.88 (d, J=12.4 Hz, 1H), 7.36 (d, J=8.0 Hz, 1H), 7.05-7.00 (m, 2H), 5.34 (q, J=7.9 Hz, 2H), 4.63 (d, J=5.6 Hz, 2H), 4.02 (q, J=7.0 Hz, 2H), 3.54-3.48 (m, 2H), 3.21 (br.t, J~12 Hz, 2H), 2.58 (m, 1H), 2.41 (s, 3H), 2.11-2.05 (m, 2H), 1.95-1.85 (m, 2H), 1.41 (t, J=7.0 Hz, 3H).

B. Assessment of the Physiological Activity

The in vitro activity of the compounds of the invention can be shown in the following assays:

Anti-HCMV (Anti-Human Cytomegalovirus) Cytopathogenicity Tests

The test compounds are employed as 50 millimolar (mM) solutions in dimethyl sulfoxide (DMSO). Ganciclovir®, Foscarnet® and Cidofovir® are used as reference compounds. After the addition of 2 µl of the 50, 5, 0.5 and 0.05 mM DMSO stock solutions respectively to 98 µl portions of cell culture medium in row 2 A-H for duplicate determinations, 1:2 dilutions are carried out with 50 µl portions of medium up to row 11 of the 96-well plate. The wells in rows 1 and 12 each contain 50 µl of medium. 150 µl of a suspension of 1×10$^4$ cells (human prepuce fibroblasts [NHDF]) are then pipetted into each of the wells (row 1=cell control) and, in rows 2-12, a mixture of HCMV-infected and uninfected NHDF cells (M.O.I.=0.001-0.002), i.e. 1-2 infected cells per 1000 uninfected cells. Row 12 (without substance) serves as virus control. The final test concentrations are 250-0.0005 µM. The plates are incubated at 37° C./5% CO$_2$ for 6 days, i.e. until all the cells in the virus controls are infected (100% cytopathogenic effect [CPE]). The wells are then fixed and stained by adding a mixture of formalin and Giemsa's dye (30 minutes), washed with double-distilled water and dried in a drying oven at 50° C. The plates are then assessed visually using an overhead microscope (plaque multiplier from Technomara).

The following data can be obtained from the test plates:

$CC_{50}$ (NHDF)=substance concentration in µM at which no visible cytostatic effects on the cells are evident compared with the untreated cell control;

$EC_{50}$ (HCMV)=substance concentration in µM which inhibits the CPE (cytopathic effect) by 50% compared with the untreated virus control;

SI (selectivity index)=$CC_{50}$ (NHDF)/$EC_{50}$ (HCMV).

Representative in vitro activity data for the compounds of the invention are shown in Table A:

TABLE A

| Example No. | HCMV $EC_{50}$ [µM] | NHDF $CC_{50}$ [µM] |
|---|---|---|
| 1 | 0.009 | 94 |
| 2 | 0.005 | 47 |
| 3 | 0.008 | 24 |
| 7 | 0.018 | 94 |
| 13 | 0.019 | 23 |
| 27 | 0.013 | 21 |
| 28 | 0.014 | 21 |
| 30 | 0.034 | 11 |
| 31 | 0.008 | 16 |
| 32 | 0.017 | 11 |
| 33 | 0.017 | 19 |
| 34 | 0.040 | 11 |
| 36 | 0.014 | 21 |
| 47 | 0.004 | 86 |
| 48 | 0.003 | 20 |
| 49 | 0.006 | 94 |
| 50 | 0.012 | 47 |
| 51 | 0.026 | 47 |
| 53 | 0.005 | 94 |
| 54 | 0.022 | 21 |
| 55 | 0.031 | 16 |
| 57 | 0.026 | 23 |
| 58 | 0.006 | 47 |
| 61 | 0.007 | 21 |
| 62 | 0.001 | 148 |
| 63 | 0.008 | 47 |
| 65 | 0.079 | 106 |
| 67 | 0.061 | 21 |
| 73 | 0.003 | 47 |
| 75 | 0.002 | 47 |
| 76 | 0.002 | 47 |
| 77 | 0.006 | 250 |
| 79 | 0.002 | 125 |

The suitability of the compounds of the invention for the treatment of HCMV infections can be shown in the following animal model:

HCMV Xenograft Gelfoam® Model

Animals:

5-6-week-old immunodeficient mice (16-20 g), Fox Chase SCID.NOD or NOD.CB17-Prkdc/J, are purchased from commercial breeders (Taconic M&B, Denmark; Jackson, USA). The animals are kept under sterile conditions (including bedding and feed) in isolators.

Virus Growing:

Human cytomegalovirus (HCMV), Davis or AD169 strain, is grown in vitro on human embryonic prepuce fibroblasts (NHDF cells). After the NHDF cells have been infected with a multiplicity of infection (M.O.I.) of 0.01-0.03, the virus-infected cells are harvested 5-10 days later and stored in the presence of minimal essential medium (MEM), 20% foetal calf serum (FCS) (v/v), 1% glutamine (v/v), 1% Pen/Strep (v/v) with 10% DMSO at −80° C. After serial ten-fold dilutions of the virus-infected cells, the titre is determined on 24-well plates of confluent NHDF cells after fixing and staining with a Giemsa formaldehyde solution.

Preparation of the Sponges, Transplantation, Treatment and Evaluation:

Collagen sponges 1×1×1 cm in size (Gelfoam®; Peasel & Lorey, order no. 407534; K. T. Chong et al., Abstracts of 39$^{th}$ Interscience Conference on Antimicrobial Agents and Chemotherapy, 1999, p. 439) are initially wetted with phosphate-buffered saline (PBS), the trapped air bubbles are removed by degassing, and then stored in MEM, 10% FCS (v/v), 1% glutamine (v/v), 1% Pen/Strep (v/v). $1\times10^6$ virus-infected NHDF cells (infection with HCMV Davis or HCMV AD169 M.O.I=0.03) are detached 3 hours after infection and added dropwise in 20 μl of MEM, 10% FCS (v/v), 1% glutamine (v/v), 1% Pen/Strep (v/v) onto a moist sponge. The sponges are incubated for 3-4 hours to allow the cells to adhere. Then, following the addition of medium (MEM, 10% FCS) (v/v), 1% glutamine (v/v), 1% Pen/Strep (v/v)), the sponges are incubated overnight. For the transplantation, the immunodeficient mice are anaesthetized with Avertin or a ketamine/xylazine/azepromazine mixture, the fur on the back is removed using a shaver, the epidermis is opened 1-2 cm, unstressed and the moist sponges are transplanted under the dorsal skin. The surgical wound is closed with tissue glue or clips. 4-6 hours after the transplantation, the mice can be treated for the first time (one treatment is given on the day of the operation). On subsequent days, oral treatment with the substance is carried out three times a day (7.00 h and 14.00 h and 19.00 h), twice a day (8 h and 18 h) or once a day (9 h) over a period of 8 days. The daily dose is for example 1 or 3 or 10 or 30 or 100 mg/kg of body weight, the volume administered is 10 ml/kg of body weight. The substances are formulated in the form of a 0.5% Tylose suspension/PBS with 2% DMSO or another suitable mixture aiding the solubility of the substances, e.g. 2% ethanol, 2.5% Solutol, 95.5% PBS. 10 days after transplantation and about 16 hours after the last administration of substance, the animals are painlessly sacrificed and the sponge is removed. The virus-infected cells are released from the sponge by collagenase digestion (330 U/1.5 ml) and stored in the presence of MEM, 10% FCS (v/v), 1% glutamine (v/v), 1% Pen/Strep (v/v), 10% DMSO at −140° C. Evaluation takes place after serial ten-fold dilutions of the virus-infected cells by determining the titre on 24-well plates of confluent NHDF cells after fixing and staining with a Giemsa formaldehyde solution. The number of infected cells or infectious virus particles (infectious centre assay) after the substance treatment compared with the placebo-treated control group is determined. Statistical evaluation takes place by suitable computer programs, such as GraphPad Prism.

hERG Binding Assay:

The hERG binding for compounds can be measured in a [$^3$H]-astemizole binding assay in HEK293 cells, as described in the following publication: Peter J. S. Chiu et al., J. Pharmacol. Sci. 95, 311-19 (2004).

C. Exemplary Embodiments of Pharmaceutical Compositions

The compounds of the invention can be converted into pharmaceutical preparations in the following ways:

Tablet:
Composition:

100 mg of the compound of Example 1, 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg. Diameter 8 mm, radius of curvature 12 mm.

Production:

The mixture of active ingredient, lactose and starch is granulated with a 5% solution (m/m) of the PVP in water. The granules are then dried and mixed with the magnesium stearate for 5 min. This mixture is compressed using a conventional tablet press (see above for format of the tablet). A guideline for the compressive force used for the compression is 15 kN.

Suspension which can be Administered Orally:
Composition:

1000 mg of the compound of Example 1, 1000 mg of ethanol (96%), 400 mg of Rhodigel (xanthan gum, FMC, Pennsylvania, USA) and 99 g of water.

10 ml of oral suspension are equivalent to a single dose of 100 mg of the compound of the invention.

Production:

The Rhodigel is suspended in ethanol, and the active ingredient is added to the suspension. The water is added while stirring. The mixture is stirred for about 6 h until the swelling of the Rhodigel is complete.

Solution which can be Administered Intravenously:
Composition:

10-500 mg of the compound of Example 1, 15 g of polyethylene glycol 400 and 250 g of water for injections.

Production:

The compound of Example 1 is dissolved together with polyethylene glycol 400 in the water with stirring. The solution is sterilized by filtration (pore diameter 0.22 μm) and dispensed under aseptic conditions into heat-sterilized infusion bottles. The latter are closed with infusion stoppers and crimped caps.

The invention claimed is:

1. A compound of formula

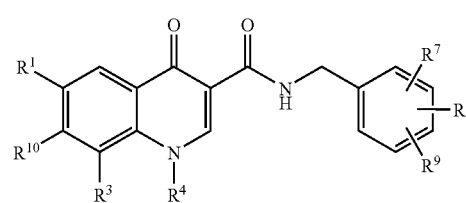

in which
R$^1$ represents hydrogen, fluorine, chlorine or trifluoromethyl,
R$^3$ represents halogen, hydroxy, C$_1$-C$_4$-alkoxy, cyano, trifluoromethyl, monofluoromethoxy, difluoromethoxy, trifluoromethoxy or ethynyl,
R$^4$ represents C$_1$-C$_6$-alkyl or C$_3$-C$_8$-cycloalkyl,
whereby alkyl can be substituted with 1 to 3 substituents, whereby the substituents are selected independently of one another from the group consisting of halogen, hydroxy, amino, cyano, trifluoromethyl, hydroxycarbonyl, aminocarbonyl, $C_1$-$C_6$-alkoxy, $C_1$-$C_6$-alkylamino, $C_1$-$C_6$-alkylcarbonyl and $C_1$-$C_6$-alkoxycarbonyl,
and
whereby cycloalkyl can be substituted with 1 to 3 substituents, whereby the substituents are selected independently of one another from the group consisting of halogen, hydroxy, amino, cyano, trifluoromethyl, hydroxycarbonyl, aminocarbonyl, $C_1$-$C_6$-alkyl, $C_1$-$C_6$-alkoxy, $C_1$-$C_6$-alkylamino, $C_1$-$C_6$-alkylcarbonyl and $C_1$-$C_6$-alkoxycarbonyl,
or
$R^3$ and $R^4$, together with the atoms to which they are attached, form a ring through a group of formula

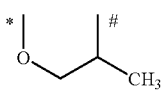

whereby
* is the linkage site to the carbon atom,
and
# is the linkage site to the nitrogen atom,
$R^7$ and $R^8$ independently of one another represent halogen, hydroxy, cyano, trifluoromethyl, monofluoromethoxy, difluoromethoxy, trifluoromethoxy, $C_1$-$C_3$-alkyl or $C_1$-$C_3$-alkoxy,
and
$R^9$ represents hydrogen, halogen, hydroxy, cyano, trifluoromethyl, monofluoromethoxy, difluoromethoxy, trifluoromethoxy, $C_1$-$C_3$-alkyl or $C_1$-$C_3$-alkoxy,
or
$R^8$ represents trifluoromethoxy,
and
$R^7$ and $R^9$ represent hydrogen,
$R^{10}$ represents a group of formula

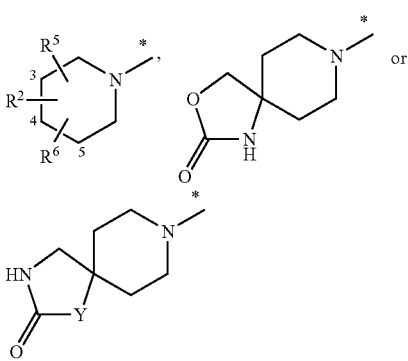

whereby
* is the linkage site to the carbon atom,
$R^2$ is attached at position 3 or 4 and represents hydroxy, hydroxycarbonyl, aminocarbonyl, $C_1$-$C_4$-alkyl, $C_1$-$C_4$-alkoxycarbonyl, $C_3$-$C_6$-cycloalkylaminocarbonyl or optionally hydroxy-substituted $C_1$-$C_6$-alkylaminocarbonyl,
whereby alkyl is substituted with a substituent, whereby the substituent is selected from the group consisting of hydroxy, hydroxycarbonyl, aminocarbonyl, $C_1$-$C_4$-alkoxycarbonyl and 2-oxopyrrolidin-1-yl, $R^5$ and $R^6$ independently of one another are attached at position 3, 4 or 5 and independently of one another represent hydrogen, hydroxy, methyl, or ethyl,
and
Y represents a methylene group or an oxygen atom, or one of its salts.

2. The compound of claim 1, conforming to formula

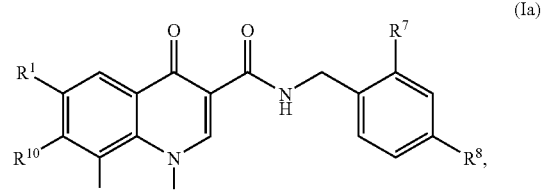

in which
$R^1$ represents hydrogen, fluorine, chlorine or trifluoromethyl,
$R^3$ represents halogen, hydroxy, Ci-C4-alkoxy, cyano, trifluoromethyl, monofluoromethoxy, difluoromethoxy, trifluoromethoxy or ethynyl,
$R^4$ represents $C_1$-$C_6$-alkyl or $C_3$-$C_8$-cycloalkyl,
whereby alkyl can be substituted with 1 to 3 substituents, whereby the substituents are selected independently of one another from the group consisting of halogen, hydroxy, amino, cyano, trifluoromethyl, hydroxycarbonyl, aminocarbonyl, $C_1$-$C_6$-alkoxy, $C_1$-$C_6$-alkylamino, $C_1$-$C_6$-alkylcarbonyl and $C_1$-$C_6$-alkoxycarbonyl,
and
whereby cycloalkyl can be substituted with 1 to 3 substituents, whereby the substituents are selected independently of one another from the group consisting of halogen, hydroxy, amino, cyano, trifluoromethyl, hydroxycarbonyl, aminocarbonyl, $C_1$-$C_6$-alkyl, $C_1$-$C_6$-alkoxy, $C_1$-$C_6$-alkylamino, $C_1$-$C_6$-alkylcarbonyl and $C_1$-$C_6$-alkoxycarbonyl,
or
$R^3$ and $R^4$, together with the atoms to which they are attached, form a ring through a group of formula

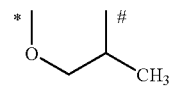

where
* is the linkage site to the carbon atom,
and
# is the linkage site to the nitrogen atom,
$R^7$ and $R^8$ independently of one another represent halogen, hydroxy, cyano, trifluoromethyl, monofluoromethoxy, difluoromethoxy, trifluoromethoxy, $C_1$-$C_3$-alkyl or $C_1$-$C_3$-alkoxy, $R^{10}$ represents a group of formula

[Chemical structures: a piperidine ring with $R^5$, $R^2$, $R^6$ substituents linked via N; an oxa-diazaspiro structure with N-methyl; and a diazaspiro structure with Y and HN-C(=O)]

whereby
* is the linkage site to the carbon atom,
$R^2$ is attached at position 3 or 4 and represents hydroxy, hydroxycarbonyl, aminocarbonyl, $C_1$-$C_4$-alkyl or $C_1$-$C_4$-alkoxycarbonyl,
whereby alkyl is substituted with a substituent, whereby the substituent is selected from the group consisting of hydroxy, hydroxycarbonyl, aminocarbonyl and $C_1$-$C_4$-alkoxycarbonyl,
$R^5$ and $R^6$ independently of one another are attached at position 3, 4 or 5 and independently of one another represent hydrogen, hydroxy, methyl, or ethyl,
and
Y represents a methylene group or an oxygen atom,
or one of its salts.

3. The compound of claim 2, whereby
$R^1$ represents hydrogen, fluorine or chlorine,
$R^3$ represents halogen, hydroxy, $C_1$-$C_3$-alkoxy, cyano, trifluoromethyl, monofluoromethoxy, difluoromethoxy or trifluoromethoxy,
$R^4$ represents $C_1$-$C_6$-alkyl or $C_3$-$C_6$-cycloalkyl,
whereby alkyl can be substituted with 1 to 3 substituents, whereby the substituents are selected independently of one another from the group consisting of halogen, hydroxy, amino, cyano, trifluoromethyl and $C_1$-$C_4$-alkoxy,
and
whereby cycloalkyl can be substituted with 1 to 3 substituents, whereby the substituents are selected independently of one another from the group consisting of halogen, hydroxy, amino, cyano, trifluoromethyl, $C_1$-$C_4$-alkyl and $C_1$-$C_4$-alkoxy,
or
$R^3$ and $R^4$, together with the atoms to which they are attached, form a ring through a group of formula

[Chemical structure: *-O-CH2-CH(CH3)-# group]

whereby
* is the linkage site to the carbon atom,
and
# is the linkage site to the nitrogen atom,
$R^7$ and $R^8$ independently of one another represent halogen, cyano, trifluoromethyl, monofluoromethoxy, difluoromethoxy, trifluoromethoxy, $C_1$-$C_3$-alkyl or $C_1$-$C_3$-alkoxy, $R^{10}$ represents a group of formula

[Chemical structures: similar to above but with reduced substituent list]

whereby
* is the linkage site to the carbon atom,
$R^2$ is attached at position 3 or 4 and represents hydroxy, hydroxycarbonyl, aminocarbonyl, $C_1$-$C_4$-alkyl or $C_1$-$C_4$-alkoxycarbonyl,
whereby alkyl is substituted with a substituent, whereby the substituent is selected from the group consisting of hydroxycarbonyl and $C_1$-$C_4$-alkoxycarbonyl,
$R^5$ and $R^6$ independently of one another are attached at position 3, 4 or 5 and independently of one another represent hydrogen, hydroxy, methyl or ethyl,
and
Y represents a methylene group or an oxygen atom,
or one of its salts.

4. A medicament comprising a compound of claim 1 in combination with an inert, non-toxic, pharmaceutically acceptable excipient.

5. A method of controlling viral infections with the human cytomegalovirus (HCMV) in humans and animals by administering an antivirally effective amount of at least one compound of claim 1.

6. A method of controlling viral infections with the human cytomegalovirus (HCMV) in humans and animals by administering an antivirally effective amount of at least one compound of claim 2.

7. A method of controlling viral infections with the human cytomegalovirus (HCMV) in humans and animals by administering an antivirally effective amount of at least one compound of claim 3.

8. A method of controlling viral infections with the human cytomegalovirus (HCMV) in humans and animals by administering an antivirally effective amount of a medicament of claim 4.

9. A medicament comprising a compound of claim 2 in combination with an inert, non-toxic, pharmaceutically acceptable excipient.

10. A method of controlling viral infections with the human cytomegalovirus (HCMV) in humans and animals by administering an antivirally effective amount of a medicament of claim 9.

11. A medicament comprising a compound of claim 3 in combination with an inert, non-toxic, pharmaceutically acceptable excipient.

12. A method of controlling viral infections with the human cytomegalovirus (HCMV) in humans and animals by administering an antivirally effective amount of a medicament of claim 11.

* * * * *